(12) United States Patent
Liao et al.

(10) Patent No.: US 10,006,033 B2
(45) Date of Patent: *Jun. 26, 2018

(54) RECOMBINANT MICROORGANISMS HAVING A METHANOL ELONGATION CYCLE (MEC)

(71) Applicant: The Regents of the University of California, Oakland, CA (US)

(72) Inventors: James C. Liao, Los Angeles, CA (US); Igor Bogorad, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/853,946

(22) Filed: Sep. 14, 2015

(65) Prior Publication Data

US 2016/0060635 A1    Mar. 3, 2016

Related U.S. Application Data

(63) Continuation-in-part of application No. PCT/US2014/029603, filed on Mar. 14, 2014.

(60) Provisional application No. 61/785,143, filed on Mar. 14, 2013, provisional application No. 61/785,254, filed on Mar. 14, 2013, provisional application No. 62/055,533, filed on Sep. 25, 2014.

(51) Int. Cl.

| | |
|---|---|
| *C12P 7/16* | (2006.01) |
| *C12N 1/20* | (2006.01) |
| *C12P 7/18* | (2006.01) |
| *C12P 21/06* | (2006.01) |
| *C12P 19/34* | (2006.01) |
| *C07H 21/04* | (2006.01) |
| *C07K 1/00* | (2006.01) |
| *C12N 15/52* | (2006.01) |
| *C12P 7/06* | (2006.01) |
| *C12N 9/10* | (2006.01) |
| *C12N 9/88* | (2006.01) |

(52) U.S. Cl.
CPC .......... *C12N 15/52* (2013.01); *C12N 9/1022* (2013.01); *C12N 9/88* (2013.01); *C12P 7/06* (2013.01); *C12P 7/16* (2013.01); *C12Y 202/01003* (2013.01); *C12Y 401/02009* (2013.01); *C12Y 401/02022* (2013.01); *C12Y 401/02043* (2013.01); *Y02E 50/10* (2013.01); *Y02E 50/17* (2013.01)

(58) Field of Classification Search
CPC ............ C12N 15/52; C12Y 401/02022; C12Y 401/02009; C12P 7/16; C12P 7/06
USPC ................. 435/160, 252.33, 158, 69.1, 91.1; 536/23.1, 23.2; 530/350
See application file for complete search history.

(56) References Cited

U.S. PATENT DOCUMENTS

| | | | | | |
|---|---|---|---|---|---|
| 5,352,590 | A | * | 10/1994 | Kato ...................... | C12N 11/18 |
| | | | | | 435/105 |
| 8,349,587 | B2 | * | 1/2013 | Fischer .................... | C12P 5/00 |
| | | | | | 435/41 |
| 9,518,278 | B2 | * | 12/2016 | Liao .......................... | C12P 9/00 |
| 2011/0244536 | A1 | * | 10/2011 | Nagarajan ............. | C12N 9/0006 |
| | | | | | 435/146 |
| 2014/0058056 | A1 | * | 2/2014 | Burgard .................... | C12P 7/18 |
| | | | | | 528/85 |

FOREIGN PATENT DOCUMENTS

| | | | | | |
|---|---|---|---|---|---|
| WO | WO 2012/098662 | | * | 7/2012 | ............ C12N 15/09 |
| WO | WO 2013/007786 | | * | 1/2013 | ............... C12N 9/04 |
| WO | 2014/165763 | A1 | | 10/2014 | |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kato et al., The physiological role of the ribulose monophosphate pathway in bacteraia and archaea. Biosci. Biotechnol. Biochem., 2006, vol. 70 (1): 10-21.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*

(Continued)

*Primary Examiner* — Ganapathirama Raghu
(74) *Attorney, Agent, or Firm* — Gavrilovich, Dodd & Lindsey LLP

(57) ABSTRACT

Provided are microorganisms that catalyze the synthesis of chemicals and biochemicals from a methanol, methane and/or formaldehyde. Also provided are methods of generating such organisms and methods of synthesizing chemicals and biochemicals using such organisms.

18 Claims, 15 Drawing Sheets

(56) References Cited

OTHER PUBLICATIONS

Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
Bai, Lingfei, International Preliminary Report on Patentability, PCT/US2014/029603, dated Sep. 24, 2015.

* cited by examiner

FIG. 1A

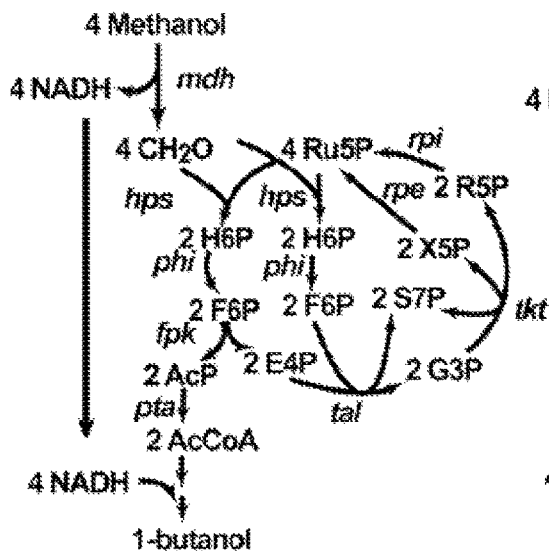

FIG. 1B

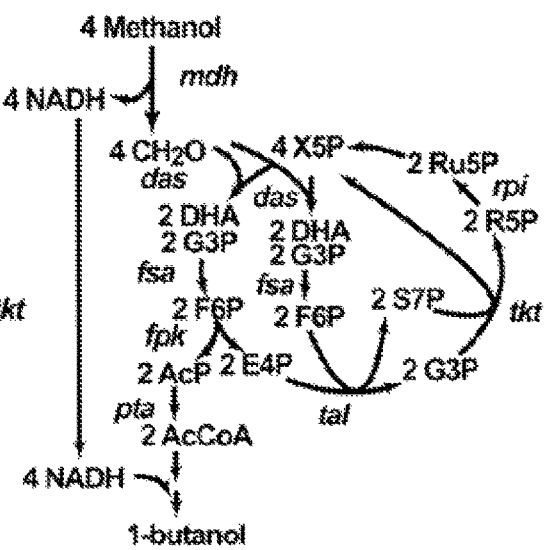

| Name | Abbrev. | Verified Source |
|---|---|---|
| F6P-Phosphoketolase | Fpk | *B. adolescentis*· |
| X5P-Phosphoketolase | Xpk | *L. plantarum* |
| Transaldolase | Tal | *E. coli* |
| Transketolase | Tkt | *E. coli* |
| Ribose-5-phosphate isomerase | Rpi | *E. coli* |
| Ribulose-3-phosphate epimerase | Rpe | *E. coli* |
| Methanol Dehydrogenase | Mdh | *B. methanolicus* |
| Hexulose-6-phosphate synthase | Hps | *B. subtilis* |
| Hexulose-6-phosphate isomerase | Phi | *M. flagellus* |
| Dihydroxyacetone synthase | Das | *C. boindii* |
| Fructose-6-phosphate aldolase | Fsa | *S. enterica* |
| Phosphotransacetylase | Pta | *E. coli* |
| Acetate Kinase | Ack | *E. coli* |

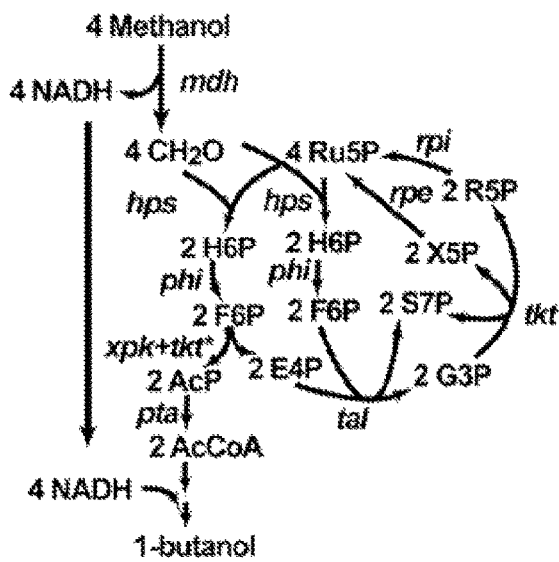
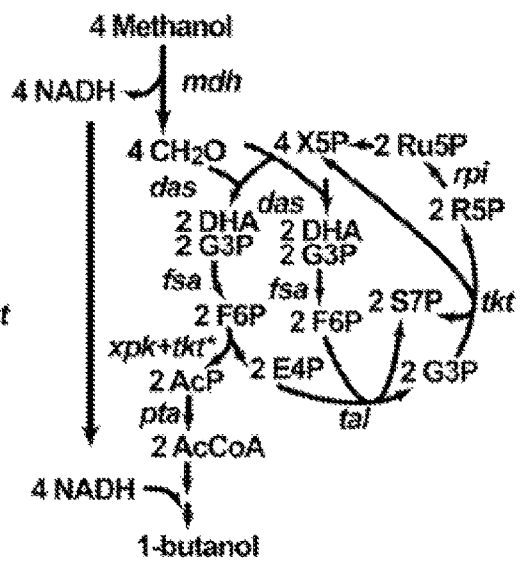

| Name | Abbrev. | Verified Source |
|---|---|---|
| F6P-Phosphoketolase | Fpk | B. adolescentis* |
| X5P-Phosphoketolase | Xpk | L. plantarum |
| Transaldolase | Tal | E. coli |
| Transketolase | Tkt | E. coli |
| Ribose-5-phosphate isomerase | Rpi | E. coli |
| Ribulose-3-phosphate epimerase | Rpe | E. coli |
| Methanol Dehydrogenase | Mdh | B. methanolicus |
| Hexulose-6-phosphate synthase | Hps | B. subtilis |
| Hexulose-6-phosphate isomerase | Phi | M. flagellus |
| Dihydroxyacetone synthase | Das | C. boindii |
| Fructose-6-phosphate aldolase | Fsa | S. enterica |
| Phosphotransacetylase | Pta | E. coli |
| Acetate Kinase | Ack | E. coli |

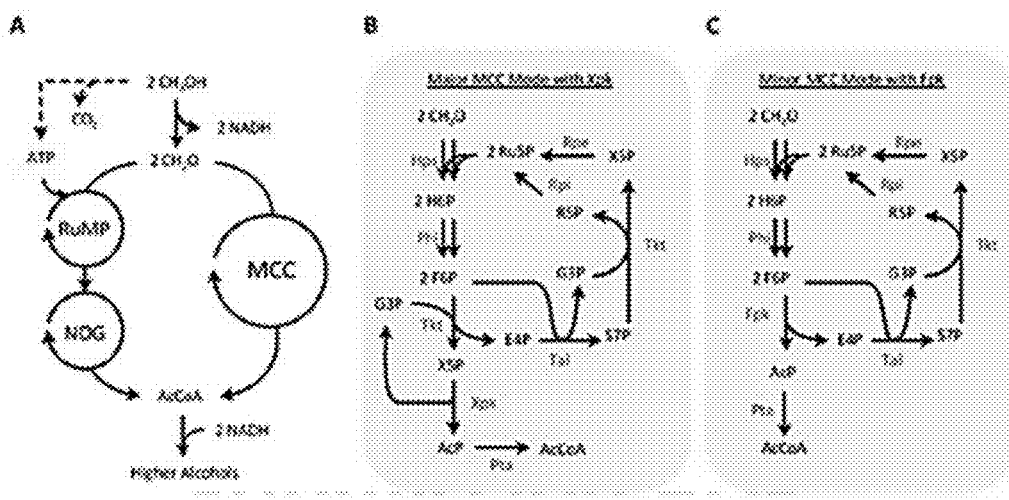
*FIG. 12A*  *FIG. 12B*  *FIG. 12C*
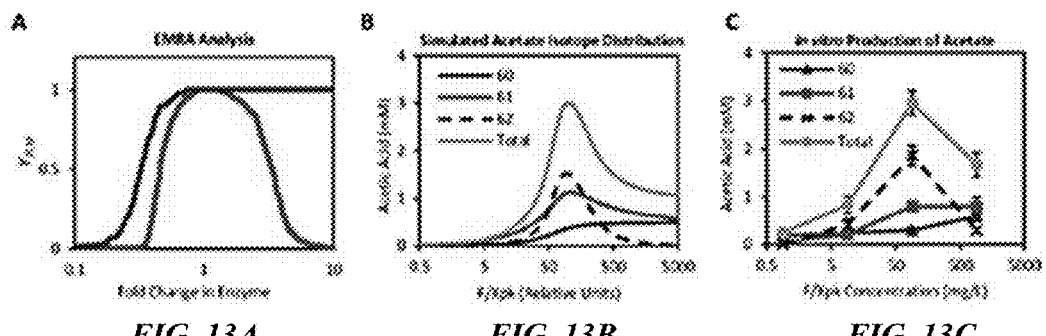
*FIG. 13A*  *FIG. 13B*  *FIG. 13C*

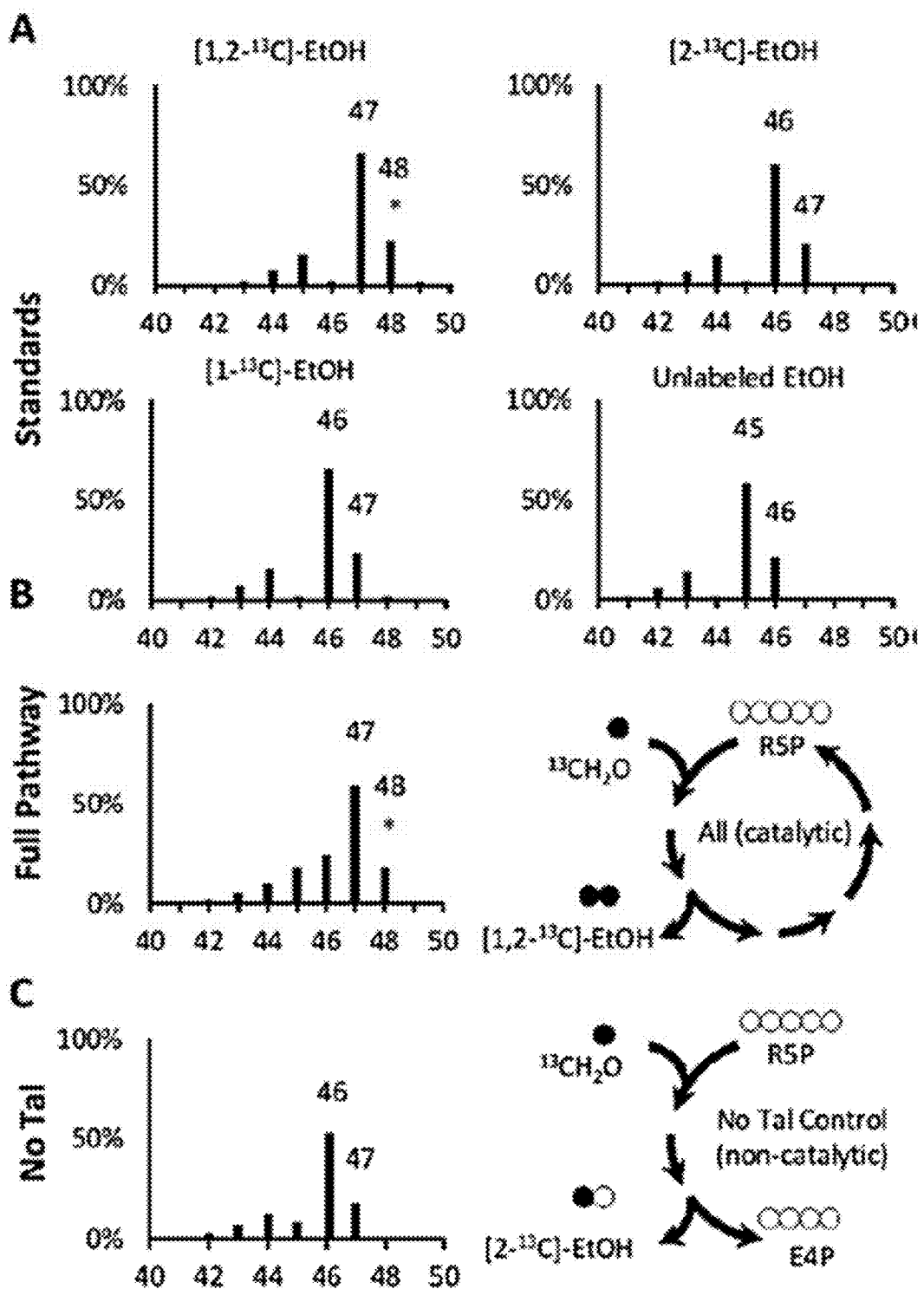
FIG. 14A-C

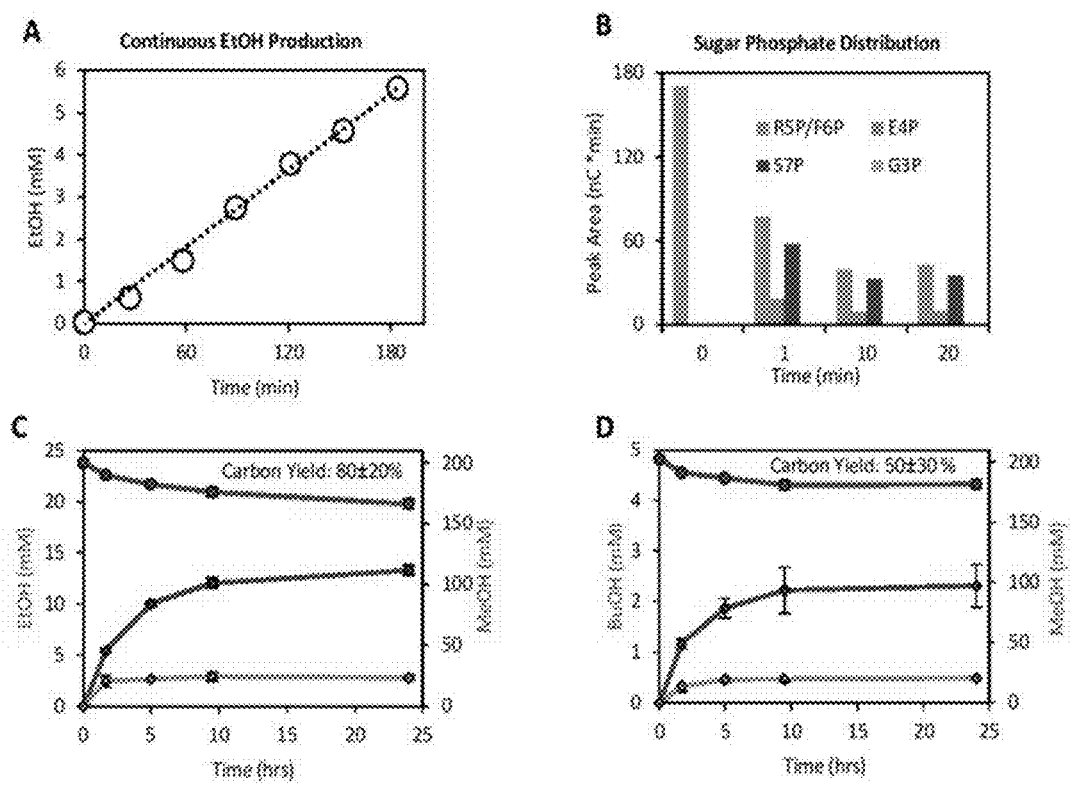
*FIG. 15A-D*

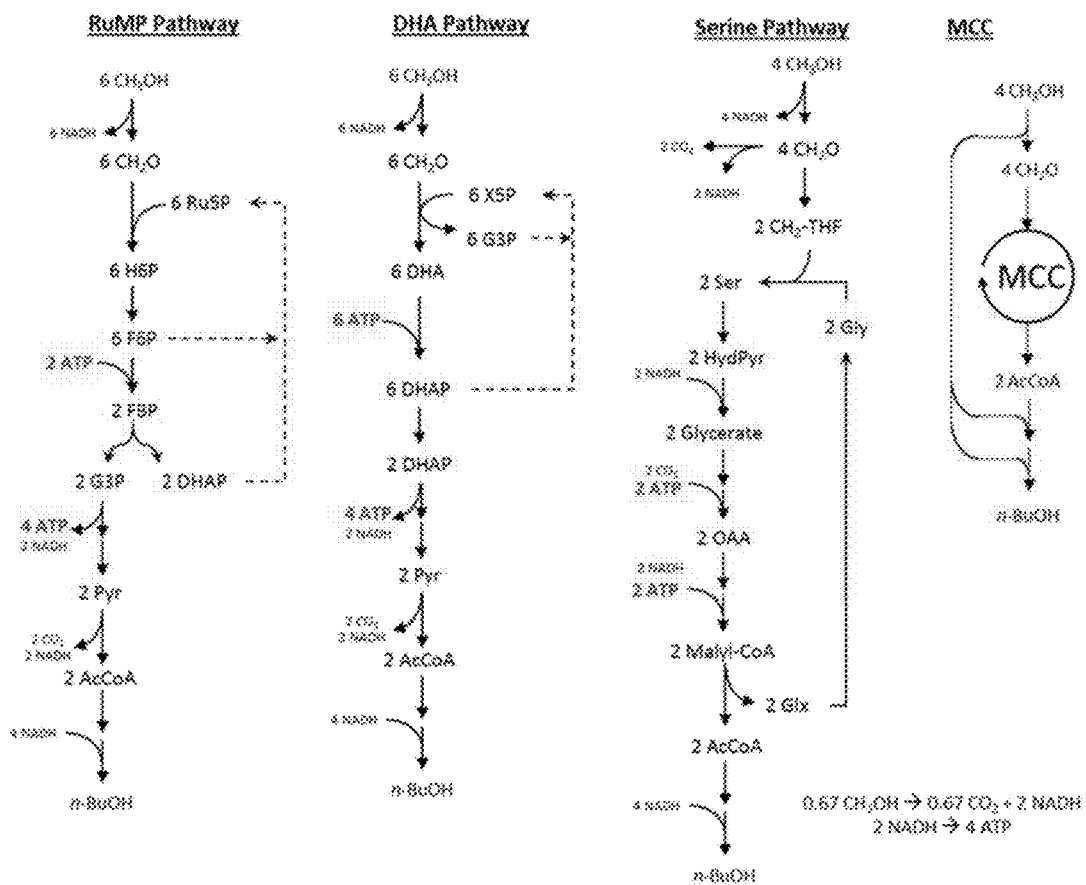
FIG. 16
A)
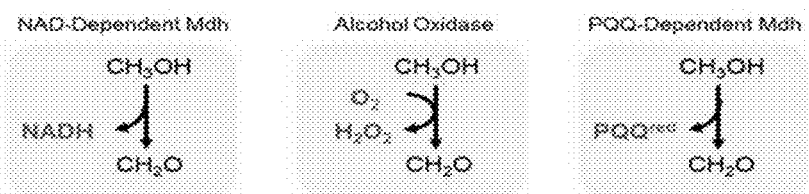
B)
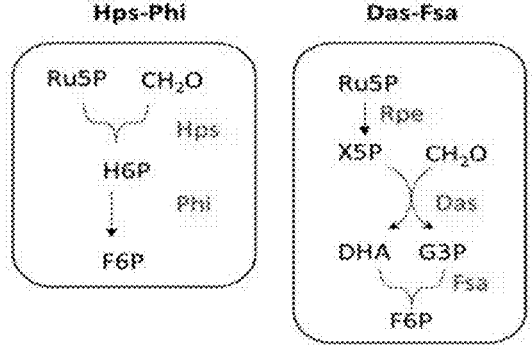
FIG. 17A-B

RECOMBINANT MICROORGANISMS HAVING A METHANOL ELONGATION CYCLE (MEC)

CROSS REFERENCE TO RELATED APPLICATIONS

This application is a continuation-in-part application of International Application No. PCT/US2014/029603, filed Mar. 14, 2014, which claims priority to U.S. Provisional Application No. 61/785,143, filed Mar. 14, 2013 and 61/785,254, filed Mar. 14, 2013; this application also claims priority to U.S. Provisional Application Ser. No. 62/055,533, filed Sep. 25, 2014, the disclosures of which are incorporated herein by reference.

STATEMENT REGARDING FEDERALLY SPONSORED RESEARCH

This invention was made with Government support under DE-AR0000430, awarded by the U.S. Department of Energy Advanced Research Projects Agency, and 0963183, awarded by the National Science Foundation. The Government has certain rights in the invention.

TECHNICAL FIELD

Metabolically-modified microorganisms and methods of producing such organisms are provided. Also provided are methods of producing chemicals by contacting a suitable substrate with a metabolically-modified microorganism and enzymatic preparations of the disclosure.

BACKGROUND

Acetyl-CoA is a central metabolite key to both cell growth as well as biosynthesis of multiple cell constituents and products, including fatty acids, amino acids, isoprenoids, and alcohols. Typically, the Embden-Meyerhof-Parnas (EMP) pathway, the Entner-Doudoroff (ED) pathway, and their variations are used to produce acetyl-CoA from sugars through oxidative decarboxylation of pyruvate. Similarly, the CBB, RuMP, and DHA pathways incorporate C1 compounds, such as $CO_2$ and methanol, to synthesize sugar-phosphates and pyruvate, which then produce acetyl-CoA through decarboxylation of pyruvate. Thus, in all heterotrophic organisms and those autotrophic organisms that use the sugar-phosphate-dependent pathways for C1 incorporation, acetyl-coA is derived from oxidative decarboxylation of pyruvate, resulting in loss of one molecule of $CO_2$ per molecule of pyruvate. While the EMP route to acetate and ethanol has been optimized, the $CO_2$ loss problem has not been solved due to inherent pathway limitations. Without using a $CO_2$ fixation pathway, such as the Wood-Ljungdahl pathway or the reductive TCA cycle, the waste $CO_2$ leads to a significant decrease in carbon yield. This loss of carbon has a major impact on the overall economy of biorefinery and the carbon efficiency of cell growth.

SUMMARY

The disclosure provides a recombinant microorganism comprising a metabolic pathway for the synthesis of acetyl phosphate from formaldehyde using a pathway comprising (i) an enzyme having phosphoketolase activity and (ii) (a) an enzyme having hexulose-6-phosphate synthase activity, or (b) an enzyme having dihydroxyacetone synthase activity, wherein the microorganism has an acetyl-phosphate yield better than a wild-type or parental organism. The microorganism can be prokaryotic or eukaryotic (e.g., a yeast). The parental microorganism can comprise genes that encode polypeptides having the foregoing activity, but the polypeptides are not optimally active in concert, in which instance that organism can be engineered to improve or modify the expression of the genes. Alternatively, where the parental microorganism does not have such enzymes, polynucleotides encoding polypeptides having the activity can be cloned into the microorganism and expressed.

The disclosure also provides a recombinant microorganism comprising a metabolic pathway for the synthesis of acetyl phosphate from formaldehyde using a pathway comprising (i) an enzyme having phosphoketolase activity and (ii) (a) an enzyme having hexulose-6-phosphate synthase activity and an enzyme having hexulose-6-phosphate isomerase, or (b) an enzyme having dihdroxyacetone synthase and an enzyme having fructose-6-phosphate aldolase activity, wherein the microorganism has an acetyl-phosphate yield better than a wild-type or parental organism. The microorganism can be prokaryotic or eukaryotic (e.g., a yeast). The parental microorganism can comprise genes that encode polypeptides having the foregoing activity, but are not optimally active in concert, in which instance that organism can be engineered to improve or modify the expression of the genes. Alternatively, where the microorganism does not have such enzymes, the polynucleotides encoding polypeptides having the activity can be cloned into the microorganism and expressed.

In one embodiment of the foregoing, the parental microorganism is an *E. coli* microorganism. In a further embodiment, the *E. coli* expresses, is engineered to express or engineered to overexpress a phosphoketolase. In another embodiment, the phosphoketolase is Fpk, Xpk or a bifunctional F/Xpk enzyme or homolog thereof. In yet another embodiment of any of the foregoing, the microorganism is engineered to heterologously expresses one or more of the following enzymes: (a) a phosphoketolase; (b) a transaldolase; (c) a transketolase; (d) a ribose-5-phosphate isomerase; (e) a ribulose-5-phosphate epimerase; (f) a hexulose-6-phosphate synthase; (g) a hexulose-6-phosphate isomerase; (h) a dihydroxyacetone synthase; and/or (i) a fructose-6-phosphate aldolase. In yet another embodiment of any of the foregoing, the microorganism expresses, is engineered to express or engineered to overexpress a phosphoketolase derived from *Bifidobaceterium adolescentis*. In yet another embodiment of any of the foregoing, the phosphoketolase is a bifunctional F/Xpk. In yet another embodiment of any of the foregoing, the phosphoketolase comprises a sequence that is at least 49% identical to SEQ ID NO:2 and has phosphoketolase activity. In yet another embodiment of any of the foregoing, the microorganism expresses, is engineered to express or engineered to overexpress a hexulose-6-phosphate synthase. In a further embodiment, the hexulose-6-phosphate synthase is Hps or a homolog thereof. In still a further embodiment, the hexulose-6-phosphate synthase is 70% identical to SEQ ID NO:14 and has hexulose-6-phosphate synthase activity. In yet another embodiment of any of the foregoing, the microorganism is engineered expresses, is engineered to express or engineered to overexpress a hexulose-6-phosphate isomerase. In a further embodiment, the hexulose-6-phosphate isomerase is Phi or a homolog thereof. In still a further embodiment, the hexulose-6-phosphate isomerase is 70% identical to SEQ ID NO:16 and has hexulose-6-phosphate isomerase activity. In yet another embodiment of any of the foregoing, the microorganism expresses, is engineered to express or engineered to overexpress a dihydroxyacetone synthase. In a further embodiment, the dihydroxyacetone synthase is Das or a homolog thereof. In still a further embodiment, the dihydroxyacetone synthase is 70% identical to SEQ ID NO:18 and has dihydroxyacetone synthase activity. In yet another embodiment of any of the foregoing, the microorganism expresses, is engineered to express or engineered to overexpress a fructose-6-phosphate aldolase. In a further embodiment, the fructose-6-phosphate aldolase is Fsa or a homolog thereof. In still a further embodiment, the fructose-6-phosphate aldolase is 70% identical to SEQ ID NO:20 and has fructose-6-phosphate aldolase activity. In yet another embodiment of any of the foregoing, the microorganism expresses, is engineered to express or engineered to overexpress a ribulose-5-phosphate epimerase. In a further embodiment, the ribulose-5-phosphate epimerase is Rpe or a homolog thereof. In still another embodiment, the ribulose-5-phosphate epimerase has at least 50% identity to SEQ ID NO:6 and has ribulose-5-phosphate epimerase activity. In yet another embodiment of any of the foregoing, the microorganism expresses, is engineered to express or engineered to overexpress a ribose-5-phosphate isomerase. In a further embodiment, the ribose-5-phosphate isomerase is Rpi or a homolog thereof. In still a further embodiment, the ribose-5-phosphate isomerase has at least 37% identity to SEQ ID NO:8 and has ribose-5-phosphate isomerase activity. In yet another embodiment of any of the foregoing, the microorganism expresses, is engineered to express or engineered to overexpress a transaldolase. In a further embodiment, the transaldolase is Tal or a homolog thereof. In still a further embodiment, the transaldolase has at least 30% identity to SEQ ID NO:10 and has transaldolase activity. In yet another embodiment of any of the foregoing, the microorganism expresses, is engineered to express or engineered to overexpress transketolase. In a further embodiment, the transketolase is Tkt or a homolog thereof. In still a further embodiment, the transketolase has at least 40% identity to SEQ ID NO:12 and has transketolase activity. In yet another embodiment of any of the foregoing, the microorganism expresses, is engineered to express or engineered to overexpress a methanol dehydrogenase. In a further embodiment, the methanol dehydrogenase is Mdh or a homolog thereof. In still a further embodiment, the methanol dehydrogenase has at least 70% identity to SEQ ID NO:4 and has methanol dehydrogenase activity. In yet another embodiment of any of the foregoing, the microorganism expresses, is engineered to express or engineered to overexpress an alcohol oxidase. In a further embodiment, the alcohol oxidase is Aox or a homolog thereof. In still a further embodiment, the alcohol oxidase has at least 70% identity to SEQ ID NO:22 and has alcohol oxidase activity. In yet another embodiment, the microorganism converts a C1 alcohol to an aldehyde. In yet a further embodiment, the microorganism converts methanol to formaldehyde. In yet another embodiment of any of the foregoing, the microorganism is further engineered to have a reduction or knockout of expression of one or more of ldhA, frdBC, adhE, ackA, pflB, frmA, frmB/yeiG and gapA. In yet another embodiment, the microorganism is further engineered to produce isobutanol or n-butanol. In a further embodiment, the microorganism expresses or over expresses a phosphate acetyltrasferase that converts acetyl phosphate to acetyl-CoA. In yet a further embodiment, the microorganism produced isobutanol and comprises expression or over expression of one or more enzymes selected from the group consisting of: acetyl-CoA acetyltransferase, an acetoacetyl-CoA transferase, an acetoacetate decarboxylase) and an adh (secondary alcohol dehydrogenase). In another embodiment, the microorganism comprises one or more deletions or knockouts in a gene encoding an enzyme that catalyzes the conversion of acetyl-coA to ethanol, catalyzes the conversion of pyruvate to lactate, catalyzes the conversion of acetyl-coA and phosphate to coA and acetyl phosphate, catalyzes the conversion of acetyl-coA and formate to coA and pyruvate, or condensation of the acetyl group of acetyl-CoA with 3-methyl-2-oxobutanoate (2-oxoisovalerate). In another embodiment, the microorganism produces n-butanol and comprises expression or over expression of one or more enzymes selected from the group consisting of: a keto thiolase or an acetyl-CoA acetyltransferase activity, a hydroxybutyryl-CoA dehydrogenase activity, a crotonase activity, a crotonyl-CoA reductase or a butyryl-CoA dehydrogenase, and an alcohol dehydrogenase. In another embodiment, the microorganism produces n-butanol and comprises expression or over expression of one or more enzymes that convert acetyl-CoA to malonyl-CoA, malonyl-CoA to Acetoacetyl-CoA, and at least one enzyme that converts (a) acetoacetyl-CoA to (R)- or (S)-3-hydroxybutyryl-CoA and (R)- or (S)-3-hydroxybutyryl-CoA to crotonyl-CoA, crotonyl-CoA to butyryl-CoA, butyryl-CoA to butyraldehyde and butyraldehyde to 1-butanol. In a further embodiment, the microorganism expresses an acetyl-CoA carboxylase and an acetoacetyl-CoA synthase and one or more enzymes selected from the group consisting of (a) hydroxybutyryl CoA dehydrogenase, (b) crotonase, (c) trans-2-enoyl-CoA reductase, and (d) an alcohol/aldehyde dehydrogenase.

In one embodiment, the microorganism is a eukaryotic microorganism. In a further embodiment, the eukaryotic organism is a yeast. In yet a further embodiment, the yeast is engineered to express or engineered to overexpress a phosphoketolase. In another embodiment, the phosphoketolase is Fpk, Xpk or a bifunctional F/Xpk enzyme or homolog thereof. In yet another embodiment of any of the foregoing, the microorganism is engineered to heterologously expresses one or more of the following enzymes: (a) a phosphoketolase; (b) a transaldolase; (c) a transketolase; (d) a ribose-5-phosphate isomerase; (e) a ribulose-5-phosphate epimerase; (f) a hexulose-6-phosphate synthase; (g) a hexulose-6-phosphate isomerase; (h) a dihydroxyacetone synthase; and (i) a fructose-6-phosphate aldolase. In yet another embodiment of any of the foregoing, the microorganism expresses, is engineered to express or engineered to overexpress a phosphoketolase derived from *Bifidobaceterium adolescentis*. In yet another embodiment of any of the foregoing, the phosphoketolase is a bifunctional F/Xpk. In yet another embodiment of any of the foregoing, the phosphoketolase comprises a sequence that is at least 49% identical to SEQ ID NO:2 and has phosphoketolase activity. In yet another embodiment of any of the foregoing, the microorganism expresses, is engineered to express or engineered to overexpress a hexulose-6-phosphate synthase. In a further embodiment, the hexulose-6-phosphate synthase is Hps or a homolog thereof. In still a further embodiment, the hexulose-6-phosphate synthase is 70% identical to SEQ ID NO:14 and has hexulose-6-phosphate synthase activity. In yet another embodiment of any of the foregoing, the microorganism is engineered expresses, is engineered to express or engineered to overexpress a hexulose-6-phosphate isomerase. In a further embodiment, the hexulose-6-phosphate isomerase is Phi or a homolog thereof. In still a further embodiment, the hexulose-6-phosphate isomerase is 70% identical to SEQ ID NO:16 and has hexulose-6-phosphate isomerase activity. In yet another embodiment of any of the foregoing, the microorganism expresses, is engineered to express or engineered to overexpress a dihydroxyacetone synthase. In a further embodiment, the dihydroxyacetone synthase is Das or a homolog thereof. In still a further embodiment, the dihydroxyacetone synthase is 70% identical to SEQ ID NO:18 and has dihydroxyacetone synthase activity. In yet another embodiment of any of the foregoing, the microorganism expresses, is engineered to express or engineered to overexpress a fructose-6-phosphate aldolase. In a further embodiment, the fructose-6-phosphate aldolase is Fsa or a homolog thereof. In still a further embodiment, the fructose-6-phosphate aldolase is 70% identical to SEQ ID NO:20 and has fructose-6-phosphate aldolase activity. In yet another embodiment of any of the foregoing, the microorganism expresses, is engineered to express or engineered to overexpress a ribulose-5-phosphate epimerase. In a further embodiment, the ribulose-5-phosphate epimerase is Rpe or a homolog thereof. In still another embodiment, the ribulose-5-phosphate epimerase has at least 50% identity to SEQ ID NO:6 and has ribulose-5-phosphate epimerase activity. In yet another embodiment of any of the foregoing, the microorganism expresses, is engineered to express or engineered to overexpress a ribose-5-phosphate isomerase. In a further embodiment, the ribose-5-phosphate isomerase is Rpi or a homolog thereof. In still a further embodiment, the ribose-5-phosphate isomerase has at least 37% identity to SEQ ID NO:8 and has ribose-5-phosphate isomerase activity. In yet another embodiment of any of the foregoing, the microorganism expresses, is engineered to express or engineered to overexpress a transaldolase. In a further embodiment, the transaldolase is Tal or a homolog thereof. In still a further embodiment, the transaldolase has at least 30% identity to SEQ ID NO:10 and has transaldolase activity. In yet another embodiment of any of the foregoing, the microorganism expresses, is engineered to express or engineered to overexpress transketolase. In a further embodiment, the transketolase is Tkt or a homolog thereof. In still a further embodiment, the transketolase has at least 40% identity to SEQ ID NO:12 and has transketolase activity. In yet another embodiment of any of the foregoing, the microorganism expresses, is engineered to express or engineered to overexpress a methanol dehydrogenase. In a further embodiment, the methanol dehydrogenase is Mdh or a homolog thereof. In still a further embodiment, the methanol dehydrogenase has at least 70% identity to SEQ ID NO:4 and has methanol dehydrogenase activity. In yet another embodiment of any of the foregoing, the microorganism expresses, is engineered to express or engineered to overexpress an alcohol oxidase. In a further embodiment, the alcohol oxidase is Aox or a homolog thereof. In still a further embodiment, the alcohol oxidase has at least 70% identity to SEQ ID NO:22 and has alcohol oxidase activity. In yet another embodiment, the microorganism converts a C1 alcohol to an aldehyde. In yet a further embodiment, the microorganism converts methanol to formaldehyde. In yet another embodiment of any of the foregoing, the microorganism is further engineered to have a reduction or knockout of expression of one or more enzymes selected from the group consisting of: a pyruvate decarboxylase and a glyceraldehyde-3-phosphate dehydrogenase. In an further embodiment, the microorganism has a reduction or knockout of expression of one or more of PDC1, PDC5, PDC6, TDH1, TDH2, TDH3, SFA1 or YJL068C. In yet another embodiment, the microorganism is further engineered to produce isobutanol or n-butanol. In a further embodiment, the microorganism expresses or over expresses a phosphate acetyltrasferase that converts acetyl phosphate to acetyl-CoA. In yet a further embodiment, the microorganism produced isobutanol and comprises expression or over expression of one or more enzymes selected from the group consisting of: acetyl-CoA acetyltransferase, an acetoacetyl-CoA transferase, an acetoacetate decarboxylase) and an adh (secondary alcohol dehydrogenase). In another embodiment, the microorganism comprises one or more deletions or knockouts in a gene encoding an enzyme that catalyzes the conversion of acetyl-coA to ethanol, catalyzes the conversion of pyruvate to lactate, catalyzes the conversion of acetyl-coA and phosphate to coA and acetyl phosphate, catalyzes the conversion of acetyl-coA and formate to coA and pyruvate, or condensation of the acetyl group of acetyl-CoA with 3-methyl-2-oxobutanoate (2-oxoisovalerate). In another embodiment, the microorganism produces n-butanol and comprises expression or over expression of one or more enzymes selected from the group consisting of: a keto thiolase or an acetyl-CoA acetyltransferase activity, a hydroxybutyryl-CoA dehydrogenase activity, a crotonase activity, a crotonyl-CoA reductase or a butyryl-CoA dehydrogenase, and an alcohol dehydrogenase. In another embodiment, the microorganism produces n-butanol and comprises expression or over expression of one or more enzymes that convert acetyl-CoA to malonyl-CoA, malonyl-CoA to Acetoacetyl-CoA, and at least one enzyme that converts (a) acetoacetyl-CoA to (R)- or (S)-3-hydroxybutyryl-CoA and (R)- or (S)-3-hydroxybutyryl-CoA to crotonyl-CoA, crotonyl-CoA to butyryl-CoA, butyryl-CoA to butyraldehyde and butyraldehyde to 1-butanol. In a further embodiment, the microorganism expresses an acetyl-CoA carboxylase and an acetoacetyl-CoA synthase and one or more enzymes selected from the group consisting of (a) hydroxybutyryl CoA dehydrogenase, (b) crotonase, (c) trans-2-enoyl-CoA reductase, and (d) an alcohol/aldehyde dehydrogenase.

The disclosure provides a recombinant microorganism comprising a metabolic pathway for the synthesis of acetyl phosphate from formaldehyde using a pathway comprising (i) an enzyme having phosphoketolase activity and (ii) (a) a hexulose-6-phosphate synthase and hexulose-6-phosphate isomerase, or (b) dihdroxyacetone synthase and a fructose-6-phosphate aldolase wherein the microorganism has an acetyl-phosphate yield better than a wild-type or parental organism.

In another embodiment, the disclosure provides a recombinant microorganism comprising a pathway that produces acetyl-phosphate through carbon rearrangement of E4P and/or G3P and metabolism of a carbon source selected from methane, methanol, or formaldehyde, wherein the microorganism expresses (i) an enzyme having phosphoketolase activity and (ii) (a) a hexulose-6-phosphate synthase, or (b) dihydroxyacetone synthase. In one embodiment, the microorganism is engineered to heterologously expresses (i) an enzyme having phosphoketolase activity and (ii) (a) a hexulose-6-phosphate synthase and hexulose-6-phosphate isomerase, or (b) dihdroxyacetone synthase and a fructose-6-phosphate aldolase and one or more of the following enzymes: (a) a transaldolase (Tal); (b) a transketolase (Tkt); (c) a ribose-5-phosphate isomerase (Rpi); (d) a ribulose-5-phosphate epimerase (Rpe); and (e) a methanol dehydrogenase (Mdh).

The disclosure also provides a recombinant microorganism expressing enzymes that catalyze the conversion described in (i)-(xi), wherein at least one enzyme or the regulation of at least one enzyme that performs a conversion described in (i)-(xi) is heterologous to the microorganism: (i) the production of acetyl-phosphate and erythrose-4- phosphate (E4P) from fructose-6-phosphate and/or the production of acetyl-phosphate and glyceraldehyde 3-phosphate (G3P) from xylulose 5-phosphate; (ii) the reversible conversion of fructose-6-phosphate and E4P to sedoheptulose 7-phosphate (S7P) and (G3P); (iii) the reversible conversion of S7P and G3P to ribose-5-phosphate and xylulose-5-phosphate; (iv) the reversible conversion of ribose-5-phosphate to ribulose-5-phosphate; (v) the reversible conversion of ribulose-5-phosphate to xylulose-5-phosphate; (vi) the reversible conversion of xylulose-5-phosphate and E4P to fructose-6-phosphate and glyceraldehyde-3-phosphate; (vii) the conversion of formaldehyde and ribulose-5-phosphate to D-arabino-3-Hexulose 6-phosphate; (viii) the reversible conversion of D-arabino-3-Hexulose 6-phosphate to fructose-6-phospahte; (ix) the conversion of formaldehyde and xylulose-5-phosphate to glyceraldehyde-3-phosphate and dihydroxyacetone; (x) the conversion of glyceraldehyde-3-phosphate and dihydroxyacetone to fructose-6-phosphate; and (xi) the conversion of methanol and an oxidized electron acceptor to formaldehyde and a reduced electron acceptor; wherein the microorganism produces acetyl-phosphate, or compounds derived from acetyl-phosphate using a carbon source selected from the group consisting of methanol, methane, and formaldehyde and any combination thereof.

The disclosure provides a recombinant *E. coli* that produces acetyl-phosphate comprising a genotype Fpk, Hps, and Phi. In one embodiment, the *E. coli* further comprises Tkt, Tal, Rpe, and Rpi. In a further embodiment, the *E. coli* comprises atoB, hbd, crt, ter, and adhE2, and wherein the *E. coli* produces 1-butanol. In yet a further embodiment, the *E. coli* can comprise pta. In another embodiment, the *E. coli* further comprises one or more knockouts selected from the group consisting of: ΔgapA, ΔldhA, ΔpflB, ΔfrmA, ΔfrmB/yeiG, ΔfrdBC, ΔadhE, and ΔackA.

In another embodiment, the disclosure provides a recombinant yeast organism that produces acetyl-phosphate comprising a genotype Fpk, Hps, and Phi. The yeast organism can further comprise Tkt, Tal, Rpe, and Rpi. In still another embodiment, the yeast can further comprise atoB, hbd, crt, ter, and adhE2, and wherein the yeast produces 1-butanol. In still another embodiment, the yeast can further comprise pta. The yeast can further comprise one or more knockouts selected from the group consisting of: Δpdc, Δsfa1, Δtdh, and ΔYJL068C.

The disclosure also provides a recombinant *Bacillus methanolicus* that produces acetyl-phosphate comprising a genotype fpk, xpk or f/xpk. The *B. methanolicus* can further comprise atoB, hbd, crt, ter, and adhE2, and wherein the *Bacillus methanolicus* produces 1-butanol.

The disclosure also provides a recombinant microorganism comprising a metabolic pathway for the synthesis of acetyl phosphate from methanol, methane or formaldehyde using a pathway comprising an enzyme having fructose-6-phosphoketolase activity and/or xylulose-5-phosphoketolase activity and wherein the microorganism produces a metabolite selected from the group consisting of citrate, isocitrate, alpha-ketoglutarate, glutamate and any combination thereof.

In any of the foregoing embodiments, the recombinant microorganism can comprise an acetyl-phosphate yield from a C1 carbon source better than 2:1, 2.9:1, 2.8:1, 2.7:1, 2.6:1, 2.5:1, or 2.1:1 (C1 carbon source to acetyl-phosphate).

For industrial applications, the carbon utilization pathway of the disclosure can be used to improve carbon yield in the production of fuels and chemicals derived from acetyl-CoA, such fuels including, but not limited to, acetate, n-butanol, isobutanol, ethanol, biodiesel and the like. If additional reducing power such as hydrogen or formic acid is provided, the carbon utilization pathway of the disclosure can be used to produce compounds that are more reduced than the substrate, for example, ethanol, 1-butanol, isoprenoids, and fatty acids from sugar.

In another embodiment, the disclosure provides an in vitro metabolic pathway comprising a plurality of polypeptides having enzymatic activity that converts a carbon source, such as methanol or formaldehyde, to acetyl phosphate. The disclosure provides an in vitro pathway for the synthesis of acetyl phosphate from formaldehyde using a pathway comprising (i) an enzyme having phosphoketolase activity and (ii) (a) an enzyme having hexulose-6-phosphate synthase activity and an enzyme having hexulose-6-phosphate isomerase, or (b) an enzyme having dihdroxyacetone synthase and an enzyme having fructose-6-phosphate aldolase activity, wherein the pathway produces acetyl-phosphate. The pathway can be developed by (i) expressing and isolating the enzyme(s) from a recombinant or non-recombinant microorganism; (ii) purchasing the enzyme(s) from a vendor; (iii) using a cell free (e.g., a disrupted or roughly or substantially purified) preparation of cellular material comprising the enzyme(s) or (iv) any combination of (i)-(iii). In another embodiment, the phosphoketolase is Fpk, Xpk or a bifunctional F/Xpk enzyme or homolog thereof. In yet another embodiment of any of the foregoing, the pathway includes one or more of the following enzymes: (a) a phosphoketolase; (b) a transaldolase; (c) a transketolase; (d) a ribose-5-phosphate isomerase; (e) a ribulose-5-phosphate epimerase; (f) a hexulose-6-phosphate synthase; (g) a hexulose-6-phosphate isomerase; (h) a dihydroxyacetone synthase; and/or (i) a fructose-6-phosphate aldolase. In yet another embodiment of any of the foregoing, the phosphoketolase is derived from *Bifidobaceterium adolescentis*. In yet another embodiment of any of the foregoing, the phosphoketolase is a bifunctional F/Xpk. In yet another embodiment of any of the foregoing, the phosphoketolase comprises a sequence that is at least 49% identical to SEQ ID NO:2 and has phosphoketolase activity. In yet another embodiment of any of the foregoing, the pathway comprises a hexulose-6-phosphate synthase. In a further embodiment, the hexulose-6-phosphate synthase is Hps or a homolog thereof. In still a further embodiment, the hexulose-6-phosphate synthase is 70% identical to SEQ ID NO:14 and has hexulose-6-phosphate synthase activity. In yet another embodiment of any of the foregoing, the pathway comprises a hexulose-6-phosphate isomerase. In a further embodiment, the hexulose-6-phosphate isomerase is Phi or a homolog thereof. In still a further embodiment, the hexulose-6-phosphate isomerase is 70% identical to SEQ ID NO:16 and has hexulose-6-phosphate isomerase activity. In yet another embodiment of any of the foregoing, the pathway comprises a dihydroxyacetone synthase. In a further embodiment, the dihydroxyacetone synthase is Das or a homolog thereof. In still a further embodiment, the dihydroxyacetone synthase is 70% identical to SEQ ID NO:18 and has dihydroxyacetone synthase activity. In yet another embodiment of any of the foregoing, the pathway comprises a fructose-6-phosphate aldolase. In a further embodiment, the fructose-6-phosphate aldolase is Fsa or a homolog thereof. In still a further embodiment, the fructose-6-phosphate aldolase is 70% identical to SEQ ID NO:20 and has fructose-6-phosphate aldolase activity. In yet another embodiment of any of the foregoing, the pathway comprises a ribulose-5-phosphate epimerase. In a further embodiment, the ribulose-5-phosphate epimerase is Rpe or a homolog thereof. In still another embodiment, the ribulose-5-phosphate epimerase has at least 50% identity to SEQ ID NO:6 and has ribulose-5-phosphate epimerase activity. In yet another embodiment of any of the foregoing, the pathway comprises a ribose-5-phosphate isomerase. In a further embodiment, the ribose-5-phosphate isomerase is Rpi or a homolog thereof. In still a further embodiment, the ribose-5-phosphate isomerase has at least 37% identity to SEQ ID NO:8 and has ribose-5-phosphate isomerase activity. In yet another embodiment of any of the foregoing, the pathway comprises a transaldolase. In a further embodiment, the transaldolase is Tal or a homolog thereof. In still a further embodiment, the transaldolase has at least 30% identity to SEQ ID NO:10 and has transaldolase activity. In yet another embodiment of any of the foregoing, the pathway comprises a transketolase. In a further embodiment, the transketolase is Tkt or a homolog thereof. In still a further embodiment, the transketolase has at least 40% identity to SEQ ID NO:12 and has transketolase activity. In yet another embodiment of any of the foregoing, pathway comprises a methanol dehydrogenase. In a further embodiment, the methanol dehydrogenase is Mdh or a homolog thereof. In still a further embodiment, the methanol dehydrogenase has at least 70% identity to SEQ ID NO:4 and has methanol dehydrogenase activity. In yet another embodiment of any of the foregoing, the pathway comprises an alcohol oxidase. In a further embodiment, the alcohol oxidase is Aox or a homolog thereof. In still a further embodiment, the alcohol oxidase has at least 70% identity to SEQ ID NO:22 and has alcohol oxidase activity. In yet another embodiment, the pathway converts a C1 alcohol to an aldehyde. In yet a further embodiment, the pathway converts methanol to formaldehyde. In yet another embodiment of any of the foregoing, the pathway lacks activity of one or more of ldhA, frdBC, adhE, ackA, pflB, frmA, frmB/yeiG and gapA. In yet another embodiment, the pathway is further engineered to produce isobutanol or n-butanol. In a further embodiment, the pathway comprises a phosphate acetyltrasferase that converts acetyl phosphate to acetyl-CoA. In yet a further embodiment, the pathway produces isobutanol and comprises one or more enzymes selected from the group consisting of: acetyl-CoA acetyltransferase, an acetoacetyl-CoA transferase, an acetoacetate decarboxylase) and an adh (secondary alcohol dehydrogenase). In another embodiment, the pathway lacks any activity that catalyzes the conversion of acetyl-coA to ethanol, catalyzes the conversion of pyruvate to lactate, catalyzes the conversion of acetyl-coA and phosphate to coA and acetyl phosphate, catalyzes the conversion of acetyl-coA and formate to coA and pyruvate, or condensation of the acetyl group of acetyl-CoA with 3-methyl-2-oxobutanoate (2-oxoisovalerate). In another embodiment, the pathway produces n-butanol and comprises one or more enzymes selected from the group consisting of: a keto thiolase or an acetyl-CoA acetyltransferase activity, a hydroxybutyryl-CoA dehydrogenase activity, a crotonase activity, a crotonyl-CoA reductase or a butyryl-CoA dehydrogenase, and an alcohol dehydrogenase. In another embodiment, the pathway produces n-butanol and comprises one or more enzymes that convert acetyl-CoA to malonyl-CoA, malonyl-CoA to Acetoacetyl-CoA, and at least one enzyme that converts (a) acetoacetyl-CoA to (R)- or (S)-3-hydroxybutyryl-CoA and (R)- or (S)-3-hydroxybutyryl-CoA to crotonyl-CoA, crotonyl-CoA to butyryl-CoA, butyryl-CoA to butyraldehyde and butyraldehyde to 1-butanol. In a further embodiment, the pathway an acetyl-CoA carboxylase and an acetoacetyl-CoA synthase and one or more enzymes selected from the group consisting of (a) hydroxybutyryl CoA dehydrogenase, (b) crotonase, (c) trans-2-enoyl-CoA reductase, and (d) an alcohol/aldehyde dehydrogenase.

For industrial applications, the carbon utilization pathway of the disclosure can be used to improve carbon yield in the production of fuels and chemicals derived from acetyl-CoA, such fuels including, but not limited to, acetate, n-butanol, isobutanol, ethanol, biodiesel and the like. For example, if additional reducing power such as hydrogen or formic acid is provided, the carbon utilization pathway of the disclosure can be used to produce compounds that are more reduced than the substrate, for example, ethanol, 1-butanol, isoprenoids, and fatty acids from sugar.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 1A-D shows four variations of methanol elongation cycle (MEC) converting methanol to acetyl-phosphate (AcP) and then further to 1-butanol. Also shows in a table corresponding to the abbreviations used in each of (A)-(D). (A) MEC involving hps and phi activity. (B) MEC involving das and fsa activity. (C) MEC involving hps, phi and an xpk/tkt activity. (D) MEC involving a das, fsa, and xpk/tkt activity. Other abbreviations are: F6P, fructose 6-phosphate; E4P, erythrose-4-phosphate; G3P, glyceraldehyde 3-phosphate; DHAP, dihydroxyacetone phosphate; X5P, xylulose 5-phosphate; R5P, ribose 5-phosphate; Ru5P, ribulose 5-phosphate; S7P, sedoheptulose 7-phosphate; Tal, transaldolase, Tkt, transketolase; Rpi, ribose-5-phosphate isomerase; Rpe, ribulose-5-phosphate 3-epimerase; Fpk, Fructose-6-phosphoketolase; Xpk, Xylulose-5-phosphoketolase; Mdh, Methanol dehydrogenase; Hps, hexulose-6-phosphate synthase; Phi, Hexulose-6-phosphate isomerase; Das, dihydroxyacetone synthase; Fsa, Fructose-6-phosphate aldolase; Pta, Phosphotransacetylase; and Ack, acetate kinase.

FIG. 12A-C shows Conversion of methanol to higher n-alcohols. (A) The MCC is the combination of RuMP with NOG that bypasses ATP dependency. See Table B for details. (B) The major MCC mode uses the more active X5P-phosphoketolase (Xpk). (C) The minor MCC mode can achieve the same result with the less active F6P-phosphoketolase (Fpk).

FIG. 13A-C shows simulation and in vitro demonstration of a kinetic trap (A) Ensemble Model Robustness Analysis (EMRA) of the core MCC pathway. YR,M is the fraction of robust models constrained to a steady state. The variation of phosphoketolase is shown in red and variation of transaldolase in blue. (B) Simulated distribution of acetic acid isotopes using $^{13}$C-formaldehyde as the substrate (C) In vitro production of acetic acid and GC-MS analysis using $^{13}$C-formaldehyde as substrate. Seven enzymes (Hps, Phi, Tkt, Tal, Rpe, Rpi, and F/Xpk) were used to produce acetyl-phosphate from $^{13}$C-formaldehyde. For GC analysis, the AcP was then converted to acetate by acetate kinase using ATP recycling by glucokinase. An acetate standard curve was established with R2=0.998 up to 5 mM to ensure reliable quantitation. Assays were independently run in triplicate (N=3) with error bars representing standard deviation.

FIG. 14A-C shows $^{13}$C Tracing from $^{13}$C-Formaldehyde and Formate to Ethanol. (A) The mass spectra of all four ethanol isotopes including unlabeled ethanol, [1-$^{13}$C]-ethanol, [2-$^{13}$C]-ethanol, double labeled [1,2-$^{13}$C]-ethanol. All spectra were normalized to the most abundant internal peak. Only double labeled ethanol has a significant 48 ion (asterisks). (B) Mass spectrum of ethanol experimentally produced from 13C-formaldehyde, unlabeled formate, and unlabeled R5P using the full MCC pathway with formate dehydrogenase. The assays were analyzed after two hours at room temperature. Formate was oxidized to $CO_2$ by formate dehydrogenase to provide the necessary NADH to reduce acetyl-CoA to ethanol. (C) The "No Tal" control contained the same conditions as the full pathway except for omitting transaldolase. No 48 ion was detected for the control.

FIG. 15A-D shows ethanol and n¬-butanol production from formaldehyde or methanol using MCC. (A) Steady state production of ethanol from formaldehyde with MCC using formic acid as electron source. 6 mM formaldehyde, 10 mM formate, and 0.5 mM R5P were added at the zero, one, and two hour points. (B) Sugar phosphate measurement over time using HPIC-PAD for the batch conversion of formaldehyde to acetyl-phosphate. Most of the carbon rearrangement occurred within the first minute. F6P and R5P standards overlap so the combine area is provided in the full assay. (C) Conversion of methanol to ethanol and (D) to n-butanol over 24 hours. The productivity drops after five hours, likely due to instability of intermediates. The alcohol production assays were independently run in triplicate. Methanol consumption (for full assay only) is shown in red circles, while ethanol and n-butanol production is shown with diamonds. Blue colors indicates the full MCC pathway while green illustrates the "No Tal" control. Assays were independently run in triplicate (N=3) with error bars representing standard deviation.

FIG. 16 shows a schematic of natural and synthetic pathways for the conversion of methanol to n-butanol. The RuMP and DHA pathways result in a carbon loss from pyruvate decarboxylation. The Serine pathway requires ATP input which lowers the carbon yield due to oxidative phosphorylation. MCC is the only theoretical route that can achieve stoichiometric conversion with amenable enzymes.

FIG. 17A-B shows Methanol Assimilation variations. (A) Three classes of enzymes that oxidize methanol to formaldehyde. Only NAD-Dependent Mdh produces the reduced NADH cofactor for acetyl-CoA reduction. (B) Two equivalent routes for the assimilation of formaldehyde to fructose-6-phosphate. Fsa is a recently discovered enzyme that is not known to participate in any metabolic pathway. The Hps-Phi route was chosen for the cell-free systems since it has better kinetics (significantly lower Km for substrates).

DETAILED DESCRIPTION

Figure 2:
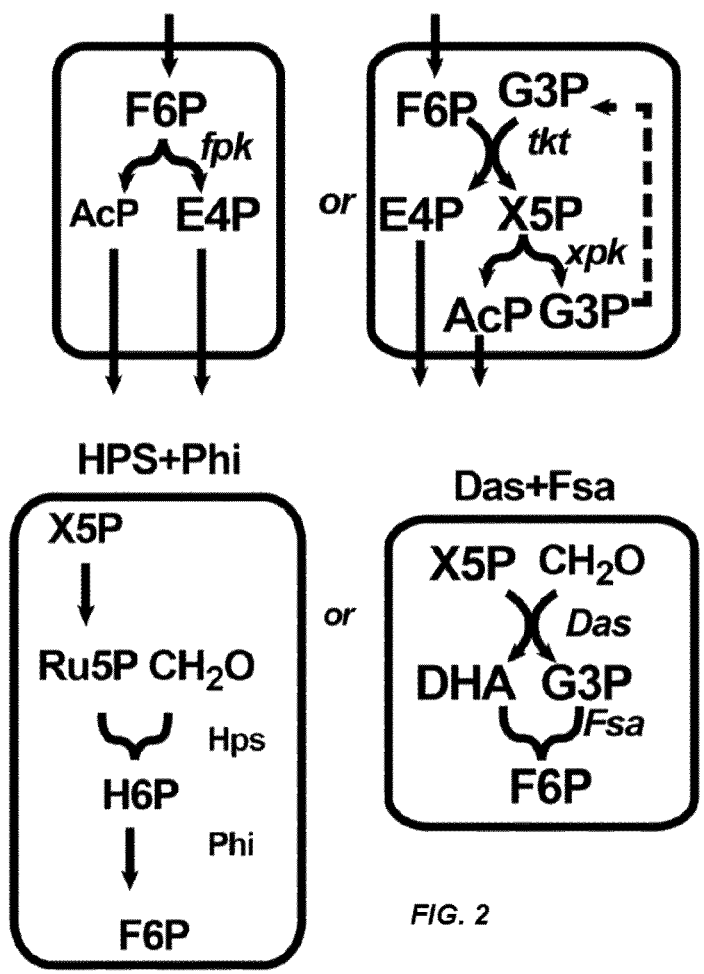
FIG. 2 shows pathways depicting formaldehyde assimilation. Formaldehyde assimilation to F6P can be accomplished by the RuMP enzymes: hps and phi. It can also be accomplished using a modified version of the DHA pathway; das and fsa can also convert a pentose phosphate and formaldehyde to F6P. Phosphoketolase are known to be able to have X5P or dual F6P/X5P activity. When combined with transketolase, these two variants of phosphoketolase are logically identical.
Figure 3:
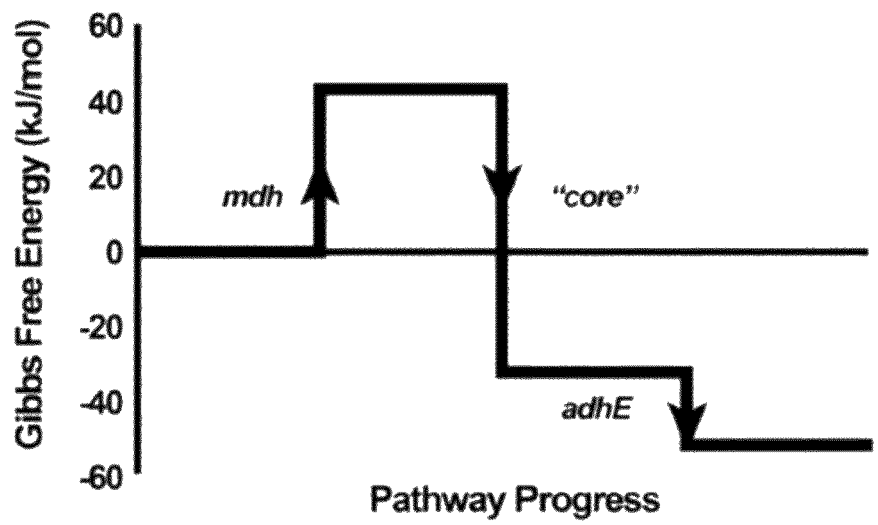
FIG. 3 is a graph depicting the thermodynamics of MEC. The initial oxidization of methanol to formaldehyde provides the main thermodynamic hurdle. However, the core portion of MEC (the conversion of two formaldehydes to AcCoA) is very thermodynamically favorable. The final sequential reduction of acetyl-CoA to ethanol is also thermodynamically favorable. Values were generated using the eQuilibrator website using pH=7.5 and ionic strength at 0.2 Molar.
Figure 4:
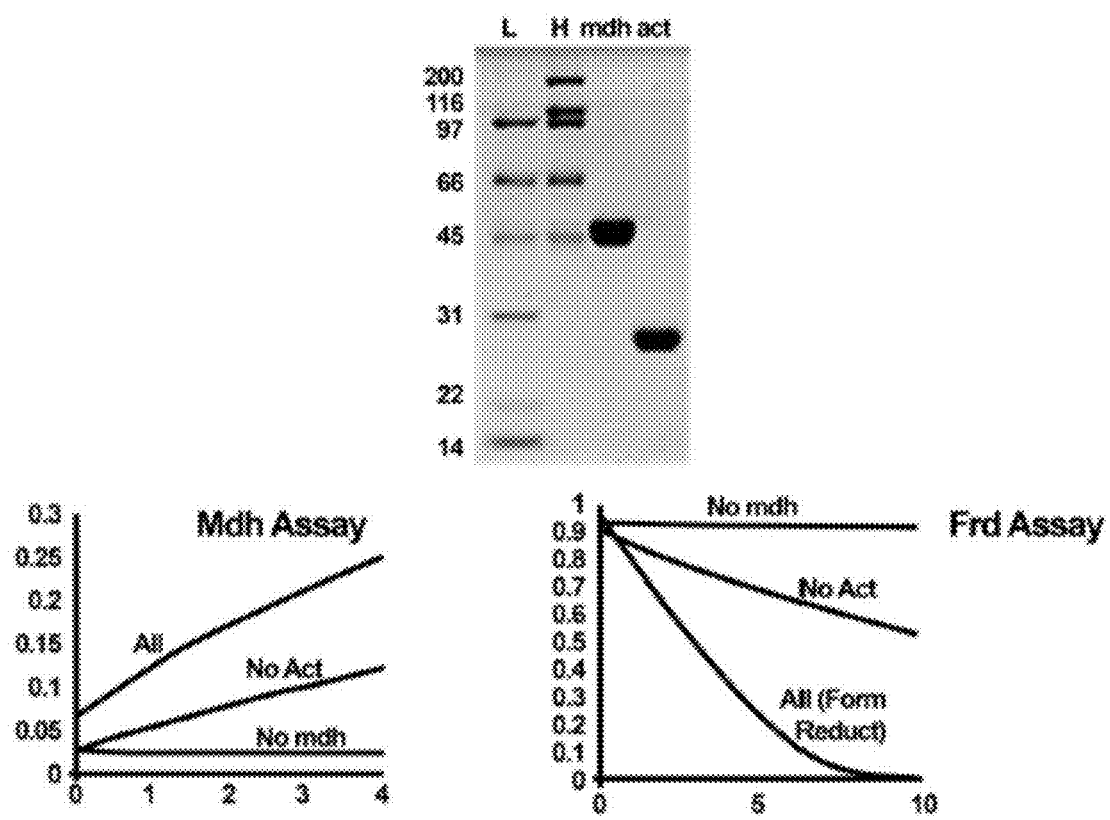
FIG. 4 shows and assay for methanol oxidation. The methanol dehydrogenase gene form Bacillus methanolicus is known to be activated by a specific activator production (termed Act). Here, the same enzyme can catalyze the oxidation of methanol and the reduction of formaldehyde using NAD or NADH, respectively. The oxidation of methanol is much slower than the reverse direction, and is driven by large concentration of substrate (500 mM methanol) and quick elimination of product (formaldehyde).
Figure 5:
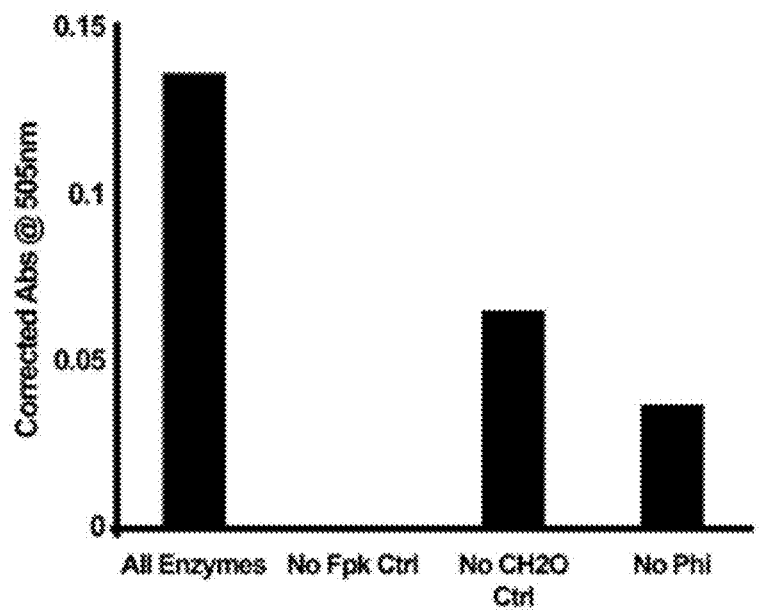
FIG. 5 is a graph showing the in vitro conversion of 2 formaldehydes to acetyl-phosphate. The in vitro conversion of formaldehyde to acetyl-phosphate using the MEC enzymes was measured by the hydroxamate method. An initial amount of R5P was added to start the cycle, with excess amounts of formaldehyde. When all the MEC enzymes were added, a significantly higher conversion to acetyl-phosphate was achieved as compared with the controls.

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Methylotrophs are microorganisms capable of assimilating methanol into higher carbon molecules essential for cellular growth, such as acetyl-CoA. In the known methylotrophic pathways, methanol is first oxidized to formaldehyde. Formaldehyde can then be assimilated by one of several possible routes such as the RuMP, DHA, or serine pathway. These pathways allow formaldehyde to be converted to sugar-phosphates or pyruvate, which can then feed into central metabolism. However, in the native conversion of methanol to acetyl-CoA, carbon dioxide is always inevitably lost during the decarboxylation of pyruvate.

The disclosure provides methods and compositions to avoid this problem in carbon management, by using a recombinant metabolic pathway to bypass pyruvate oxidation to stoichiometrically convert two methanols into acetyl-CoA. This pathway, termed Methanol Elongation Cycle (MEC), is able to condense two methanol molecules to acetyl-CoA using a series of well-established enzymes. The acetyl-CoA can then be used in a number of pathways, such as the production of bio-alcohol. In the case of 1-butanol production from methanol, the overall pathway is thermodynamically favorable, ATP-independent, and redox balanced. This pathway represents at 50% improvement in carbon balance over existing pathways and can be used in the conversion of methanol to higher-chain liquid fuels and chemicals.

The disclosure provides methods and compositions (including cell free systems and recombinant organisms) that provide improved carbon yield compared to naturally occurring methanol utilization pathways. By "improved carbon yield" means that the process results in a conversion of methane, methanol, or formaldehyde to acetyl-phosphate with minimal to no carbon loss (e.g., loss as $CO_2$).

It should be recognized that the disclosure describes the pathway in various embodiments and is schematically depicted in FIG. 1 as well as described throughtout the specification. It will be further recognized that the oxidative metabolism may occur after production of acetyl-phosphate of FIG. 1.

In the pathways shown in, e.g., FIG. 1 methanol is the input molecule; however, methane and formaldehyde (among others) may also be used in the pathway. A methanol dehydrogenase is used to initiate the metabolism of methanol to acetyl-phosphate. The pathway uses investment of 5 carbon sugar phosphates such as, for example, ribulose-5-phosphate or xylulose-5-phosphate, which reacts with $CH_2O$ to begin a series of reactions involved in non-oxidative carbon rearrangement to regenerate the 5-carbon sugar phosphates and produced acetyl-phosphate. MEC can proceed with a fructose-6-phosphoketolase (Fpk), a xylulose-5-phosphoketolase (Xpk) or bifunctional enzymes that contain both activities. Because of the flexibility of MEC, the pathway can proceed with different combinations of Fpk, or Xpk and transketolase (Tkt), or with different sugar phosphates as the starting molecule. In all these pathways, MEC converts the combination of sugar phosphates and methanol, methane or formaldehyde to AcP without or with minimal carbon loss. Acetyl-phosphate (AcP) can then be converted to acetyl-CoA by acetyltransferase (Pta, Pta variant or homolog thereof), or to acetate by acetate kinase (Ack, Ack variant or homolog thereof). Acetyl-CoA can be converted to alcohols, fatty acids, or other products if additional reducing power is provided. When producing acetyl phosphate from methanol, the MEC pathway converts 4 methanol to 2 acetyl phosphates.

The disclosure provides an in vitro method of producing acetyl-phosphate, acetyl-CoA and chemicals and biofuels that use acetyl-CoA as a substrate. In this embodiment, of the disclosure cell-free preparations can be made through, for example, three methods. In one embodiment, the enzymes of the MEC pathway, as described more fully below and throughout, are purchased and mixed in a suitable buffer and a suitable substrate(s) (e.g., MeOH or formaldehyde) is added and incubated under conditions for acetyl-phosphate production. In some embodiments, the enzyme can be bound to a support or expressed in a phage display or other surface expression system and, for example, fixed in a fluid pathway corresponding to points in the MEC cycle.

In another embodiment, one or more polynucleotides encoding one or more enzymes of the MEC pathway are cloned into one or more microorganism under conditions whereby the enzymes are expressed. Subsequently the cells are lysed and the lysed preparation comprising the one or more enzymes derived from the cell are combined with a suitable buffer and substrate (and one or more additional enzymes of the MEC pathway, if necessary) to produce acetyl-phosphate from the substrate. Alternatively, the enzymes can be isolated from the lysed preparations and then recombined in an appropriate buffer. In yet another embodiment, a combination of purchased enzymes and expressed enzymes are used to provide a MEC pathway in an appropriate buffer. In one embodiment, heat stabilized polypeptide/enzymes of the MEC pathway are cloned and expressed. In one embodiment, the enzymes of the MEC pathway are derived from thermophilic microorganisms. The microorganisms are then lysed, the preparation heated to a temperature wherein the heat stabilized polypeptides of the MEC cycle are active and other polypeptides (not of interest) are denatured and become inactive. The preparation thereby includes a subset of all enzymes in the microorganism and includes active heat-stable MEC enzymes. The preparation can then be used to carry out the MEC cycle to produce acetyl phosphate.

For example, to construct an in vitro system, all the MEC enzymes can be acquired commercially or purified by affinity chromatography or expressed by phage or bound to a substrate or any combination of the foregoing, tested for activity, and mixed together in a properly selected reaction buffer. The system is ATP- and redox-independent and comprises 5, 6 or 7 enzymatic steps that include the following enzymes: (i) a methanol dehydrogenase (e.g., Mdh, or homolog thereof) and/or an alcohol oxidase (e.g., Aox, or homolog thereof); (ii) an hexulose-6-phosphate synthase (e.g., Hps, or homolog thereof) and a hexulose-6-phosphate isomerase (Phi, or homolog thereof), or a dihydroxyacetone synthase (Das, or homolog thereof) and fructose-6-phasphate aldolase (Fsa, or homolog thereof); (iii) a fructose-6-phosphate phosphoketolase (Fpk, or homolog thereof), or a xylulose-6-phosphate phosphoketolase (Xpk, or homolog thereof) and a transketolase (Tkt, or homolog thereof); (iv) a ribose-5-phosphate isomerase (Rpi, or homolog thereof); (v) a transketolase (Tkt, or homolog thereof)); and (vi) a transaldolase (Tal, or homolog thereof). Note that "(i)" is optional and can be used if the starting carbon source is, for example, methanol, but is not necessary if the starting material is, for example, formaldehyde.

Using this in vitro system comprising the foregoing 5 or 6 enzymatic steps an initial amount of 4 moles of a C1 carbon source (e.g., methanol) can be converted to 2 moles of AcP (within error) at room temperature after about 1.5 hours. The in vitro system can be carried out as a single stage reaction, fluid flow system or as a batch processing system.

To extend the production further to acetate, Ack can be added to the in vitro MEC system. Alternatively, to extend the production to acetyl-coA, Pta can be added to the in vitro MEC system.

An in vivo system is also provided using the foregoing enzymes in a biosynthetic pathway engineered into a microorganism to obtain a recombinant microorganism.

The disclosure also provides recombinant organisms comprising metabolically engineered biosynthetic pathways that comprise a non-$CO_2$ ATP independent pathway for the production of acetyl-phosphate, acetyl-CoA and/or products derived therefrom.

In one embodiment, the disclosure provides a recombinant microorganism comprising elevated expression of at least one target enzyme as compared to a parental microorganism or encodes an enzyme not found in the parental organism. In another or further embodiment, the microorganism comprises a reduction, disruption or knockout of at least one gene encoding an enzyme that competes with a metabolite necessary for the production of a desired metabolite or which produces an unwanted product. The recombinant microorganism produces at least one metabolite involved in a biosynthetic pathway for the production of, for example, acetyl-phosphate and/or acetyl-CoA. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of, for example, acetyl-phosphate and/or acetyl-CoA. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure. In another embodiment, the polynucleotide encoding the desired target enzyme is naturally occurring in the organism but is recombinantly engineered to be overexpressed compared to the naturally expression levels.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) *Cyanobacteria*, e.g., oxygenic phototrophs; (4) *Spirochetes* and related species; (5) *Planctomyces*; (6) *Bacteroides, Flavobacteria*; (7) *Chlamydia*; (8) Green sulfur bacteria; (9) Green non-sulfur bacteria (also anaerobic phototrophs); (10) *Radioresistant micrococci* and relatives; and (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products (e.g., enzymes or polypeptides) belong to the same "metabolic pathway" if they, in parallel or in series, act on the same substrate, produce the same product, or act on or produce a metabolic intermediate (i.e., metabolite) between the same substrate and metabolite end product. The disclosure provides recombinant microorganism having a metabolically engineered pathway for the production of a desired product or intermediate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. In an illustrative embodiment, the introduction of genetic material into a parental microorganism results in a new or modified ability to produce acetyl-phosphate and/or acetyl-CoA through a non-$CO_2$ evolving and/or non-oxidative pathway for optimal carbon utilization. The genetic material introduced into the parental microorganism contains gene(s), or parts of gene(s), coding for one or more of the enzymes involved in a biosynthetic pathway for the production of acetyl-phosphate and/or acetyl-CoA, and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products).

An "enzyme" means any substance, typically composed wholly or largely of amino acids making up a protein or polypeptide that catalyzes or promotes, more or less specifically, one or more chemical or biochemical reactions.

A "protein" or "polypeptide", which terms are used interchangeably herein, comprises one or more chains of chemical building blocks called amino acids that are linked together by chemical bonds called peptide bonds. A protein or polypeptide can function as an enzyme.

As used herein, the term "metabolically engineered" or "metabolic engineering" involves rational pathway design and assembly of polypeptides having a desired activity, biosynthetic genes, genes associated with operons, and/or control elements of such polynucleotides, for the production of a desired metabolite, such as an acetyl-phosphate and/or acetyl-CoA, higher alcohols or other chemical, in vitro or in a microorganism. "Metabolically engineered" can further include optimization of metabolic flux by regulation cofactors, particular reaction conditions, optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., methanol, methane, formaldehyde etc.), an intermediate in (e.g., acetyl-coA), or an end product (e.g., 1-butanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e., a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a phosphoketolase. This microorganism can act as a parental microorganism in the generation of a microorganism modified to express or over-express a second target enzyme e.g., a transaldolase. In turn, that microorganism can be modified to express or over express e.g., a transketolase and a ribose-5 phosphate isomerase, which can be further modified to express or over express a third target enzyme, e.g., a ribulose-5-phosphate epimerase. As used herein, "express" or "over-express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules into the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme into a parental microorganism.

Polynucleotides that encode enzymes useful for generating metabolites (e.g., enzymes such as phosphoketolase, transaldolase, transketolase, ribose-5-phosphate isomerase, ribulose-5-phosphate epimerase) including homologs, variants, fragments, related fusion proteins, or functional equivalents thereof, are used in recombinant nucleic acid molecules that direct the expression of such polypeptides in appropriate host cells, such as bacterial or yeast cells.

The sequence listing appended hereto provide exemplary polynucleotide sequences encoding polypeptides useful in the methods described herein. It is understood that the addition of sequences which do not alter the encoded activity of a nucleic acid molecule, such as the addition of a non-functional or non-coding sequence (e.g., polyHIS tags), is a conservative variation of the basic nucleic acid.

It is understood that a polynucleotide described herein include "genes" and that the nucleic acid molecules described above include "vectors" or "plasmids." For example, a polynucleotide encoding a phosphoketolase can comprise an Fpk gene or homolog thereof, or an Xpk gene or homolog thereof, or a bifunctional F/Xpk gene or homolog thereof. Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

The term "polynucleotide," "nucleic acid" or "recombinant nucleic acid" refers to polynucleotides such as deoxyribonucleic acid (DNA), and, where appropriate, ribonucleic acid (RNA).

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not necessarily pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

The term "recombinant microorganism" and "recombinant host cell" are used interchangeably herein and refer to microorganisms that have been genetically modified to express or over-express endogenous polynucleotides, or to express non-endogenous sequences, such as those included in a vector. The polynucleotide generally encodes a target enzyme involved in a metabolic pathway for producing a desired metabolite as described above, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway associated with a metabolically engineered microorganism as described herein. With respect to the MEC pathway described herein, a starting material can be any suitable carbon source (e.g., C1 carbon sources) including, but not limited to, methanol, methane, formaldehyde etc. Methanol, for example, can be converted to formaldehyde prior to entering the MEC pathway as set forth in FIG. 1.

"Transformation" refers to the process by which a vector is introduced into a host cell. Transformation (or transduction, or transfection), can be achieved by any one of a number of means including electroporation, microinjection, biolistics (or particle bombardment-mediated delivery), or agrobacterium mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous". For example, tktB is an isozyme of tktA, talA is an isozyme of talB and rpiB is an isozyme of rpiA.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers for various genes, homologs and variants useful in the generation of synthetic pathways and/or recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web. Such homologs and variants can be identified by merely performing a BLAST search using a reference sequence from the present disclosure. For example, a BLAST search of SEQ ID NO:1 yielded 75+ related sequences within 20 seconds of performing the search, with identity ranging from 40% to 100%.

Culture conditions suitable for the growth and maintenance of a recombinant microorganism provided herein are known (see, e.g., "Culture of Animal Cells—A Manual of Basic Technique" by Freshney, Wiley-Liss, N.Y. (1994), Third Edition). The skilled artisan will recognize that such conditions can be modified to accommodate the requirements of each microorganism. Appropriate culture conditions useful in producing a acetyl-phosphate, acetyl-CoA or other metabolites derived therefrom including, but not limited to 1-butanol, n-hexanol, 2-pentanone and/or octanol products comprise conditions of culture medium pH, ionic strength, nutritive content, etc.; temperature; oxygen/$CO_2$/nitrogen content; humidity; light and other culture conditions that permit production of the compound by the host microorganism, i.e., by the metabolic action of the microorganism. Appropriate culture conditions are well known for microorganisms that can serve as host cells.

It is understood that a range of microorganisms can be modified to include a recombinant metabolic pathway or for the production of enzymes for use in a pathway suitable for the production of n-butanol, n-hexanol and octanol. It is also understood that various microorganisms can act as "sources" for genetic material encoding target enzymes suitable for use in a recombinant microorganism provided herein.

The disclosure provides methods for the heterologous expression of one or more of the biosynthetic genes or polynucleotides involved in acetyl-phosphate synthesis, acetyl-CoA biosynthesis or other metabolites derived therefrom and recombinant DNA expression vectors useful in the method. Thus, included within the scope of the disclosure are recombinant expression vectors that include such nucleic acids.

Recombinant microorganisms provided herein can express a plurality of target enzymes involved in pathways for the production of acetyl-phosphate, acetyl-CoA or other metabolites derived therefrom from a suitable carbon substrate such as, for example, methanol, methane, formaldehyde and the like. The carbon source can be metabolized to, for example, a desirable sugar phosphate that is metabolized in the MEC pathway of the disclosure. Sources of methanol, methane and formaldehyde are known. Of particular interest is methane gas, which occurs in nature and is a common by-product of waste degradation.

The disclosure demonstrates the production of acetyl-phosphate and other chemicals by (i) the expression or over expression of one or more heterologous polynucleotide or over-expression of one or more native polynucleotides or (ii) the use of products of such expressed polynucleotide in an in vitro system, encoding (i) a polypeptide that catalyzes the production of acetyl-phosphate and erythrose-4-phosphate (E4P) from Fructose-6-phosphate; (ii) a polypeptide that catalyzes the conversion of fructose-6-phosphate and E4P to sedoheptulose 7-phosphate (S7P) and glyceraldehyde-3-phosphate (G3P); (iii) a polypeptide the catalyzes the conversion of S7P to ribose-5-phosphate and xylulose-5-phosphate; (iv) a polypeptide that catalyzes the conversion of ribose-5-phosphate to ribulose-5-phosphate; (v) a polypeptide the catalyzes the conversion of ribulose-5-phosphate to xylulose-5-phosphate; (vi) a polypeptide that converts fructose 1,6-biphosphate to fructose-6-phosphate; (vii) a polypeptide that converts ribulose-5-phosphate and formaldehyde to hexulose-6-phosphate; (viii) a polypeptide that converts hexulose-6-phosphate to fructose-6-phosphate; (ix) a polypeptide that converts xylulose-5-phosphate and formaldehyde to dihydroxyacetone and glyceraldehyde-3-phosphate; and (x) a polypeptide that converts dihydroxyacetone and glyceraldehyde-3-phosphate to fructose-6-phosphate. Optionally the recombinant microorganism or pathway may further include a polypeptide that converts methanol to formaldehyde; a polypeptide that converts acetyl-phosphate to acetyl-coA, and/or acetyl-coA to 1-butanol. For example, the disclosure demonstrates that with expression of a heterologous Fpk/Xpk genes in *Escherichia* (e.g., *E. coli*) the production of acetyl-phosphate, acetyl-CoA or other metabolites derived therefrom can be obtained.

Microorganisms provided herein are modified to produce metabolites in quantities and utilize carbon sources more effectively compared to a parental microorganism. In particular, the recombinant microorganism comprises a metabolic pathway for the production of acetyl-phosphate that conserves carbon. By "conserves carbon" is meant that the metabolic pathway that converts a sugar phosphate to acetyl-phosphate has a minimal or no loss of carbon from the starting sugar phosphate to the acetyl-phosphate. For example, in one embodiment, the recombinant microorganism produces a stoichiometrically conserved amount of carbon product from the same number of carbons in the input carbon source (e.g., 2 methanol yields 1 acetyl-phosphate).

Accordingly, the disclosure provides a recombinant microorganisms or in vitro pathway that produce acetyl-phosphate, acetyl-CoA or other metabolites derived therefrom and includes the presence of, expression or elevated expression of target enzymes such as a phosphoketolase (e.g., Fpk, Xpk, or Fpk/Xpk, or homologs thereof), a transaldolase (e.g., Tal), a transketolase (e.g., Tkt, or homologs thereof), ribose-5-phosphate isomerase (e.g., Rpi, or homologs thereof), a ribulose-5-phosphate epimerase (e.g., Rpe, or homologs thereof), a hexulose-6-phosphate synthase (e.g., Hps, or homologs thereof), a hexulose-6-phosphate isomerase (e.g., Phi, or homologs thereof), a dihydroxyacetone synthase (e.g., Das, or homologs thereof), a fructose-6-phosphate aldolase (e.g., Fsa, or homologs thereof), a methanol dehydrogenase (e.g., Mdh, or homologs thereof), an alcohol oxidase (Aox, or homologs thereof), or any combination thereof, as compared to a parental microorganism. In some embodiments, where an acetyl-phosphate product is to be further metabolized, the recombinant microorganism or in vitro pathway can include, express or over express a phosphotransacetylase (e.g., pta), and alternatively or optionally may include or express or over express an acetate kinase. In addition, the microorganism may include a disruption, deletion or knockout of expression of an alcohol/acetoaldehyde dehydrogenase that preferentially uses acetyl-coA as a substrate (e.g. adhE gene, or homologs thereof), as compared to a parental microorganism. In some embodiments, further reductions in activity or expression or knockouts may include one or more enzymes selected from the group consisting of a lactate dehydrogenase (e.g., ldh, or homologs thereof), a fumarate reductase (frdBC, or homologs thereof), an alcohol dehydrogenase (AdhE, or homologs thereof), acetate kinase (AckA or homologs thereof), pyruvate lyase (pflB, or homologs thereof), glyceraldehyde-3-phosphate dehydrogenase (gapA, or homologs thereof), formaldehyde dehydrognase (frmA from *E. coli* accession number HG738867, or homologs thereof such as *P. putida*-Acc. #CP005976; *K. pneumoniae*-Acc. #D16172; *D. dadantii*-Acc. #CP001654 and *P. stutzeri*-Acc. #CP003677) and S-formylglutathione hydrolase (frmB/yeiG, or homologs thereof). When the microorganism is a yeast microorganism such reductions in expression or knockouts include one or more selected from the group consisting of pyruvate decarboxylase (PDC1, PDC5, PDC6 or homologs thereof), glyceraldehyde-3-phosphate dehydrogenase (TDH1, TDH2, TDH3, or homologs thereof), formaldehyde dehydrogenase (SFA1, or homologs thereof), and S-formylglutathione hydrolase (YJL068C, or homolog thereof). It will be recognized that organism that inherently have one or more (but not all) of the foregoing enzymes can be utilized as a parental organism. As described more fully below, a microorganism of the disclosure comprising one or more recombinant genes encoding one or more enzymes above, may further include additional enzymes that extend the acetyl-phosphate product to acetyl-CoA, which can then be extended to produce, for example, butanol, isobutanol, 2-pentanone and the like.

Figure 6:
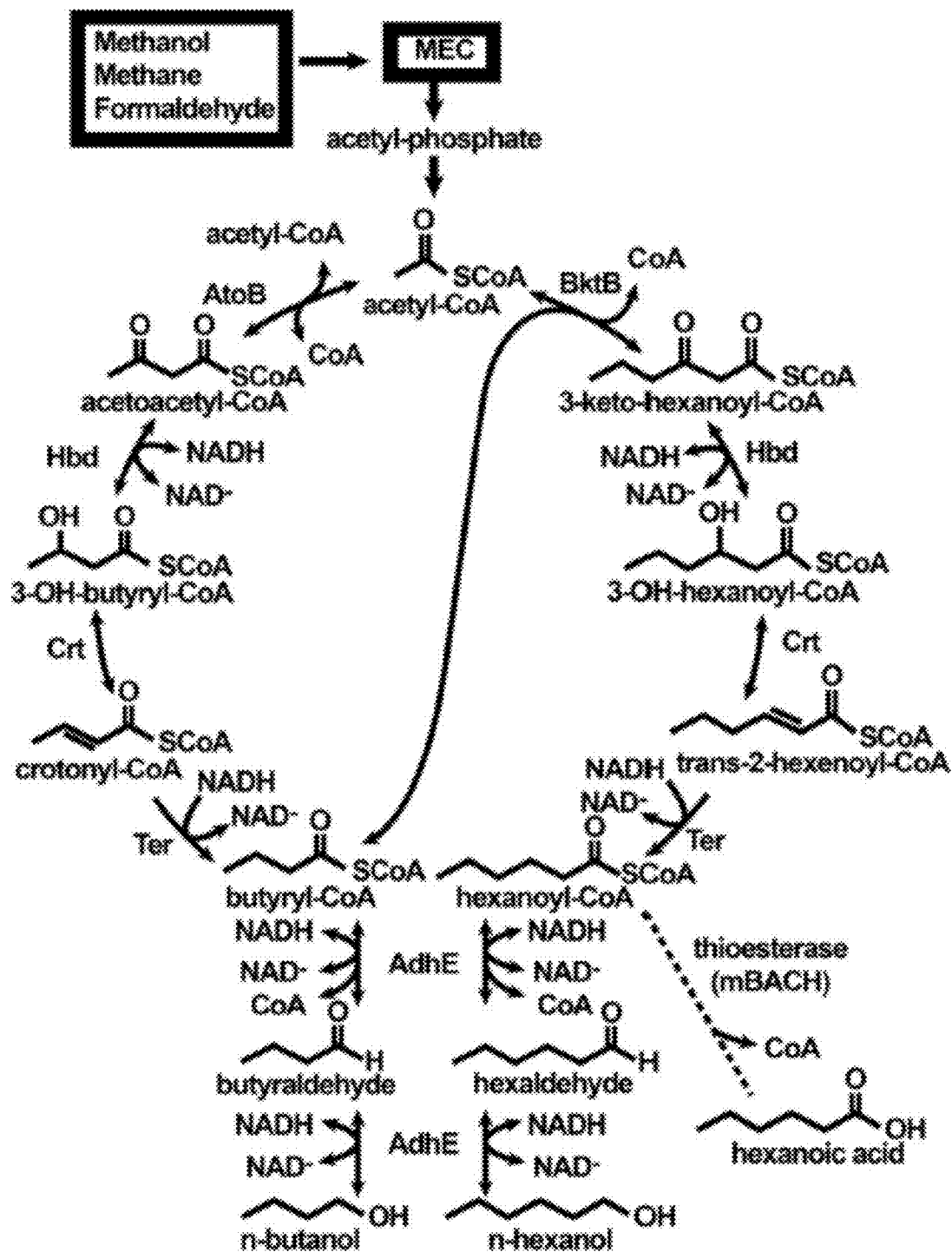
FIG. 6 show general schemes depicting MEC and additional products that can be formed following production of acetyl-phosphate by the MEC pathway.
Figure 7:
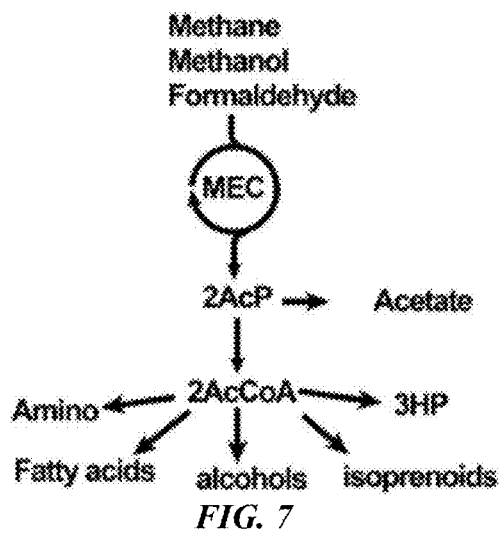
FIG. 7 show general schemes depicting MEC and additional products that can be formed following production of acetyl-phosphate by the MEC pathway.

Accordingly, a recombinant microorganism or in vitro pathway provided herein includes the presence of or the elevated expression of at least one target enzyme, such as FpK, Xpk, or F/Xpk, or homologs thereof. In other embodiments, a recombinant microorganism can express a plurality of target enzymes involved in a pathway to produce acetyl-phosphate, acetyl-CoA or other metabolites derived therefrom as depicted in FIGS. 1, 6 and 7 from a carbon source such as methanol, methane, formaldehyde and the like. In one embodiment, the recombinant microorganism or in vitro pathway comprises enzymes, expression of a heterologous or over expression of an endogenous enzyme selected from a phosphoketolase and either (i) hexulose-6-phosphate synthase and hexulose-6-phosphate isomerase, or (ii) a dihydroxyacetone synthase and a fructose-6-phosphate aldolase.

In another embodiment, the microorganism or pathway includes, expresses or overexpress a transketolase (Tkt) and/or a transaldolase (Tal).

As previously noted, the target enzymes described throughout this disclosure generally produce metabolites. In addition, the target enzymes described throughout this disclosure are encoded by polynucleotides. For example, a fructose-6-phosphoketolase can be encoded by an Fpk gene, polynucleotide or homolog thereof. The Fpk gene can be derived from any biologic source that provides a suitable nucleic acid sequence encoding a suitable enzyme having fructose-6-phosphoketolase activity.

Accordingly, in one embodiment, a recombinant microorganism provided herein includes expression of a fructose-6-phosphoketolase (Fpk) as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes acetyl-phosphate and E4P from fructose-6-phosphate. The fructose-6-phosphoketolase can be encoded by an Fpk gene, polynucleotide or homolog thereof. The Fpk gene or polynucleotide can be derived from *Bifidobacterium adolescentis*.

Phosphoketolase enzymes (F/Xpk) catalyze the formation of acetyl-phosphate and glyceraldehyde 3-phosphate or erythrose-4-phosphate from xylulose 5-phosphate or fructose 6-phosphate, respectively. For example, the *Bifidobacterium adolescentis* Fpk and Xpk genes or homologs thereof can be used in the methods of the disclosure.

In addition to the foregoing, the terms "phosphoketolase" or "F/Xpk" refer to proteins that are capable of catalyzing the formation of acetyl-phosphate and glyceraldehyde 3-phosphate or erythrose-4-phosphate from xylulose 5-phosphate or fructose 6-phosphate, respectively, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:2. Additional homologs include: *Gardnerella vaginalis* 409-05 ref|YP_003373859.1|having 91% identity to SEQ ID NO:2; *Bifidobacterium breve* ref|ZP_06595931.1|having 89% to SEQ ID NO:2; *Cellulomonas fimi* ATCC 484 YP_004452609.1 having 55% to SEQ ID NO:2; *Methylomonas methanica* YP_004515101.1 having 50% identity to SEQ ID NO:2; and *Thermosynechococcus elongatus* BP-1] NP_681976.1 having 49% identity to SEQ ID NO:2. The sequences associated with the foregoing accession numbers are incorporated herein by reference.

In another embodiment, a recombinant microorganism provided herein includes elevated expression of methanol dehydrogenase (Mdh) as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes formaldehyde from a substrate that includes methanol. The methanol dehydrogenase can be encoded by an Mdh gene, polynucleotide or homolog thereof. The Mdh gene or polynucleotide can be derived from various microorganisms including *B. methanolicus*.

In addition to the foregoing, the terms "methanol dehydrogenase" or "Mdh" refer to proteins that are capable of catalyzing the formation of formaldehyde from methanol, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:4.

As an alternative, or in addition to a methanol dehydrogenase, the microorganism can be include heterologous expression or over expression of an endogenous alcohol oxidase. Alcohol oxidase converts a primary alcohol (e.g., methanol) to an aldehyde (e.g., formaldehyde). This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes formaldehyde from a substrate that includes methanol. The alcohol oxidase can be encoded by an Aox gene, polynucleotide or homolog thereof. The Aox gene or polynucleotide can be derived from various microorganisms including *Pichia pastoris*.

In addition to the foregoing, the terms "alcohol oxidase" or "Aox" refer to proteins that are capable of catalyzing the formation of formaldehyde from a primary alcohol (e.g., methanol), and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:22.

In another embodiment, a recombinant microorganism provided herein includes elevated expression of ribulose-5-phosphate-3=epimerase (also referred to as ribulose-5-phosphate epimerase or ribulose-3-phosphate epimerase) as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes xylulose 5-phosphate from a substrate that includes ribulose 5-phosphate. The ribulose-5-phosphate epimerase can be encoded by an Rpe gene, polynucleotide or homolog thereof. The Rpe gene or polynucleotide can be derived from various microorganisms including *E. coli*.

In addition to the foregoing, the terms "ribulose 5-phosphate epimerase" or "Rpe" refer to proteins that are capable of catalyzing the formation of xylulose 5-phosphate from ribulose 5-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:6. Additional homologs include: *Shigella boydii* ATCC 9905 ZP_11645297.1 having 99% identity to SEQ ID NO:6; *Shewanella loihica* PV-4 YP_001092350.1 having 87% identity to SEQ ID NO:6; *Nitrosococcus halophilus* Nc4 YP_003526253.1 having 75% identity to SEQ ID NO:6; *Ralstonia eutropha* JMP134 having 72% identity to SEQ ID NO:6; and *Synechococcus* sp. CC9605 YP_381562.1 having 51% identity to SEQ ID NO:6. The sequences associated with the foregoing accession numbers are incorporated herein by reference.

In another embodiment, a recombinant microorganism provided herein includes elevated expression of ribose-5- phosphate isomerase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes ribulose-5-phosphate from a substrate that includes ribose-5-phosphate. The ribose-5-phosphate isomerase can be encoded by an Rpi gene, polynucleotide or homolog thereof. The Rpi gene or polynucleotide can be derived from various microorganisms including *E. coli*.

In addition to the foregoing, the terms "ribose-5-phosphate isomerase" or "Rpi" refer to proteins that are capable of catalyzing the formation of ribulose-5-phosphate from ribose 5-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:8. Additional homologs include: *Vibrio sinaloensis* DSM 21326 ZP_08101051.1 having 74% identity to SEQ ID NO:8; *Aeromonas media* WS ZP_15944363.1 having 72% identity to SEQ ID NO:8; *Thermosynechococcus elongatus* BP-1 having 48% identity to SEQ ID NO:8; *Lactobacillus suebicus* KCTC 3549 ZP_09450605.1 having 42% identity to SEQ ID NO:8; and *Homo sapiens* AAK95569.1 having 37% identity to SEQ ID NO:8. The sequences associated with the foregoing accession numbers are incorporated herein by reference.

In another embodiment, a recombinant microorganism provided herein includes elevated expression of transaldolase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes sedoheptulose-7-phosphate from a substrate that includes erythrose-4-phosphate and fructose-6-phosphate. The transaldolase can be encoded by a Tal gene, polynucleotide or homolog thereof. The Tal gene or polynucleotide can be derived from various microorganisms including *E. coli*.

In addition to the foregoing, the terms "transaldolase" or "Tal" refer to proteins that are capable of catalyzing the formation of sedoheptulose-7-phosphate from erythrose-4-phosphate and fructose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:10. Additional homologs include: *Bifidobacterium breve* DSM 20213 ZP_06596167.1 having 30% identity to SEQ ID NO:10; *Homo sapiens* AAC51151.1 having 67% identity to SEQ ID NO:10; *Cyanothece* sp. CCY0110 ZP_01731137.1 having 57% identity to SEQ ID NO:10; *Ralstonia eutropha* JMP134 YP_296277.2 having 57% identity to SEQ ID NO:10; and *Bacillus subtilis* BEST7613 NP_440132.1 having 59% identity to SEQ ID NO:10. The sequences associated with the foregoing accession numbers are incorporated herein by reference.

In another embodiment, a recombinant microorganism provided herein includes elevated expression of transketolase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes (i) ribose-5-phosphate and xylulose-5-phosphate from sedoheptulose-7-phosphate and glyceraldhyde-3-phosphate; and/or (ii) glyceraldehyde-3-phosphate and fructose-6-phosphate from xylulose-5-phosphate and erythrose-4-phosphate. The transketolase can be encoded by a Tkt gene, polynucleotide or homolog thereof. The Tkt gene or polynucleotide can be derived from various microorganisms including *E. coli*.

In addition to the foregoing, the terms "transketolase" or "Tkt" refer to proteins that are capable of catalyzing the formation of (i) ribose-5-phosphate and xylulose-5-phosphate from sedoheptulose-7-phosphate and glyceraldhyde-3-phosphate; and/or (ii) glyceraldehyde-3-phosphate and fructose-6-phosphate from xylulose-5-phosphate and erythrose-4-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:12. Additional homologs include: *Neisseria meningitidis* M13399 ZP_11612112.1 having 65% identity to SEQ ID NO:12; *Bifidobacterium breve* DSM 20213 ZP_06596168.1 having 41% identity to SEQ ID NO:12; *Ralstonia eutropha* JMP134 YP_297046.1 having 66% identity to SEQ ID NO:12; *Synechococcus elongatus* PCC 6301 YP_171693.1 having 56% identity to SEQ ID NO:12; and *Bacillus subtilis* BEST7613 NP_440630.1 having 54% identity to SEQ ID NO:12. The sequences associated with the foregoing accession numbers are incorporated herein by reference.

In another embodiment, a recombinant microorganism provided herein includes elevated expression of a hexulose-6-phosphate synthase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes hexulose-6-phosphate from formaldehyde and ribulose-6-phosphate. The hexulose-6-phosphate synthase can be encoded by an Hps gene, polynucleotide or homolog thereof. The Hps gene or polynucleotide can be derived from various microorganisms including *B. subtilis*.

In addition to the foregoing, the terms "hexulose-6-phosphate synthase" or "Hps" refer to proteins that are capable of catalyzing the formation of hexulose-6-phosphate from formaldehyde and ribulose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:14.

In another embodiment, a recombinant microorganism provided herein includes elevated expression of a hexulose-6-phosphate isomerase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes fructose-6-phosphate from hexulose-6-phosphate. The hexulose-6-phosphate isomerase can be encoded by a Phi gene, polynucleotide or homolog thereof. The Phi gene or polynucleotide can be derived from various microorganisms including *M. Flagettus*.

In addition to the foregoing, the terms "hexulose-6-phosphate isomerase" or "Phi" refer to proteins that are capable of catalyzing the formation of fructose-6-phosphate from hexulose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:16.

In another embodiment, a recombinant microorganism provided herein includes elevated expression of a dihydroxyacetone synthase as compared to a parental microorganism. The recombinant microorganism produces a metabolite that includes dihydroxyacetone and glyceraldehyde-3-phosphate from xylulose-5-phosphate and formaldehyde. The dihydroxyacetone synthase can be encoded by a Das gene, polynucleotide or homolog thereof. The Das gene or polynucleotide can be derived from various microorganisms including *C. boindii*.

In addition to the foregoing, the terms "dihydroxyacetone synthase" or "Das" refer to proteins that are capable of catalyzing the formation of dihydroxyacetone and glyceraldehyde-3-phosphate from xylulose-5-phosphate and formaldehyde, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:18.

In another embodiment, a recombinant microorganism provided herein includes elevated expression of a fructose-6-phosphate aldolase as compared to a parental microorganism. This expression may be combined with the expression or over-expression with other enzymes in the metabolic pathway for the production of acetyl-phosphate, acetyl-CoA or other metabolites derived therefrom as described herein above and below. The recombinant microorganism produces a metabolite that includes fructose-6-phosphate from glyceraldehyde-3-phosphate and dihydroxyacetone. The fructose-6-phosphate aldolase can be encoded by a Fsa gene, polynucleotide or homolog thereof. The Fsa gene or polynucleotide can be derived from various microorganisms including *S. enterica*.

In addition to the foregoing, the terms "fructose-6-phosphate aldolase" or "Fsa" refer to proteins that are capable of catalyzing the formation of fructose-6-phosphate from glyceraldehyde-3-phosphate and dihydroxyacetone, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:20.

Figure 8:
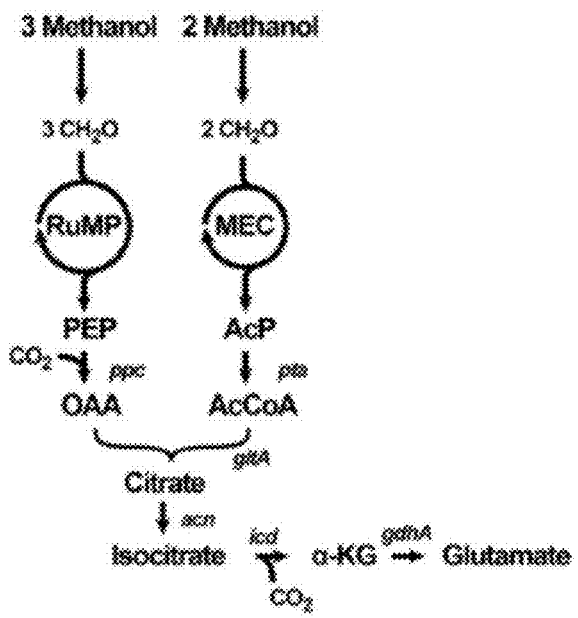
FIG. 8 shows a pathway for the production of citrate, isocitrate and glutamate using acetyl-phosphate produced through the MEC pathway of the disclosure.

In addition to engineering a MEC pathway into a microorganism, the microorganism can be further engineered to convert the acetyl-phosphate produced by MEC to acetyl-CoA. The acetyl-CoA can then be utilized to produce various chemicals and biofuels as shown in FIGS. 6-8. Thus, in one embodiment, the microorganism can be further engineered to express an enzyme that converts acetyl-phosphate to acetyl-CoA. Phosphate acetyltransferase (EC 2.3.1.8) is an enzyme that catalyzes the chemical reaction of acetyl-CoA+phosphate to CoA+acetyl phosphate and vice versa. Phosphate acetyltransferase is encoded in *E. coli* by pta. PTA is involved in conversion of acetate to acetyl-CoA. Specifically, PTA catalyzes the conversion of acetyl-coA to acetyl-phosphate. PTA homologs and variants are known. There are approximately 1075 bacterial phosphate acetyltransferases available on NCBI. For example, such homologs and variants include phosphate acetyltransferase Pta (*Rickettsia felis* URRWXCal2) gi|67004021|gb|AAY60947.1|(67004021); phosphate acetyltransferase (*Buchnera aphidicola* str. Cc (*Cinara cedri*)) gi|116256910|gb|ABJ90592.1|(116256910); pta (*Buchnera aphidicola* str. Cc (*Cinara cedri*)) gi|116515056|ref|YP_802685.1|(116515056); pta (*Wigglesworthia glossinidia endosymbiont* of *Glossina brevipalpis*) gi|25166135|dbj|BAC24326.1|(25166135); Pta (*Pasteurella multocida* subsp. *multocida* str. Pm70) gi|12720993|gb|AAK02789.1|(12720993); Pta (*Rhodospirillum rubrum*) gi|25989720|gb|AAN75024.1| (25989720); pta (*Listeria welshimeri serovar* 6b str. SLCC5334) gi|116742418|emb|CAK21542.1|(116742418); Pta (*Mycobacterium avium* subsp. paratuberculosis K-10) gi|41398816|gb|AAS06435.1|(41398816); phosphate acetyltransferase (pta) (*Borrelia burgdorferi* B31) gi|15594934|ref|NP_212723.1|(15594934); phosphate acetyltransferase (pta) (*Borrelia burgdorferi* B31) gi|2688508|gb|AAB91518.1|(2688508); phosphate acetyltransferase (pta) (*Haemophilus influenzae* Rd KW20) gi|1574131|gb|AAC22857.1|(1574131); Phosphate acetyltransferase Pta (*Rickettsia bellii* RML369-C) gi|91206026|ref|YP_538381.1|(91206026); Phosphate acetyltransferase Pta (*Rickettsia bellii* RML369-C) gi|91206025|ref|YP_538380.1|(91206025); phosphate acetyltransferase pta (*Mycobacterium tuberculosis* F11) gi|148720131|gb|ABR04756.1|(148720131); phosphate acetyltransferase pta (*Mycobacterium tuberculosis* str. Haarlem) gi|134148886|gb|EBA40931.1|(134148886); phosphate acetyltransferase pta (*Mycobacterium tuberculosis* C) gi|124599819|gb|EAY58829.1|(124599819); Phosphate acetyltransferase Pta (*Rickettsia bellii* RML369-C) gi|91069570|gb|ABE05292.1|(91069570); Phosphate acetyltransferase Pta (*Rickettsia bellii* RML369-C) gi|91069569|gb|ABE05291.1|(91069569); phosphate acetyltransferase (pta) (*Treponema pallidum* subsp. *pallidum* str. Nichols) gi|15639088|ref|NP_218534.1| (15639088); and phosphate acetyltransferase (pta) (*Treponema pallidum* subsp. *pallidum* str. Nichols) gi|3322356|gb|AAC65090.1|(3322356), each sequence associated with the accession number is incorporated herein by reference in its entirety.

In another embodiment, the acetyl-CoA pathway can be extended by expressing an acetoacetyl-CoA thiolase that converts acetyl-CoA to acetoacetyl-CoA. An acetoacetyl-coA thiolase (also sometimes referred to as an acetyl-coA acetyltransferase) catalyzes the production of acetoacetyl-coA from two molecules of acetyl-coA. Depending upon the organism used a heterologous acetoacetyl-coA thiolase (acetyl-coA acetyltransferase) can be engineered for expression in the organism. Alternatively a native acetoacetyl-coA thiolase (acetyl-coA acetyltransferase) can be overexpressed. Acetoacetyl-coA thiolase is encoded in *E. coli* by atoB (SEQ ID NO:23; the polypeptide is SEQ ID NO:24). Acetyl-coA acetyltransferase is encoded in *C. acetobutylicum* by thlA (SEQ ID NO:25 and the polypeptide is SEQ ID NO:26). THL and AtoB homologs and variants are known.

For examples, such homologs and variants include, for example, acetyl-coA acetyltransferase (thiolase) (*Streptomyces coelicolor* A3(2)) gi|21224359|ref|NP-630138.1| (21224359); acetyl-coA acetyltransferase (thiolase) (*Streptomyces coelicolor* A3(2)) gi|3169041|emb|CAA19239.1| (3169041); Acetyl CoA acetyltransferase (thiolase) (*Alcanivorax borkumensis* SK2) gi|110834428|ref|YP-693287.1|(110834428); Acetyl CoA acetyltransferase (thiolase) (*Alcanivorax borkumensis* SK2) gi|110647539|emb|CAL17015.1|(110647539); acetyl CoA acetyltransferase (thiolase) (*Saccharopolyspora erythraea* NRRL 2338) gi|133915420|emb|CAM05533.1| (133915420); acetyl-coA acetyltransferase (thiolase) (*Saccharopolyspora erythraea* NRRL 2338) gi|134098403|ref|YP-001104064.1|(134098403); acetyl-coa acetyltransferase (thiolase) (*Saccharopolyspora erythraea* NRRL 2338) gi|133911026|emb|CAM01139.1| (133911026); acetyl-CoA acetyltransferase (thiolase) (*Clostridium botulinum* A str. ATCC 3502) gi|148290632|emb|CAL84761.1|(148290632); acetyl-CoA acetyltransferase (thiolase) (*Pseudomonas aeruginosa* UCBPP-PA14) gi|115586808|gb|ABJ12823.1| (115586808); acetyl-CoA acetyltransferase (thiolase) (*Ralstonia metallidurans* CH34) gi|93358270|gb|ABF12358.1| (93358270); acetyl-CoA acetyltransferase (thiolase) (*Ralstonia metallidurans* CH34) gi|93357190|gb|ABF11278.1|(93357190); acetyl-CoA acetyltransferase (thiolase) (*Ralstonia metallidurans* CH34) gi|93356587|gb|ABF10675.1|(93356587); acetyl-CoA acetyltransferase (thiolase) (*Ralstonia eutropha* JMP134) gi|72121949|gb|AAZ64135.1|(72121949); acetyl-CoA acetyltransferase (thiolase) (*Ralstonia eutropha* JMP134) gi|72121729| gb|AAZ63915.1|(72121729); acetyl-CoA acetyltransferase (thiolase) (*Ralstonia eutropha* JMP134) gi|72121320|gb|AAZ63506.1|(72121320); acetyl-CoA acetyltransferase (thiolase) (*Ralstonia eutropha* JMP134) gi|72121001|gb|AAZ63187.1|(72121001); acetyl-CoA acetyltransferase (thiolase) (*Escherichia coli*) gi|2764832|emb|CAA66099.1|(2764832), each sequence associated with the accession number is incorporated herein by reference in its entirety.

The recombinant microorganism can be engineered to produce a metabolite that includes a 3-hydroxybutyryl-CoA from a substrate that includes acetoacetyl-CoA. The hydroxybutyryl-CoA dehydrogenase can be encoded by an hbd gene or homolog thereof. The hbd gene can be derived from various microorganisms including *Clostridium acetobutylicum*, *Clostridium difficile*, *Dastricha ruminatium*, *Butyrivibrio fibrisolvens*, *Treponema phagedemes*, *Acidaminococcus fermentans*, *Clostridium kluyveri*, *Syntrophospora bryanti*, and *Thermoanaerobacterium thermosaccharolyticum*.

A 3-hydroxybutyryl-coA-dehydrogenase catalyzes the conversion of acetoacetyl-coA to 3-hydroxybutyryl-CoA. Depending upon the organism used a heterologous 3-hydroxybutyryl-coA-dehydrogenase can be engineered for expression in the organism. Alternatively a native 3-hydroxybutyryl-coA-dehydrogenase can be overexpressed. 3-hydroxybutyryl-coA-dehydrogenase is encoded in *C. acetobuylicum* by hbd (SEQ ID NO:27). HBD homologs and variants are known. For examples, such homologs and variants include, for example, 3-hydroxybutyryl-CoA dehydrogenase (*Clostridium acetobutylicum* ATCC 824) gi|15895965|ref|NP_349314.1|(15895965); 3-hydroxybutyryl-CoA dehydrogenase (*Bordetella pertussis Tohama* I) gi|23571103|emb|CAE40597.1|(33571103); 3-hydroxybutyryl-CoA dehydrogenase (*Streptomyces coelicolor* A3(2)) gi|21223745|ref|NP_629524.1|(21223745); 3-hydroxybutyryl-CoA dehydrogenase gi|1055222|gb|AAA95971.1| (1055222); 3-hydroxybutyryl-CoA dehydrogenase (*Clostridium perfringens* str. 13) gi|18311280|ref|NP_563214.1|(18311280); 3-hydroxybutyryl-CoA dehydrogenase (*Clostridium perfringens* str. 13) gi|18145963|dbj|BAB82004.1|(18145963) each sequence associated with the accession number is incorporated herein by reference in its entirety. SEQ ID NO:28 sets forth an exemplary hbd polypeptide sequence. In certain embodiments, the 3 hydroxybutyryl-coA-dehydrogenase can have an amino acid sequence that is substantially identical to the amino acid sequence of SEQ ID NO: 28 and having 3 hydroxy-butyryl-coA-dehydrogenase activity. For example, the disclosure includes polypeptides having at least about 80% identity, at least about 85%, at least about 90%, at least about 91%, at least about 92%, at least about 93%, at least about 94%, at least about 95%, at least about 96%, at least about 97%, at least about 98%, and at least about 99% identity to SEQ ID NO:28 and having 3 hydroxy-butyryl-coA-dehydrogenase. In other embodiments, the 3 hydroxybutyryl-coA-dehydrogenase can have an amino acid sequence derived from the amino acid sequence of SEQ ID NO:28 by substitution, deletion, addition, or insertion of 1 or more amino acid(s) (e.g., 1-10) and having 3 hydroxybutyryl-coA-dehydrogenase activity.

Crotonase catalyzes the conversion of 3-hydroxybutyryl-CoA to crotonyl-CoA. Depending upon the organism used a heterologous crotonase can be engineered for expression in the organism. Alternatively, a native crotonase can be overexpressed. Crotonase is encoded in *C. acetobuylicum* by crt (SEQ ID NO:29). CRT homologs and variants are known. For examples, such homologs and variants include, for example, crotonase (butyrate-producing bacterium L2-50) gi|119370267|gb|ABL68062.1|(119370267); crotonase gi|1055218|gb|AAA95967.1|(1055218); crotonase (*Clostridium perfringens* NCTC 8239) gi|168218170|ref|ZP_02643795.1|(168218170); crotonase (*Clostridium perfringens* CPE str. F4969) gi|168215036|ref|ZP_02640661.1|(168215036); crotonase (*Clostridium perfringens* E str. JGS1987) gi|168207716|ref|ZP_02633721.1|(168207716); crotonase (*Azoarcus* sp. EbN1) gi|56476648|ref|YP_158237.1| (56476648); crotonase (*Roseovarius* sp. TM1035) gi|149203066|ref|ZP_01880037.1|(149203066); crotonase (*Roseovarius* sp. TM1035) gi|149143612|gb|EDM31648.1| (149143612); crotonase; 3-hydroxbutyryl-CoA dehydratase (*Mesorhizobium loti* MAFF303099) gi|14027492|dbj|BAB53761.1|(14027492); crotonase (*Roseobacter* sp. SK209-2-6) gi|126738922|ref|ZP_01754618.1|(126738922); crotonase (*Roseobacter* sp. SK209-2-6) gi|126720103|gb|EBA16810.1|(126720103); crotonase (*Marinobacter* sp. ELB17) gi|126665001|ref|ZP_01735984.1|(126665001); crotonase (*Marinobacter* sp. ELB17) gi|126630371|gb|EBA00986.1| (126630371); crotonase (*Azoarcus* sp. EbN1) gi|56312691|emb|CAI07336.1|(56312691); crotonase (*Marinomonas* sp. MED121) gi|86166463|gb|EAQ67729.1| (86166463); crotonase (*Marinomonas* sp. MED121) gi|87118829|ref|ZP_01074728.1|(87118829); crotonase (*Roseovarius* sp. 217) gi|85705898|ref|ZP_01036994.1| (85705898); crotonase (*Roseovarius* sp. 217) gi|85669486|gb|EAQ24351.1|(85669486); crotonase gi|1055218|gb|AAA95967.1|(1055218); 3-hydroxybutyryl-CoA dehydratase (Crotonase) gi|1706153|sp|P52046.1|CRT_CLOAB (1706153); Crotonase (3-hydroxybutyryl-COA dehydratase) (*Clostridium acetobutylicum* ATCC 824) gi|15025745|gb|AAK80658.1|AE007768_12 (15025745) each sequence associated with the accession number is incorporated herein by reference in its entirety. SEQ ID NO:30 sets forth an exemplary crt polypeptide sequence. In certain embodiments, the crotonase can have an amino acid sequence that is substantially identical to the amino acid sequence of SEQ ID NO:30 and having crotonase activity. For example, the disclosure includes polypeptides having at least about 80% identity, at least about 85%, at least about 90%, at least about 91%, at least about 92%, at least about 93%, at least about 94%, at least about 95%, at least about 96%, at least about 97%, at least about 98%, and at least about 99% identity to SEQ ID NO:30 and having crotonase. In other embodiments, the crotonase can have an amino acid sequence derived from the amino acid sequence of SEQ ID NO:30 by substitution, deletion, addition, or insertion of 1 or more amino acid(s) (e.g., 1-10) and having crotonase activity. This expression may be combined with the expression or over-expression with other enzymes in the metabolic pathway for the production of acetyl-phosphate, acetyl-CoA or other metabolites derived therefrom as described herein above and below.

In yet another embodiment, a recombinant microorganism provided herein includes elevated expression of a crotonyl-CoA reductase as compared to a parental microorganism. This expression may be combined with the expression or over-expression with other enzymes in the metabolic pathway for the production of n-butanol, isobutanol, butyryl-coA and/or acetone. The microorganism produces a metabolite that includes butyryl-CoA from a substrate that includes crotonyl-CoA. The crotonyl-CoA reductase can be encoded by a ccr gene, polynucleotide or homolog thereof. For examples, such homologs and variants include, for example, crotonyl CoA reductase (*Streptomyces coelicolor* A3(2)) gi|21224777|ref|NP_630556.1|(21224777); crotonyl CoA reductase (*Streptomyces coelicolor* A3(2)) gi|4154068|emb|CAA22721.1|(4154068); crotonyl-CoA reductase (*Methylobacterium* sp. 4-46) gi|168192678|gb|ACA14625.1|(168192678); crotonyl-CoA reductase (*Dinoroseobacter shibae* DFL 12) gi|159045393|ref|YP_001534187.1|(159045393); crotonyl-CoA reductase (*Salinispora arenicola* CNS-205) gi|159039522|ref|YP_001538775.1|(159039522); crotonyl-CoA reductase (*Methylobacterium extorquens* PA1) gi|163849740|ref|YP_001637783.1|(163849740); crotonyl-CoA reductase (*Methylobacterium extorquens* PA1) gi|163661345|gb|ABY28712.1|(163661345); crotonyl-CoA reductase (*Burkholderia ambifaria* AMMD) gi|115360962|ref|YP_778099.1|(115360962); crotonyl-CoA reductase (*Parvibaculum lavamentivorans* DS-1) gi|154252073|ref|YP_001412897.1|(154252073); Crotonyl-CoA reductase (*Silicibacter* sp. TM1040) gi|99078082|ref|YP_611340.1|(99078082); crotonyl-CoA reductase (*Xanthobacter autotrophicus* Py2) gi|154245143|ref|YP_001416101.1|(154245143); crotonyl-CoA reductase (*Nocardioides* sp. JS614) gi|119716029|ref|YP_922994.1|(119716029); crotonyl-CoA reductase (*Nocardioides* sp. JS614) gi|119536690|gb|ABL81307.1|(119536690); crotonyl-CoA reductase (*Salinispora arenicola* CNS-205) gi|157918357|gb|ABV99784.1|(157918357); crotonyl-CoA reductase (*Dinoroseobacter shibae* DFL 12) gi|157913153|gb|ABV94586.1|(157913153); crotonyl-CoA reductase (*Burkholderia ambifaria* AMMD) gi|115286290|gb|ABI91765.1|(115286290); crotonyl-CoA reductase (*Xanthobacter autotrophicus* Py2) gi|154159228|gb|ABS66444.1|(154159228); crotonyl-CoA reductase (*Parvibaculum lavamentivorans* DS-1) gi|154156023|gb|ABS63240.1|(154156023); crotonyl-CoA reductase (*Methylobacterium radiotolerans* JCM 2831) gi|170654059|gb|ACB23114.1|(170654059); crotonyl-CoA reductase (*Burkholderia graminis* C4D1M) gi|170140183|gb|EDT08361.1|(170140183); crotonyl-CoA reductase (*Methylobacterium* sp. 4-46) gi|168198006|gb|ACA19953.1|(168198006); crotonyl-CoA reductase (*Frankia* sp. EAN1pec) gi|158315836|ref|YP_001508344.1|(158315836), each sequence associated with the accession number is incorporated herein by reference in its entirety. The ccr gene or polynucleotide can be derived from the genus *Streptomyces* (see, SEQ ID NO:31).

Alternatively, or in addition to, the microorganism provided herein includes elevated expression of a trans-2-hexenoyl-CoA reductase as compared to a parental microorganism. The microorganism produces a metabolite that includes butyryl-CoA from a substrate that includes crotonyl-CoA. The trans-2-hexenoyl-CoA reductase can also convert trans-2-hexenoyl-CoA to hexanoyl-CoA. The trans-2-hexenoyl-CoA reductase can be encoded by a ter gene, polynucleotide or homolog thereof. The ter gene or polynucleotide can be derived from the genus *Euglena*. The ter gene or polynucleotide can be derived from *Treponema denticola*. The enzyme from *Euglena gracilis* acts on crotonoyl-CoA and, more slowly, on trans-hex-2-enoyl-CoA and trans-oct-2-enoyl-CoA.

A Trans-2-enoyl-CoA reductase or TER can be used to convert crotonyl-CoA to butyryl-CoA. TER is a protein that is capable of catalyzing the conversion of crotonyl-CoA to butyryl-CoA, and trans-2-hexenoyl-CoA to hexanoyl-CoA. In certain embodiments, the recombinant microorganism expresses a TER which catalyzes the same reaction as Bcd/EtfA/EtfB from *Clostridia* and other bacterial species. Mitochondrial TER from *E. gracilis* has been described, and many TER proteins and proteins with TER activity derived from a number of species have been identified forming a TER protein family (see, e.g., U.S. Pat. Appl. 2007/0022497 to Cirpus et al.; and Hoffmeister et al., J. Biol. Chem., 280:4329-4338, 2005, both of which are incorporated herein by reference in their entirety). A truncated cDNA of the *E. gracilis* gene has been functionally expressed in *E. coli*.

In addition to the foregoing, the terms "trans-2-enoyl-CoA reductase" or "TER" refer to proteins that are capable of catalyzing the conversion of crotonyl-CoA to butyryl-CoA, or trans-2-hexenoyl-CoA to hexanoyl-CoA and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to either or both of the truncated *E. gracilis* TER or the full length *A. hydrophila* TER. In one embodiment, a TER protein (SEQ ID NO:33) or homolog of variant thereof can be used in the methods and compositions of the disclosure.

Butyraldehyde dehydrogenase (Bldh) generates butyraldehyde from butyryl-CoA and NADPH. In certain embodiments, the butyraldehyde dehydrogenase can have an amino acid sequence that is substantially identical to the amino acid sequence of SEQ ID NO: 35 and having butyraldehyde dehydrogenase activity. For example, the disclosure includes polypeptides having at least about 80% identity, at least about 85%, at least about 90%, at least about 91%, at least about 92%, at least about 93%, at least about 94%, at least about 95%, at least about 96%, at least about 97%, at least about 98%, and at least about 99% identity to SEQ ID NO:35 and having butyraldehyde dehydrogenase activity. In other embodiments, the butyraldehyde dehydrogenase can have an amino acid sequence derived from the amino acid sequence of SEQ ID NO:35 by substitution, deletion, addition, or insertion of 1 or more amino acid(s) (e.g., 1-10) and having Butyraldehyde dehydrogenase activity.

E. coli contains a native gene (yqhD) that was identified as a 1,3-propanediol dehydrogenase (U.S. Pat. No. 6,514,733). The yqhD gene, given as SEQ ID NO:36, has 40% identity to the gene adhB in Clostridium, a probable NADH-dependent butanol dehydrogenase. In certain embodiments, the 1,3-propanediol dehydrogenase can have an amino acid sequence that is substantially identical to the amino acid sequence of SEQ ID NO: 37 and having 1,3-propanediol dehydrogenase activity. For example, the disclosure includes polypeptides having at least about 80% identity, at least about 85%, at least about 90%, at least about 91%, at least about 92%, at least about 93%, at least about 94%, at least about 95%, at least about 96%, at least about 97%, at least about 98%, and at least about 99% identity to SEQ ID NO:37 and having 1,3-propanediol dehydrogenase activity. In other embodiments, the 1,3-propanediol dehydrogenase can have an amino acid sequence derived from the amino acid sequence of SEQ ID NO:37 by substitution, deletion, addition, or insertion of 1 or more amino acid(s) (e.g., 1-10) and having 1,3-propanediol dehydrogenase activity.

In yet another embodiment, a recombinant microorganism provided herein includes expression or elevated expression of an alcohol dehydrogenase (ADHE2; SEQ ID NO:39) as compared to a parental microorganism. The recombinant microorganism produces a metabolite that includes butanol from a substrate that includes butyryl-CoA. The alcohol dehydrogenase can be encoded by bdhA/bdhB polynucleotide or homolog thereof, an aad gene, polynucleotide or homolog thereof, or an adhE2 gene, polynucleotide or homolog thereof. The aad gene or adhE2 gene or polynucleotide can be derived from Clostridium acetobutylicum. Aldehyde/alcohol dehydrogenase catalyzes the conversion of butyryl-CoA to butyraldehyde and butyraldehyde to 1-butanol. In one embodiment, the aldehyde/alcohol dehydrogenase preferentially catalyzes the conversion of butyryl-CoA to butyraldehyde and butyraldehyde to 1-butanol. Depending upon the organism used a heterologous aldehyde/alcohol dehydrogenase can be engineered for expression in the organism. Alternatively, a native aldehyde/alcohol dehydrogenase can be overexpressed. Aldehyde/alcohol dehydrogenase is encoded in C. acetobuylicum by adhE (e.g., an adhE2). ADHE (e.g., ADHE2) homologs and variants are known. For examples, such homologs and variants include, for example, aldehyde-alcohol dehydrogenase (Clostridium acetobutylicum) gi|3790107|gb|AAD04638.1|(3790107); aldehyde-alcohol dehydrogenase (Clostridium botulinum A str. ATCC 3502) gi|148378348|ref|YP_001252889.1| (148378348); Aldehyde-alcohol dehydrogenase (Includes: Alcohol dehydrogenase (ADH) Acetaldehyde dehydrogenase (acetylating) (ACDH) gi|19858620|sp|P33744.3|ADHE_CLOAB (19858620); Aldehyde dehydrogenase (NAD+) (Clostridium acetobutylicum ATCC 824) gi|15004865|ref|NP_149325.1| (15004865); alcohol dehydrogenase E (Clostridium acetobutylicum) gi|298083|emb|CAA51344.1|(298083); Aldehyde dehydrogenase (NAD+) (Clostridium acetobutylicum ATCC 824) gi|14994477|gb|AAK76907.1|AE001438_160(14994477); aldehyde/alcohol dehydrogenase (Clostridium acetobutylicum) gi|12958626|gb|AAK09379.1|AF321779_1 (12958626); Aldehyde-alcohol dehydrogenase, ADHE1 (Clostridium acetobutylicum ATCC 824) gi|15004739|ref|NP_149199.1|(15004739); Aldehyde-alcohol dehydrogenase, ADHE1 (Clostridium acetobutylicum ATCC 824) gi|14994351|gb|AAK76781.1|AE001438_34 (14994351); aldehyde-alcohol dehydrogenase E (Clostridium perfringens str. 13) gi|18311513|ref|NP_563447.1|(18311513); aldehyde-alcohol dehydrogenase E (Clostridium perfringens str. 13) gi|18146197|dbj|BAB82237.1|(18146197), each sequence associated with the accession number is incorporated herein by reference in its entirety.

In yet another embodiment, a recombinant microorganism provided herein includes elevated expression of a butyryl-CoA dehydrogenase as compared to a parental microorganism. This expression may be combined with the expression or over-expression with other enzymes in the metabolic pathway for the production of 1-butanol, isobutanol, acetone, octanol, hexanol, 2-pentanone, and butyryl-coA as described herein above and below. The recombinant microorganism produces a metabolite that includes butyryl-CoA from a substrate that includes crotonyl-CoA. The butyryl-CoA dehydrogenase can be encoded by a bcd gene, polynucleotide or homolog thereof. The bcd gene, polynucleotide can be derived from Clostridium acetobutylicum, Mycobacterium tuberculosis, or Megasphaera elsdenii.

In another embodiment, a recombinant microorganism provided herein includes expression or elevated expression of an acetyl-CoA acetyltransferase as compared to a parental microorganism. The microorganism produces a metabolite that includes acetoacetyl-CoA from a substrate that includes acetyl-CoA. The acetyl-CoA acetyltransferase can be encoded by a thlA gene, polynucleotide or homolog thereof. The thlA gene or polynucleotide can be derived from the genus Clostridium.

Pyruvate-formate lyase (Formate acetyltransferase) is an enzyme that catalyzes the conversion of pyruvate to acetly-coA and formate. In some embodiments, it may be desirable to reduce or eliminate the expression of pyruvate lyase. It is induced by pfl-activating enzyme under anaerobic conditions by generation of an organic free radical and decreases significantly during phosphate limitation. Formate acetlytransferase is encoded in E. coli by pflB. PFLB homologs and variants are known. For examples, such homologs and variants include, for example, Formate acetyltransferase 1 (Pyruvate formate-lyase 1) gi|129879|sp|P09373.2|PFLB_ECOLI (129879); formate acetyltransferase 1 (Yersinia pestis CO92) gi|16121663|ref|NP_404976.1|(16121663); formate acetyltransferase 1 (Yersinia pseudotuberculosis IP 32953) gi|51595748|ref|YP_069939.1|(51595748); formate acetyltransferase 1 (Yersinia pestis biovar Microtus str. 91001) gi|45441037|ref|NP_992576.1|(45441037); formate acetyltransferase 1 (Yersinia pestis CO92) gi|115347142|emb|CAL20035.1|(115347142); formate acetyltransferase 1 (Yersinia pestis biovar Microtus str. 91001) gi|45435896|gb|AAS61453.1|(45435896); formate acetyltransferase 1 (Yersinia pseudotuberculosis IP 32953) gi|51589030|emb|CAH20648.1|(51589030); formate acetyltransferase 1 (Salmonella enterica subsp. enterica serovar Typhi str. CT18) gi|16759843|ref|NP_455460.1| (16759843); formate acetyltransferase 1 (Salmonella enterica subsp. enterica serovar Paratyphi A str. ATCC 9150) gi|56413977|ref|YP_151052.1|(56413977); formate acetyltransferase 1 (Salmonella enterica subsp. enterica serovar

*Typhi*) gi|16502136|emb|CAD05373.1|(16502136); formate acetyltransferase 1 (*Salmonella enterica* subsp. enterica serovar Paratyphi A str. ATCC 9150) gi|56128234|gb|AAV77740.1|(56128234); formate acetyltransferase 1 (*Shigella dysenteriae* Sd197) gi|82777577|ref|YP_403926.1|(82777577); formate acetyltransferase 1 (*Shigella flexneri* 2a str. 2457T) gi|30062438|ref|NP_836609.1|(30062438); formate acetyltransferase 1 (*Shigella flexneri* 2a str. 2457T) gi|30040684|gb|AAP16415.1|(30040684); formate acetyltransferase 1 (*Shigella flexneri* 5 str. 8401) gi|110614459|gb|ABF03126.1|(110614459); formate acetyltransferase 1 (*Shigella dysenteriae* Sd197) gi|81241725|gb|ABB62435.1|(81241725); formate acetyltransferase 1 (*Escherichia coli* 0157:H7 EDL933) gi|12514066|gb|AAG55388.1|AE005279_8(12514066); formate acetyltransferase 1 (*Yersinia pestis* KIM) gi|22126668|ref|NP_670091.1|(22126668); formate acetyltransferase 1 (*Streptococcus agalactiae* A909) gi|76787667|ref|YP_330335.1|(76787667); formate acetyltransferase 1 (*Yersinia pestis* KIM) gi|21959683|gb|AAM86342.1|AE013882_3(21959683); formate acetyltransferase 1 (*Streptococcus agalactiae* A909) gi|76562724|gb|ABA45308.1|(76562724); formate acetyltransferase 1 (*Yersinia enterocolitica* subsp. enterocolitica 8081) gi|123441844|ref|YP_001005827.1| (123441844); formate acetyltransferase 1 (*Shigella flexneri* 5 str. 8401) gi|110804911|ref|YP_688431.1|(110804911); formate acetyltransferase 1 (*Escherichia coli* UTI89) gi|91210004|ref|YP_539990.1|(91210004); formate acetyltransferase 1 (*Shigella boydii* Sb227) gi|82544641|ref|YP_408588.1|(82544641); formate acetyltransferase 1 (*Shigella sonnei* Ss046) gi|74311459|ref|YP_309878.1|(74311459); formate acetyltransferase 1 (*Klebsiella pneumoniae* subsp. pneumoniae MGH 78578) gi|152969488|ref|YP_001334597.1| (152969488); formate acetyltransferase 1 (*Salmonella enterica* subsp. enterica serovar Typhi Ty2) gi|29142384|ref|NP_805726.1|(29142384) formate acetyltransferase 1 (*Shigella flexneri* 2a str. 301) gi|24112311|ref|NP_706821.1|(24112311); formate acetyltransferase 1 (*Escherichia coli* 0157:H7 EDL933) gi|15800764|ref|NP_286778.1|(15800764); formate acetyltransferase 1 (*Klebsiella pneumoniae* subsp. pneumoniae MGH 78578) gi|150954337|gb|ABR76367.1|(150954337); formate acetyltransferase 1 (*Yersinia pestis* CA88-4125) gi|149366640|ref|ZP_01888674.1|(149366640); formate acetyltransferase 1 (*Yersinia pestis* CA88-4125) gi|149291014|gb|EDM41089.1|(149291014); formate acetyltransferase 1 (*Yersinia enterocolitica* subsp. enterocolitica 8081) gi|122088805|emb|CAL11611.1|(122088805); formate acetyltransferase 1 (*Shigella sonnei* Ss046) gi|73854936|gb|AAZ87643.1|(73854936); formate acetyltransferase 1 (*Escherichia coli* UTI89) gi|91071578|gb|ABE06459.1|(91071578); formate acetyltransferase 1 (*Salmonella enterica* subsp. enterica serovar Typhi Ty2) gi|29138014|gb|AA069575.1|(29138014); formate acetyltransferase 1 (*Shigella boydii* Sb227) gi|81246052|gb|ABB66760.1|(81246052); formate acetyltransferase 1 (*Shigella flexneri* 2a str. 301) gi|24051169|gb|AAN42528.1|(24051169); formate acetyltransferase 1 (*Escherichia coli* 0157:H7 str. Sakai) gi|13360445|dbj|BAB34409.1|(13360445); formate acetyltransferase 1 (*Escherichia coli* 0157:H7 str. Sakai) gi|15830240|ref|NP_309013.1|(15830240); formate acetyltransferase I (pyruvate formate-lyase 1) (*Photorhabdus luminescens* subsp. laumondii TT01) gi|36784986|emb|CAE13906.1|(36784986); formate acetyltransferase I (pyruvate formate-lyase 1) (*Photorhabdus luminescens* subsp. laumondii TT01) gi|37525558|ref|NP_928902.1|(37525558); formate acetyltransferase (*Staphylococcus aureus* subsp. aureus Mu50) gi|14245993|dbj|BAB56388.1|(14245993); formate acetyltransferase (*Staphylococcus aureus* subsp. aureus Mu50) gi|15923216|ref|NP_370750.1|(15923216); Formate acetyltransferase (Pyruvate formate-lyase) gi|81706366|sp|Q7A7X6.1|PFLB_STAAN (81706366); Formate acetyltransferase (Pyruvate formate-lyase) gi|81782287|sp|Q99WZ7.1|PFLB_STAAM (81782287); Formate acetyltransferase (Pyruvate formate-lyase) gi|81704726|sp|Q7A1W9.1|PFLB_STAAW (81704726); formate acetyltransferase (*Staphylococcus aureus* subsp. aureus Mu3) gi|156720691|dbj|BAF77108.1|(156720691); formate acetyltransferase (*Erwinia carotovora* subsp. atroseptica SCRI1043) gi|50121521|ref|YP_050688.1| (50121521); formate acetyltransferase (*Erwinia carotovora* subsp. atroseptica SCRI1043) gi|49612047|emb|CAG75496.1|(49612047); formate acetyltransferase (*Staphylococcus aureus* subsp. aureus str. Newman) gi|150373174|dbj|BAF66434.1|(150373174); formate acetyltransferase (*Shewanella oneidensis* MR-1) gi|24374439|ref|NP_718482.1|(24374439); formate acetyltransferase (*Shewanella oneidensis* MR-1) gi|24349015|gb|AAN55926.1|AE015730_3(24349015); formate acetyltransferase (*Actinobacillus pleuropneumoniae* serovar 3 str. JL03) gi|165976461|ref|YP_001652054.1| (165976461); formate acetyltransferase (*Actinobacillus pleuropneumoniae* serovar 3 str. JL03) gi|165876562|gb|ABY69610.1|(165876562); formate acetyltransferase (*Staphylococcus aureus* subsp. aureus MW2) gi|21203365|dbj|BAB94066.1|(21203365); formate acetyltransferase (*Staphylococcus aureus* subsp. aureus N315) gi|13700141|dbj|BAB41440.1|(13700141); formate acetyltransferase (*Staphylococcus aureus* subsp. aureus str. Newman) gi|151220374|ref|YP_001331197.1| (151220374); formate acetyltransferase (*Staphylococcus aureus* subsp. aureus Mu3) gi|156978556|ref|YP_001440815.1|(156978556); formate acetyltransferase (*Synechococcus* sp. JA-2-3B'a (2-13)) gi|86607744|ref|YP_476506.1|(86607744); formate acetyltransferase (*Synechococcus* sp. JA-3-3Ab) gi|86605195|ref|YP_473958.1|(86605195); formate acetyltransferase (*Streptococcus pneumoniae* D39) gi|116517188|ref|YP_815928.1|(116517188); formate acetyltransferase (*Synechococcus* sp. JA-2-3B'a (2-13)) gi|86556286|gb|ABD01243.1|(86556286); formate acetyltransferase (*Synechococcus* sp. JA-3-3Ab) gi|86553737|gb|ABC98695.1|(86553737); formate acetyltransferase (*Clostridium novyi* NT) gi|118134908|gb|ABK61952.1|(118134908); formate acetyltransferase (*Staphylococcus aureus* subsp. aureus MRSA252) gi|49482458|ref|YP_039682.1|(49482458); and formate acetyltransferase (*Staphylococcus aureus* subsp. aureus MRSA252) gi|49240587|emb|CAG39244.1| (49240587), each sequence associated with the accession number is incorporated herein by reference in its entirety.

In yeast, it may be desirable to knockout (or reduce the activity or expression of) one or more of the following: pyruvate decarboxylase (e.g., PDC1, PDC5, PDC6), formaldehyde dehydrogenase (SFA1) and/or glyceraldehyde-3-phosphate dehydrogenase (e.g., TDH1, TDH2, TDH3). Glyceraldehyde-3-phsopahte dehydrogenases are known. For example, TDH1 from *S. cerevisiae* (Accession Number: #NM_001181485); *Kluyveromyces marxianus* (aceesion number: AH004790; 85% identity to *S. cerevisiae*); *Clavispora lusitaniae* ATCC 42720 (accession number: XM_002616212; 78% identity to *S. cerevisiae* TDH1); *Pichia angusta* (accession number: U95625; 76% identity to *S. Cerevisae* TDH1). Similarly, pyruvate decarboxylases are known. For example, PDC1 from *S. cerevisiae* (Accession number: YLR044C); *Pichia stipitis* (accession number U75310; 73% identity to *S. cerevisiae* PDC1); *Candida tropicalis* (accession number AY538780; 67% identity to *S. cerevisiae* PCD1); *Candida orthopsilosis* (accession number: HE681721; 65% identity to *S. cerevisae* PDC1); and *Clavispora lusitaniae* ATCC 42720 (accession number XM 002619854; 64% identity to *S. cerevisae* PDC1). Similarly formaldehyde dehydrogenases are known. For example, Formaldehyde dehydrogenase from *S. cerevisiae* (accession number: BK006938); *Kluyveromyces marxianus* (accession number AP012217; 74% identity to *S. cerevisae* SFA1); and *Debaryomyces hansenii* (accession number: XM_461798; 69% identity to *S. cerevisae* SFA1) and *Aspergillus oryzae* (accession number XM_001823291; 64% identity to *S. cerevisae* SFA1).

FNR transcriptional dual regulators are transcription regulators responsive to oxygen content. FNR is an anaerobic regulator that represses the expression of PDHc. Accordingly, reducing FNR will result in an increase in PDHc expression. FNR homologs and variants are known. For examples, such homologs and variants include, for example, DNA-binding transcriptional dual regulator, global regulator of anaerobic growth (*Escherichia coli* W3110) gi|1742191|dbj|BAA14927.1|(1742191); DNA-binding transcriptional dual regulator, global regulator of anaerobic growth (*Escherichia coli* K12) gi|16129295|ref|NP_415850.1|(16129295); DNA-binding transcriptional dual regulator, global regulator of anaerobic growth (*Escherichia coli* K12) gi|1787595|gb|AAC74416.1|(1787595); DNA-binding transcriptional dual regulator, global regulator of anaerobic growth (*Escherichia coli* W3110) gi|89108182|ref|AP 001962.1|(89108182); fumarate/nitrate reduction transcriptional regulator (*Escherichia coli* UTI89) gi|162138444|ref|YP_540614.2|(162138444); fumarate/nitrate reduction transcriptional regulator (*Escherichia coli* CFT073) gi|161486234|ref|NP_753709.2|(161486234); fumarate/nitrate reduction transcriptional regulator (*Escherichia coli* 0157:H7 EDL933) gi|15801834|ref|NP_287852.1|(15801834); fumarate/nitrate reduction transcriptional regulator (*Escherichia coli* APEC O1) gi|117623587|ref|YP_852500.1|(117623587); fumarate and nitrate reduction regulatory protein gi|71159334|sp|P0A9E5.1|FNR ECOLI (71159334); transcriptional regulation of aerobic, anaerobic respiration, osmotic balance (*Escherichia coli* 0157:H7 EDL933) gi|12515424|gb|AAG56466.1|AE005372_11(12515424); Fumarate and nitrate reduction regulatory protein gi|71159333|sp|P0A9E6.1|FNR_ECOL6(71159333); Fumarate and nitrate reduction Regulatory protein (*Escherichia coli* CFT073) gi|26108071|gb|AAN80271.1|AE016760_130(26108071); fumarate and nitrate reduction regulatory protein (*Escherichia coli* UTI89) gi|91072202|gb|ABE07083.1|(91072202); fumarate and nitrate reduction regulatory protein (*Escherichia coli* HS) gi|157160845|ref|YP_001458163.1|(157160845); fumarate and nitrate reduction regulatory protein (*Escherichia coli* E24377A) gi|157157974|ref|YP_001462642.1|(157157974); fumarate and nitrate reduction regulatory protein (*Escherichia coli* E24377A) gi|157080004|gb|ABV19712.1|(157080004); fumarate and nitrate reduction regulatory protein (*Escherichia coli* HS) gi|157066525|gb|ABV05780.1|(157066525); fumarate and nitrate reduction regulatory protein (*Escherichia coli* APEC O1) gi|115512711|gb|ABJ00786.1| (115512711); transcription regulator Fnr (*Escherichia coli* 0157:H7 str. Sakai) gi|13361380|dbj|BAB35338.1| (13361380) DNA-binding transcriptional dual regulator (*Escherichia coli* K12) gi|16131236|ref|NP_417816.1| (16131236), to name a few, each sequence associated with the accession number is incorporated herein by reference in its entirety.

Butyryl-coA dehydrogenase is an enzyme in the protein pathway that catalyzes the reduction of crotonyl-CoA to butyryl-CoA. A butyryl-CoA dehydrogenase complex (Bcd/EtfAB) couples the reduction of crotonyl-CoA to butyryl-CoA with the reduction of ferredoxin. Depending upon the organism used a heterologous butyryl-CoA dehydrogenase can be engineered for expression in the organism. Alternatively, a native butyryl-CoA dehydrogenase can be overexpressed. Butyryl-coA dehydrogenase is encoded in *C. acetobuylicum* and *M. elsdenii* by bcd. BCD homologs and variants are known. For examples, such homologs and variants include, for example, butyryl-CoA dehydrogenase (*Clostridium acetobutylicum* ATCC 824) gi|15895968|ref|NP_349217.1|(15895968); Butyryl-CoA dehydrogenase (*Clostridium acetobutylicum* ATCC 824) gi|15025744|gb|AAK80657.1|AE007768_11(15025744); butyryl-00A dehydrogenase (*Clostridium botulinum* A str. ATCC 3502) gi|148381147|ref|YP_001255688.1| (148381147); butyryl-00A dehydrogenase (*Clostridium botulinum* A str. ATCC 3502) gi|148290631|emb|CAL84760.1|(148290631), each sequence associated with the accession number is incorporated herein by reference in its entirety. BCD can be expressed in combination with a flavoprotien electron transfer protein. Useful flavoprotein electron transfer protein subunits are expressed in *C. acetobutylicum* and *M. elsdenii* by a gene etfA and etfB (or the operon etfAB). ETFA, B, and AB homologs and variants are known. For examples, such homologs and variants include, for example, putative a-subunit of electron-transfer flavoprotein gi|1055221|gb|AAA95970.1|(1055221); putative b-subunit of electron-transfer flavoprotein gi|1055220|gb|AAA95969.1|(1055220), each sequence associated with the accession number is incorporated herein by reference in its entirety.

In yet other embodiment, in addition to any of the foregoing and combinations of the foregoing, additional genes/enzymes may be used to produce a desired product. For example, the following table provide enzymes that can be combined with the MEC pathway enzymes for the production of 1-butanol from acetyl phosphate ("−" refers to a reduction or knockout; "+" refers to an increase or addition of the referenced genes/polypeptides):

| Enzyme | Exemplary Gene(s) | 1-butanol | Exemplary Organism |
|---|---|---|---|
| Ethanol Dehydrogenase | adhE | − | *E. coli* |
| Lactate Dehydrogenase | ldhA | − | *E. coli* |
| Fumarate reductase | frdB, frdC, or frdBC | − | *E. coli* |
| Oxygen transcription regulator | fnr | − | *E. coli* |
| Phosphate acetyltransferase | pta | − | *E. coli* |

| Enzyme | Exemplary Gene(s) | 1-butanol | Exemplary Organism |
|---|---|---|---|
| Formate acetyltransferase | pflB | − | E. coli |
| acetyl-coA acetyltransferase | atoB | + | C. acetobutylicum |
| acetoacetyl-coA thiolase | thl, thlA, thlB | + | E. coli, C. acetobutylicum |
| 3-hydroxybutyryl-CoA dehydrogenase | hbd | + | C. acetobutylicum |
| crotonase | crt | + | C. acetobutylicum |
| butyryl-CoA dehydrogenase | bcd | + | C. acetobutylicum, M. elsdenii |
| electron transfer flavoprotein | etfAB | + | C. acetobutylicum, M. elsdenii |
| aldehyde/alcohol dehydrogenase(butyraldehyde dehydrogenase/butanol dehydrogenase) | adhE2 bdhA/bdhB aad | + | C. acetobutylicum |
| crotonyl-coA reductase | ccr | + | S. coelicolor |
| trans-2-enoyl-CoA reductase | Ter | + | T. denticola, F. succinogenes |

* knockout or a reduction in expression are optional in the synthesis of the product, however, such knockouts increase various substrate intermediates and improve yield.

The disclosure includes recombinant microorganisms that comprise at least one recombinant enzymes of the MEC pathway set forth in FIG. 1. For example, chemoautotrophs, photoautotroph, and cyanobacteria can comprise native F/Xpk enzymes, accordingly, overexpressing FPK, XPK, or F/Xpk by tying expression to a non-native promoter can produce sufficient metabolite to drive the MEC pathway when combined with the other appropriate enzymes of FIG. 1. Additional enzymes can be recombinantly engineered to further optimize the metabolic flux, including, for example, balancing ATP, NADH, NADPH and other cofactor utilization and production.

In another embodiment, a method of producing a recombinant microorganism that comprises optimized carbon utilization including a MEC pathway to convert methanol, methane or formaldehyde to acetyl-phosphate, acetyl-CoA or other metabolites derived therefrom including, but not limited to, 1-butanol, 2-pentanone, isobutanol, n-hexanol and/or octanol is provided. The method includes transforming a microorganism with one or more recombinant polynucleotides encoding polypeptides selected from the group consisting of a phosphoketolase (e.g., Fpk, Xpk, or Fpk/Xpk), a transaldolase (e.g., Tal), a transketolase (e.g., Tkt), ribose-5-phosphate isomerase (e.g., Rpi), a ribulose-5-phosphate epimerase (e.g., Rpe), a hexulose-6-phsophate synthase (e.g., Hps), a hexulose-6-phsophate isomerase (e.g., Phi), a dihydroxyacetone synthase (e.g., Das), a fructose-6-phosphate aldolase (e.g., Fsa), a methanol dehydrogenase (e.g., Mdh), a keto thiolase or acetyl-CoA acetyltransferase activity, hydroxybutyryl CoA dehydrogenase activity, crotonase activity, crotonyl-CoA reductase or butyryl-CoA dehydrogenase activity, trans-enoyl-CoA reductase and alcohol dehydrogenase activity.

In another embodiment, as mentioned previously, a recombinant organism as set forth in any of the embodiments above, is cultured under conditions to express any/all of the enzymatic polypeptide and the culture is then lysed or a cell free preparation is prepared having the necessary enzymatic activity to carry out the pathway set forth in FIG. 1 and/or the production of a 1-butanol, isobutanol, n-hexanol, octanol, 2-pentanone among other products.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

To construct an in vitro system, all the MEC enzymes were acquired commercially or purified by affinity chromatography, tested for activity, and mixed together in a properly selected reaction buffer. AcP concentration is measured using an end-point colorimetric hydroxamate method.

Figure 9A:
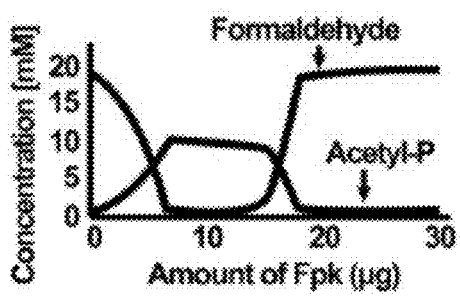
FIG. 9A-B shows a Kinetic Trap in MEC. (A) Using COPASI, a region where MEC reaches stoichimetric yield is predicted. At high Fpk amounts, a kinetic trap occurs. (B) This simulation was experimentally confirmed using in vitro assays of the core MEC pathway.
Figure 9B:
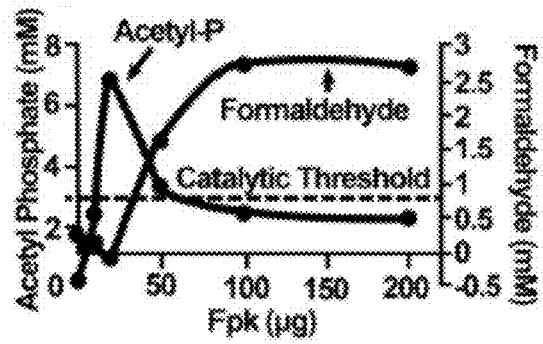

The core portion of MEC includes the conversion of formaldehyde to acetyl-phosphate which is catalyzed by Hps, Phi, Tkt, Tal, Rpe, Rpi, and Fpk. The kinetics of Fpk and acetyl-phosphate production were analyzed. FIG. 9 shows the kinetics of the relationship. This kinetic trap was demonstrated using in vitro purified enzymes. For this system, the amount of phosphoketolase (F/Xpk) was varied as the rest of the enzymes were kept constant. Acetyl-phosphate was measured by the hydroxylamine method and formaldehyde was measured using the Purpald reagent.

Figure 10:
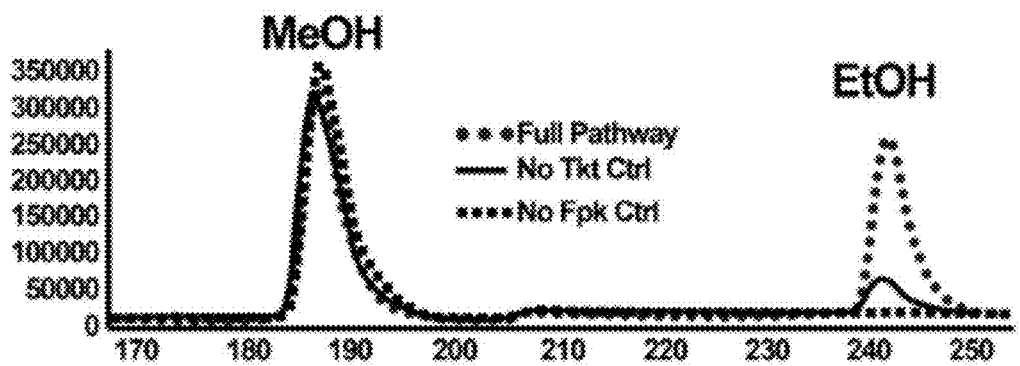
FIG. 10 shows the conversion of $^{13}$C-methanol to $^{13}$C-ethanol using the MEC pathway.
Figure 11:
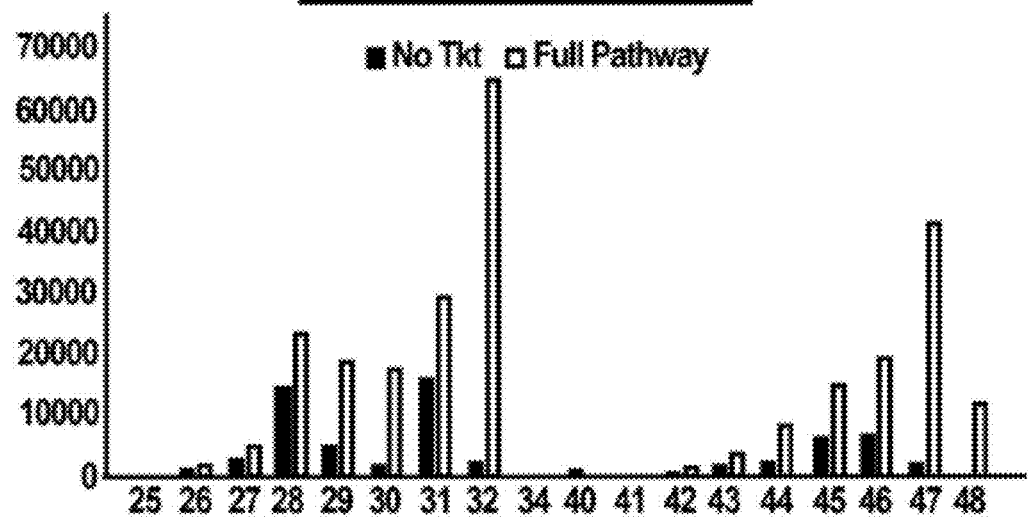
FIG. 11 shows a mass spec profile of $^{13}$C labeled EtOH.
Figure 18:
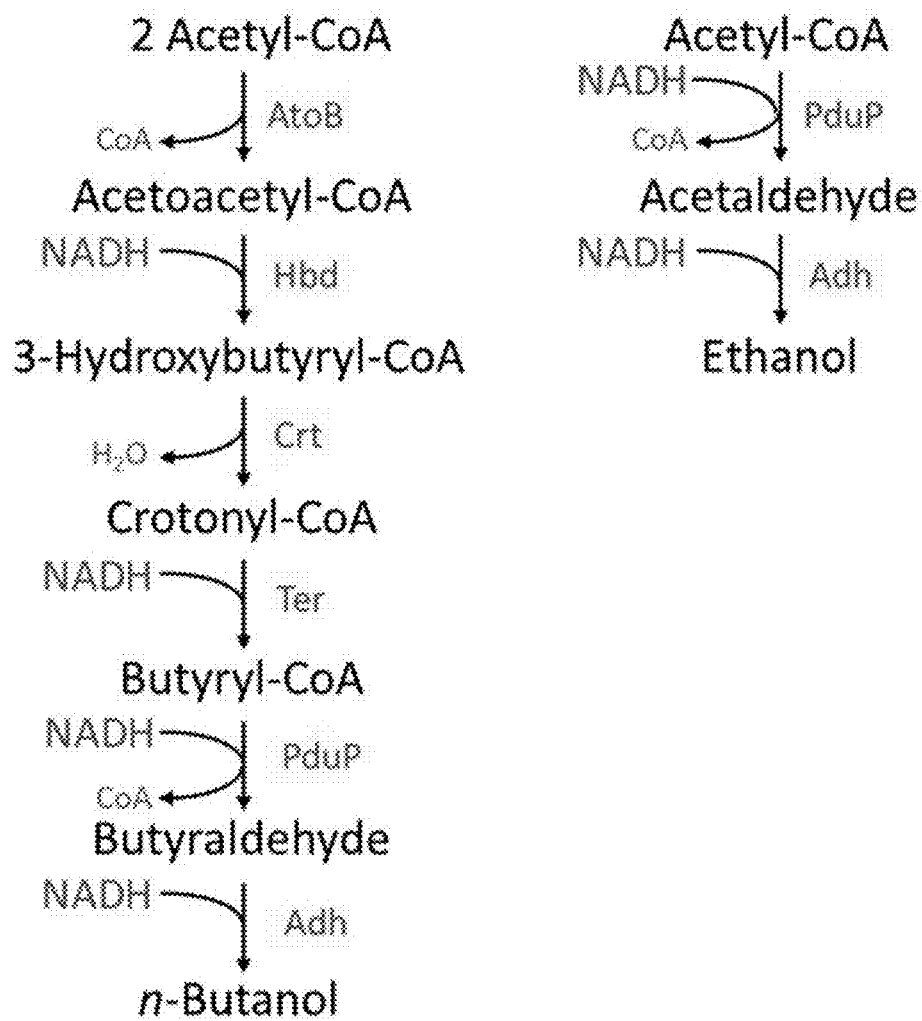
FIG. 18 shows Acetyl-CoA can be reduced with NADH to form either n-butanol or ethanol.

FIG. 10 shows a $^{13}$C labeling experiment to determine the carbon pathway in the MEC pathway. The carbon of MeOH was $^{13}$C labeled and the MEC pathway was run in vitro either in "full" or lacking Fpk or Tkt. When the full pathway was run, a large peak was identified for 13C labeled EtOH. However, in the absence of tkt a smaller peak of labeled EtOH (approximately 20% of the full pathwyway) and in the absence of Fpk no EtOH was labeled. This indicates the labeled carbon of MeOH was effectively converted to EtOH in the MEC pathway. FIG. 11 shows the MS profile for the ethanol produced showed significant 48 peak corresponding to double labeled ethanol. The "no Tkt" control served to demonstrate the importance of the carbon rearrangement steps in the cycle.

After demonstrating the feasibility of the pathway using in vitro enzymatic systems, aspects of the pathway were engineered into Escherichia coli. Xylose was used because it avoids the complication of various glucose-mediated regulations, including the use of phosphotransferase system for transport. In order to engineer a preliminary pathway for xylose in E. coli, two enzymes were overexpressed: F/Xpk (encoded by f/xpk from Bifidobacterium adolescentis) and Fbp (encoded by E. coli fbp). Other enzymes were natively expressed in E. coli under the experimental conditions. The genes encoding these two enzymes were cloned on a high copy plasmid (pIB4) under the control of the PLlacO-1 IPTG-inducible promoter. The plasmid was transformed into three E. coli strains: JCL16 [wild type], JCL166[ΔldhA, ΔadhE, Δfrd], and JCL 118 [ΔldhA, ΔadhE, Δfrd, ΔpflB]. The latter two strains were used to avoid pathways competing. The expression of F/Xpk and Fbp was demonstrated by protein electrophoresis and their activities were confirmed by enzyme assays. After an initial aerobic growth phase for cell growth, high cell density cells were harvested and re-suspended in anaerobic minimal medium with xylose at a final $OD_{600}$ of 9. Anaerobic conditions were used to avoid the oxidation of acetate through the TCA cycle. HPLC was used for monitoring xylose consumption and organic acids formation. The wild-type host (JCL16) produced a mixture of lactate, formate, succinate, and acetate from xylose, and the yield on acetate was low at about 0.4 acetates produced per xylose consumed, indicating that EMP and other fermentative pathways out-competed the synthetic pathway. By removing several fermentative pathways by the Δldh, ΔadhE, and Δfrd knockouts in JCL166, the yield was increased to 1.1 acetate/xylose consumed. After further deleting pflB in JCL118, the yield reach the highest level of 2.2 acetates/xylose consumed, approaching the theoretical maximum of 2.5 mole of acetate/mole of xylose. Some succinate remained, presumably due to succinate dehydrogenase left over from the aerobic growth phase.

One useful enzyme in the pathway is the irreversible Fpk/Xpk which can split F6P or xylulose-5-phosphate into AcP and E4P or G3P, respectively. This class of enzymes has been well-characterized in heterofermentative pathways from Lactobacillae and Bifidobacteria. In Lactobacillae, glucose is first oxidized and decarboxylated to form $CO_2$, reducing power, and xylulose-5-phosphate, which is later split to AcP and G3P. Xpks have also been found in Clostridium acetobutylicum where up to 40% of xylose is degraded by the phosphoketolase pathway. Bifidobacteria, utilizes the Bifid Shunt, which oxidizes two glucoses into two lactates and three acetates. This process yields increase the ATP yield to 2.5 ATP/glucose. In both variants G3P continues through the oxidative EMP pathway to form pyruvate. Thus these pathways are still oxidative and are not able to directly convert glucose to three two-carbon compounds.

Enzyme abbreviations and EC no. are listed in Table A.

TABLE A

Enzyme abbreviations and EC numbers:

| Name | | Abbrev. | EC# | Verified Source |
|---|---|---|---|---|
| F6P-Phosphoketolase | 1a | Fpk | 4.1.2.22 | B. adolescentis* |
| X5P-Phosphoketolase | 1b | Xpk | 4.1.2.9 | L. plantarum |
| Transaldolase | 2 | Tal | 2.2.1.2 | E. Coli |
| Transketolase | 3 | Tkt | 2.2.1.1 | E. Coli |
| Triose Phosphate Isomerase | 6 | Tpi | 5.3.1.1 | E. Coli |
| Fructose 1,6 Bisphosphatase | 8 | Fbp | 3.1.3.11 | E. Coli |
| Fructose 1,6 bisphosphate Aldolase | 7 | Fba | 4.1.2.13 | E. Coli |
| Ribose-5-phosphate isomerase | 4 | Rpi | 5.3.1.6 | E. Coli |
| Ribulose-3-phosphate epimerase | 5 | Rpe | 5.1.3.1 | E. Coli |
| Glucokinase | | Glk | 2.7.1.2 | E. Coli |
| Glucose-6-phosphate Dehydrogenase | | Zwf | 1.1.1.49 | E. Coli |
| Phopshoglucose Isomerase | | Pgi | 5.3.1.9 | E. Coli |
| Acetate Kinase | | Ack | 2.7.2.1 | E. Coli |
| Hexulose-6-phosphate synthase | | Hps | 4.1.2.43 | M. capsulatus |
| Hexulose-6-phosphate isomerase | | Phi | 5.3.1.27 | M. Capsulatus |
| Dihydroxyacetone synthase (formaldehyde transketolase) | | Das | 2.2.1.3 | C. boindii |
| Phosphotransacetylase | | Pta | 2.3.1.8 | E. Coli |
| Methanol dehydrogenase | | Mdh | 1.1.99.37 | B. Methanolicus |

Thermodynamics of MEC Enzymes.

The change in standard Gibbs free energy ($\Delta rG'^o$ in kJ/mol) for each step was calculated using eQuilibrator with pH=7.5 and ionic strength=0.2 M to represent E. coli's cytosolic environment. All values were obtained using the difference of the standard Gibbs free energy of formation between the products and reactants. Since standard state is set at 1 M for all reactants (including water), some of the values do not correspond with experimentally verified data.

Combination of the Underlying F/Xpk Pathway with the Dihydroxyacetone (DHA) Pathway.

The F/Xpk pathway can be combined with the DHA pathway, which is analogous to the RuMP pathway for assimilation of formaldehyde. The pathways are shown in FIG. 1. This pathway includes the action of the gene fructose-6-phosphate aldolase (fsa) which has been characterized from E. coli. Though the native activity of this enzyme was reported to have a high $K_m$, recent design approaches have improved affinity towards DHA. The overall pathway from two methanol to ethanol is favorable with a $\Delta rG'^o = -68.2$ kJ/mol.

Construction of In Vivo Pathways.

For the in vivo production of acetate from xylose, the plasmid pIB4 was made using pZE12 as the vector, F/Xpk from B. adolenscentis and Fbp from E. coli (JCL16 gDNA). The strains JCL16, JCL166, and JCL118 were constructed (see, e.g., Int'l Patent Publication No. WO 2012/099934). This was done using the P1 phage transduction method with the Keio collection as the template for single-gene knockouts. The strains JCL166 and JCL118 were transformed with pIB4. Single colonies were grown in LB medium overnight and inoculated into fresh LB+1% xylose culture the next day. After reaching an OD=0.4-0.6, the strains were induced with 0.1 mM IPTG. After overnight induction, the cells were concentrated ten-fold and resuspended anaerobically in M9 1% xylose. A small portion of the induced cells was extracted for HIS-tag purification to verify the activity of F/Xpk and Fbp, and the rest was incubated anaerobically overnight for acetate production. The final mixture was spin down at 14,000 rpm, and a diluted supernatant was run on HPLC to measure xylose and organic acid concentration.

Phosphoketolase in Nature.

Phosphoketolase have been known to exist in many bacteria such as *Bifidobacteria* for decades. *Bifidobacteria* make up a large portion of the beneficial flora in human's stomach, are used in the fermentation of various foods from yogurt to kimchi, and are even sold in a dehydrated pill form. These bacteria contain a unique pathway that can ferment sugars to a mixture of lactate and acetate. By using the F6P/X5P phosphoketolase enzyme, they are able to obtain more ATP than other fermentative pathways at 2.5 ATP/glucose.

In Vitro Methods

Chemicals and Reagents.

All reagents were purchased from Sigma-Aldrich (St. Louis, Mo., USA) unless otherwise stated. The following enzymes were also purchased from Sigma-Aldrich: hexokinase (*S. cerevisiae*), phosphoglucose isomerase (*S. cerevisiae*), glucose-6-phosphate dehydrogenase (*S. cerevisiae*), alcohol oxidase (*Pichia pastoris*). Alcohol dehydrogenase (*S. cerevisiae*) and formate dehydrogenase (*C. boindii*) were purchased from Worthington Biochemical Corporation (Lakewood, N.J., USA).

Cloning and Purification MCC Enzymes.

All enzymes were cloned onto the pQE9 (Qiagen, Valencia, Calif.) backbone and purified on a Ni-NTA column. Large scale purification (500 mL) typically produced about 10-50 mg of for each enzyme.

Plasmid Construction.

Plasmids used in enzyme purification were constructed either on the pQE9 (Qiagen, Hilden, Germany) or pCDF-Duet1 (EMD Chemicals Inc., NJ) vectors which contained a Histidine (His) tag, IPTG-inducible promoter, and high-copy origin of replication. The plasmids are maintained with 100 mg/L ampicillin.

Enzyme Purification.

Enzymes were expressed in IPTG-inducible plasmids with 6× histidine tags in transformed in *E. coli* strain XL1-Blue or BL21(DE3). Induction was accomplished with 0.1 mM IPTG. Enzymes were purified using the QIAExpressionist purification procedure for proteins under native conditions. Enzyme concentration was determined by the method of Bradford using a commercial dye (Thermo Fisher Scientific, Waltham, Mass., USA).

In Vitro Assays for Each Enzyme.

All assays were conducted at 25° C. unless otherwise stated.

Conditions for Hps-Phi Assays:

In 500 µL reaction contained 50 mM Tris buffer pH 7.5, 5 mM $MgCl_2$, 0.2 mM NADP+, 5 mM R5P, 5 mM formaldehyde, 6.1 µg Pgi, 1.1 µg Zwf, 48 µg Rpi. In Phi assays, 9.6 µg of Hps and 0.0048 µg Phi were used. In Hps assays, 47 µg Phi and 1.9 µg Hps were used. The assays followed the generation of NADPH at 340 nm. The assays were initiated by the addition of R5P.

Conditions for F/Xpk Assay:

A 550 µL reaction contained 50 mM potassium phosphate buffer pH 7.5, 5 mM $MgCl_2$, 0.2 mM NADP+, 1 mM TPP, 0.2 mM ADP, 20 mM glucose, 10 mM F6P, 1.6 µg F/Xpk, 30 µg Ack, 2 Units Glk, 2 Units Zwf. The production of NADPH was followed at 340 nm. Similar assay was done to measure Xpk activity by adding 10 mM R5P as substrate with 10 µg each of Rpi and Rpe.

Conditions for Tal, Tkt, Rpe, Rpi Assays:

A 550 µL reaction mixture contains 5 mM R5P, 50 mM Gly-Gly buffer pH 8.5, 5 mM $MgCl_2$, 1 mM TPP, 0.26 mM NADP+, 0.4 U Zwf, 0.4 U Pgi. For coupling reactions, high enzyme amounts were used: 260 µg Tal, 8 µg Tkt, 14 µg Rpe, and 12 µg Rpi. The tested enzyme in each assay was used at the following levels: 0.5 ug Tal, 0.3 µg Tkt, 0.2 µg Rpe, 0.1 µg Rpi. The production of NADPH was measured at 340 nm.

Conditions for PduP (Bm) Assay:

A 500 µL reaction contained 50 mM Tris buffer pH 7.5, 5 mM $MgCl_2$, 0.3 mM NADH, 1 mM AcCoA, 25 µg PduP (Bm). The assays followed the consumption of NADH at 340 nm. The assays were initiated by the addition of AcCoA.

Conditions for PduP (Se) Assay:

A 500 µL reaction contained 50 mM Tris buffer pH 7.5, 5 mM $MgCl_2$, 0.3 mM NADH, 1 mM Butyryl-CoA, 10 µg PduP (Se). The assays followed the consumption of NADH at 340 nm. The assays were initiated by the addition of Butyryl-CoA.

Conditions for Pta Assays:

A 550 µL reaction contained 50 mM Tris buffer pH 7.5, 0.2 mM NADH, 2 mM acetyl-phosphate, 10 mM coenzyme A, 0.077 µg Pta and 44 µg PduP (Se). The decrease in NADH was followed at 340 nm.

Conditions for Hbd Assay:

A 550 µL reaction contained 50 mM potassium phosphate buffer pH 7.5, 5 mM $MgCl_2$, 0.2 mM NADH, 0.01 µg Hbd, 0.3 mM acetoacetyl-CoA. The decrease in NADH was followed at 340 nm.

Conditions for AtoB Assay:

A 550 µL reaction contained 50 mM potassium phosphate buffer pH 7.5, 5 mM $MgCl_2$, 0.2 mM NADH, 20 µg Hbd, 0.3 µg AtoB, 0.3 mM acetoacetyl-CoA. The decrease in NADH was followed at 340 nm.

Conditions for Mdh Assays:

A 500 µL reaction contained, 500 mM methanol, 1 mM NAD+, 50 mM diglycine buffer pH 8.0, 5 mM $MgCl_2$. The assays followed the generation of NADH at 340 nm. The assays were initiated by the addition of 10-200 µg of alcohol dehydrogenase, depending on the organism.

Conditions for Adh:

A 500 µL reaction contained 50 mM Gly-Gly buffer pH 8.5, 2 mM acetaldehyde, 5 mM $MgCl_2$, 1 mM NADH, and 0.01 U Adh (Sc). The decrease in NADH was followed at 340 nm.

GC-MS and GC-FID Analysis.

All columns and instruments were purchased from Agilent Technologies (Santa Clara, Calif., USA). GC/MS data were obtained from a 6890/5973 GC/MS. An HP-FFAP column was used to reproducibly quantitate acetic acid. A three-point plus zero-intercept standard curve was generated with $R^2=0.998$ up to 5 mM acetic acid and RSD 3.5-7% (N=3, SSD) to ensure reliable quantitation. Acetic acid has a strong mass peak at its molecular weight 60 in GC/MS analysis which is free of surrounding peaks. Thus, 60, 61 & 62 mass peaks were used to quantify the isotopes of acetic acid. An inlet temperature of 250° C. was used. Oven temperature started at 70° C. and held for one minute, followed by a ramp at 20° C./min and 2 minute hold at 240° C. Injection of 0.2 µL in splitless mode with constant pressure of 10 psi at the inlet was used.

Analysis of methanol to ethanol and butanol experiments was carried out using a DB-624UI (GC/MS) or DB-FFAP (GC-FID) column. An inlet temperature of 225° C. was used. Oven temperature started at 40° C. for 3 minutes, followed immediately by a ramp 45° C./min to 235° C. and hold for 3 minutes. Injection of 1 μL with split ratio of 25 in constant pressure mode with 9.52 psi at the inlet was used. For mass scatters of alcohol samples, the GC-MS was used. GC-FID was typically used for quantification of alcohols, though GC-MS also produced reproducible linear standard curves with ethanol and n-butanol.

Thermodynamic Profile of MCC.

Using the Equilibrator website (equilibrator.weizmann.ac.il), all reactions (Mdh, Hps, Phi, F/Xpk, Tkt, Tal, Rpe, Rpi, Pta, Ato, Hbd, Crt, Ter, PduP, Adh) were set to pH 7.5, ionic strength of 0.2 mM and standard concentrations. For non-standard conditions, a theoretical set of concentrations for all intermediates.

Robustness of MCC by Ensemble Model and Robustness Analysis (EMRA).

EMRA is a technique for determining how likely it is that perturbations in enzyme parameters, including enzyme amount, will interrupt the nature of a steady state. A model including the effects of Fpk was used. A reference steady state was chosen to represent MCC operation. A total of 200 parameter sets were generated and perturbations from 0.1-fold to 10-fold for each enzyme were investigated. The robustness of the system at each point for each system was reported and YR,M is the fraction of the 200 parameter sets that are robust at each point.

Formaldehyde to Acetate Assay with F/Xpk Variation.

A 200 μL reaction contained 50 mM Tris-HCl buffer pH=7.5, 25 mM potassium phosphate buffer, 10 mM $MgCl_2$, 48 μg Tkt, 76 μg Tal, 24 μg Rpe, 70 μg Hps, 15 μg Phi, 20 μg Rpi, 1 mM R5P, 0.5 mM thiamine pyrophosphate, 5 mM 13C-formaldehyde, 0.1 mM ATP, 5.4 μg Ack, 2.5 U hexokinase, and 5 mM glucose. Various amounts of F/Xpk were used. The reaction time for formaldehyde to acetate assays was 3 hours and the reactions were conducted at room temperature.

Continuous Ethanol Production:

A 200 μL reaction contained 50 mM Potassium Phosphate pH 7.5, 0.2 mM NAD+, 0.2 mM CoA, 10 mM $MgCl_2$, and 1 mM TPP. The enzyme amounts were: 30 μg Hps, 10 μg Phi, 100 μg Tkt, 60 μg Tal, 10 μg Rpi, 10 μg Rpe, 15 μg F/Xpk, 10 μg Pta, 50 μg PduP (Bm), 0.01 U Adh, and 0.1 U Fdh. The initial substrates were 6 mM 13C-formaldehyde, 0.5 mM R5P, 10 mM sodium formate. The same amount of substrates were feed at 1 hour and 2 hours. Tal was excluded for the control. Samples were analyzed by GC-MS every 30 minutes for three hours.

For Methanol to Ethanol Assays.

The buffer conditions were changed since methanol oxidation by alcohol dehydrogenase is extremely slow at pH 7.5. Diglycine buffer (pH 8.5) was chosen as a compromise between optimal activity for Mdh and F/Xpk. Since F/Xpk is slower at pH 8.5, more enzyme was added to compensate. A 550 μL reaction contained 100 mM Diglycine buffer pH=8.5, 1 mM dipotassium phosphate, 10 mM $MgCl_2$, 1 mM NAD+, 1 mM thiamine pyrophosphate, 0.2 mM Coenzyme A, 200 mM 13C-methanol, 4 mM F6P. The enzyme amounts were: 55 μg Tkt, 431 μg Tal, 53 μg Rpe, 79 μg Rpi, 393 μg Hps, 431 μg Phi, 344 μg Fpk, 55 μg Pta, 297 μg PduP (Bm), 2.75 mg Adh. Reaction was carried out at 37° C. At each time point, 120 μL of sample was taken out and mixed with 12 μL of 8 M urea to quench the reaction. Samples were subject to filtration (Costar Centrifuge Devices, cellulose acetate, 0.22 μm, Corning, Amsterdam, The Netherlands) if precipitation occurs. After 2 minutes, 120 μL of 1 g/L 1-pentanol were added as internal standard for GC analysis. The samples were kept in −20° C. before further analysis.

For Methanol to n-Butanol Assays.

The buffer and components of reaction mixture were identical to methanol to ethanol assay except for the enzymes. In a 550 μL reaction, the following enzymes were added: 55 μg Tkt, 431 μg Tal, 53 μg Rpe, 79 μg Rpi, 393 μg Hps, 431 μg Phi, 344 μg Fpk, 55 μg Pta, 743 μg AtoB, 88 μg Hbd, 38 μg Crt, 30 μg Ter, 59 μg PduP (Se), and 2.75 mg Adh (Sc). The procedure of sample preparation for GC is identical to methanol to ethanol assay.

Analytical Methods.

Individual assays followed spectrophotometrically using a Beckman Coulter DU 800 (Beckman Coulter, Pasadena, Calif., USA) or Agilent 8453 UV-Vis Spectrophotometer (Agilent Technologies, Santa Clara, Calif., USA). Acetic acid, ethanol, and n-butanol were analyzed by GC-FID or GC-MS (Agilent Technologies, Santa Clara, Calif., USA).

Sugar Phosphate Analysis.

Sugar phosphates were analyzed by a modified method from Groussac et al. Thermo ICS5000+ with a Coulochem III detector and a CarboPac PA1 guard and analytical column, the flow rate was set at 1.0 mL/min with Buffer A (50 mM NaOH) and Buffer B (50 mM NaOH/500 mM NaAce). The injection volume was 10 μL. The column was equilibrated for 3 hours with 100% A. From 0-25 minutes, Buffer B was linearly increased to 20%, from 25-45 min Buffer B was linearly increased to 75%, from 45-46 min Buffer B was linearly dropped back to 0% and held for another 10 minutes to re-equilibrate the column.

Predicting $^{13}$C-Tracing with Time-Domain Integration.

A system modelling the conversion of 13C-formaldehyde and priming amounts of unlabeled R5P to acetic acid was generated in MATLAB. Michaelis-Menten equations modeling the effect of each enzyme were chosen from based on number of products, substrates and reversibility of each reaction. Parameters for each reaction were chosen at random. Vmax parameters were chosen uniformly from a 3-fold range while Km parameters were chosen from a 10-fold range. Phosphoketolase Vmax parameters were not chosen at random but assigned as and varied over a range. Xpk:Fpk activity was 1:7, as previously reported. The simulation time was chosen to be representative of the in vitro experiment performed. Keq values for reversible reactions were chosen to be realistic, based on thermodynamics.

The effects of carbon labelling were incorporated by charting the locations of labeled ions and assigning a different compound for each different isotope. The saturation of each enzyme was found by calculating the total amount of each compound, while the flux interconverting each isotope was calculated as a fraction of total flux, depending on the abundance of the isotope generating that flux.

Kinetic Analysis.

The overall specific productivity (μmol/min/mg total protein) of the pathway production is calculated by a modification of Bar-Even et al.

To demonstrate the feasibility of MEC (aka MCC), experiments were initial focused on the core portion from formaldehyde to acetate using purified enzymes. Each enzyme was demonstrated to have activity in individual assays. Similar to other non-linear metabolic cycles (like TCA or CBB), an initial pool of intermediates was needed to prime the pathway. 13C-labeled formaldehyde was used to detect the carbon flow. According to MCC, double-labeled acetic acid (MW=62) was expected if 13C-formaldehyde was catalytically converted and the ribulose-5-phosphate was regenerated. Unfortunately, after buffer optimization even this core pathway could not be demonstrated. No difference in double labeled acetate was observed with or without carbon rearrangement enzymes.

Robustness of MCC to Enzyme Variation.

Figure 19:
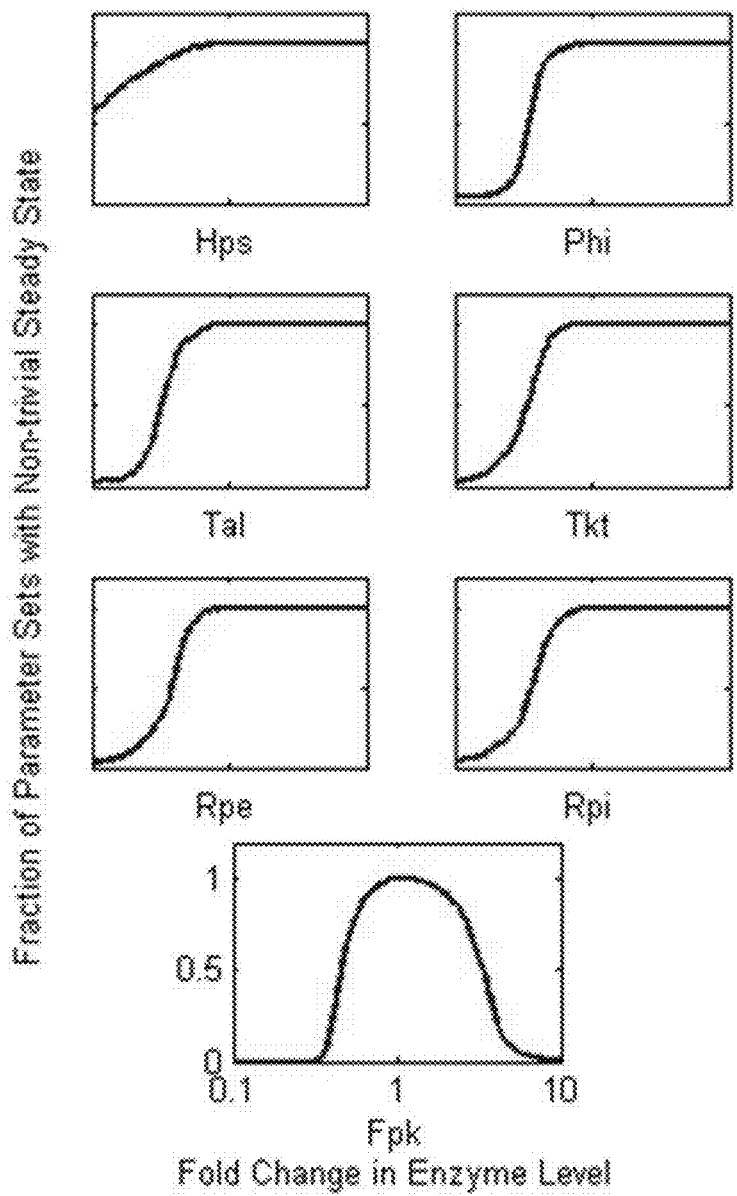
FIG. 19 shows the EMRA analysis indicates that for phosphoketolase, very high activity levels will cause the cycle to have a change in the nature of its steady state (bifurcation). Other enzymes cause this only when they are present at low levels. Source files can be included in future submissions.

The failure of these initial tests prompted an examination of the robustness of the pathway. Since the cycle enzymes involve bifurcating branches, unbalanced enzyme activities may have led to failure of the cycle. Ensemble Modeling for Robustness Analysis (EMRA) was used to determine if the cycle is robust against loss of steady-state due to non-linear effects. The analysis showed that the MCC cycle is most robust using intermediate levels of phosphoketolase (FIG. 13A), and will produce less acetyl-phosphate as the enzyme amount increases or decreases. At excessive levels of phosphoketolase, a kinetic "trap" occurs that significantly diminishes the total acetyl-phosphate produced since an accumulation of G3P or E4P occurs. This phenomenon was only predicted for phosphoketolase, while other enzymes were immune to this trap at high amounts (FIG. 19). To further investigate the kinetic trap, the effect of increasing phosphoketolase on conversion of $^{13}$C-formaldehyde and unlabeled R5P to acetic acid was simulated (FIG. 13B). All enzymes were modeled using Michaelis-Menten kinetics and a batch simulation was solved using a set of ordinary differential equations in Matlab. Enzyme parameters were chosen at random except for Vmax of phosphoketolase which was varied systematically. The average of ten parameter sets was calculated and a maximum amount of acetic acid was predicted at intermediate levels F/Xpk.

Cell-Free Verification of Kinetic Trap.

To experimentally verify the kinetic trap, the amount of phosphoketolase was varied using 13C-formaldehyde and R5P as substrates to produce acetyl-phosphate. By using glucose phosphorylation to recycle the ADP, acetyl-phosphate was converted to acetate to enable GC-MS analysis (20). GC-MS allowed visualization of the distribution of 60, 61, and 62 acetate isotopes. The maximum amount of acetate was observed when F/Xpk was around 90 mg/L (FIG. 13C). Consistent with the previous simulations, increasing the amount of phosphoketolase above this observed maximum caused a twofold decrease in total acetic acid. Single and unlabeled acetic acid both increased at higher F/Xpk values since the initial R5P could isomerize to X5P. The total acetic acid and isotope distribution from the cell-free experiment matched the trend shown in the simulation as the amount of phosphoketolase is varied.

Demonstration of the Catalytic Cycle Using $^{13}$C Tracing.

Figure 20:
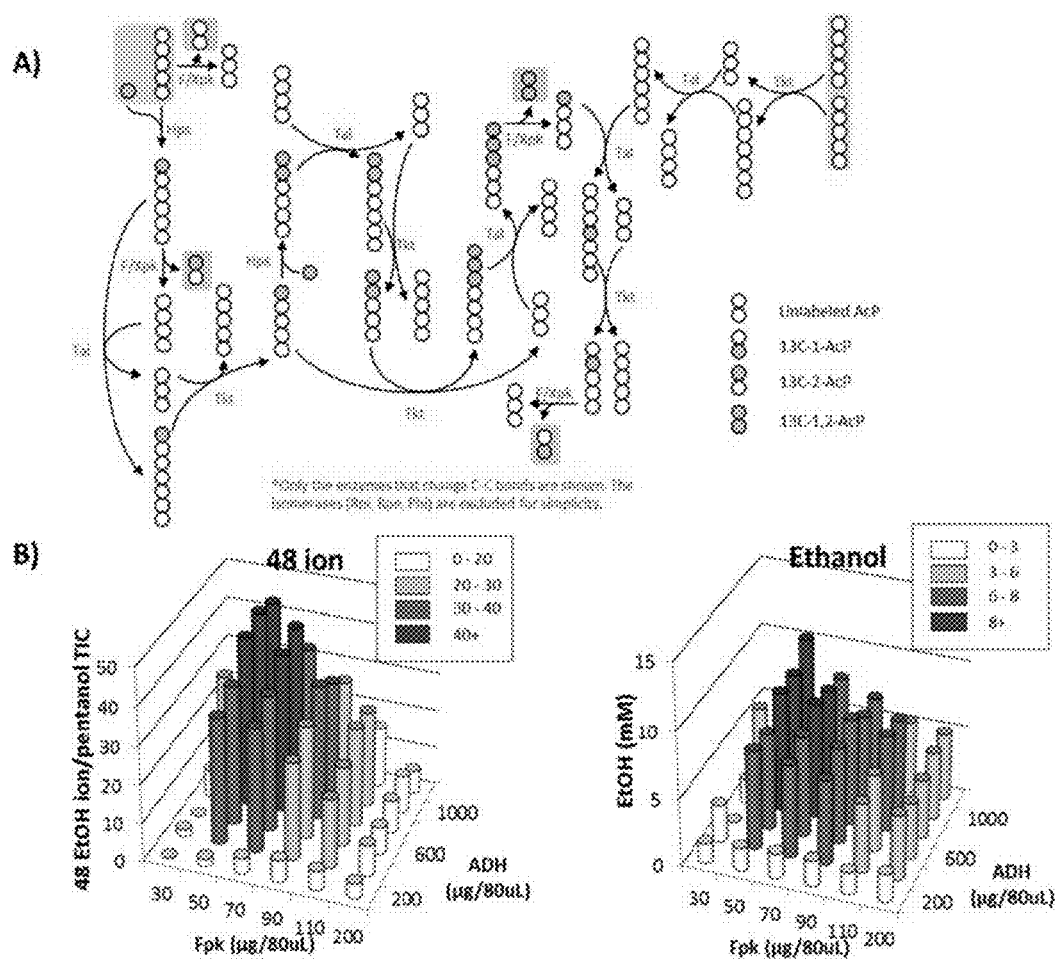
FIG. 20A-B shows (A) Schematic of $^{13}$C Tracing in MCC. All four isotopes of AcP are predicted if 13C-formaldehyde and unlabeled R5P are used as substrates. (B) Optimization of F/Xpk and Adh levels for increase production of double labeled [1,2-$^{13}$C]-ethanol using 48 ion and total ethanol amount as outputs. Effect of kinetic trap was observed when F/Xpk is higher than 50 µg/80 µL.

Since sugar phosphates must be added to prime the cycle, it is important establish whether the carbon in the final product comes from formaldehyde or the initial sugar phosphate pool. Having optimized the amount of F/Xpk in the core portion of MCC, the pathway was then extended further to ethanol using an external source of reducing equivalents. Phosphate acetyltransferase (Pta from *Bacillus subtilis*) was used to convert acetyl-phosphate to acetyl-coA, which can be reduced by a bifunctional alcohol dehydrogenase (AdhE). Yet, this enzyme is known to be oxygen labile and forms long rod-like structures, making in-vitro purification difficult. Instead, the oxygen-tolerant acylating acetaldehyde dehydrogenase (PduP) from *Salmonella enterica* can be used in a two-step reduction process via an aldehyde intermediate. A homologue of PduP from *Bacillus methanolicus* was used for converting acetyl-CoA to acetaldehyde, and a commercial Adh (*Saccharomyces cerevisiae*) for producing ethanol. Instead of starting from methanol, here formic acid and formate dehydrogenase were used from *Candida boidinii* to provide the NADH needed reduce acetyl-CoA to ethanol. This strategy allowed optimization of the pathway from formaldehyde to ethanol independently without the complication of Mdh. To verify that the carbon rearrangement is essential, the full pathway was compared to a control without Tal. $^{13}$Carbon labeled formaldehyde was used to track the carbon flow (FIG. 20). Since there is an initial pool of pentose phosphates, some unlabeled ethanol can form by cleavage of X5P. Additionally, a single pass of formaldehyde assimilation would produce a single labeled [2-13C]-ethanol. However, if the MCC is functional, fully labeled [1,2-13C]-ethanol can be made. Using the complete cycle, the pentose phosphates can be regenerated and fully-labeled ethanol can be produced. The fragmentation pattern of ethanol leads to a [M-1]+ ion that is roughly three times more abundant compared to the molecular ion [M]+. This ratio of [M-1]+ to [M]+ ions was consistently observed for all four ethanol isotopes (FIG. 14A). The full pathway produced mostly double-labeled ethanol as determined by the ratio of 48 to 47 ions (FIG. 14B). In this cell-free system, no 48 ion could be detected in the "No Tal" control (FIG. 14C). Some unlabeled carbon was still present since the 46 ion, which is absent in the double-labeled ethanol standard, could be detected. The presence of the 48 ion demonstrates a catalytic MCC cycle.

Continuous Production of Ethanol.

Next, experiments were performed to show that the production of ethanol can be continuous if there is constant supply of formaldehyde. The optimal productivity was achieved when formaldehyde was added at a rate of 6 mM CH$_2$O/hour (FIG. 15A). Though feeding R5P should not be necessary since it can theoretically be replenished, improved production was achieved also fed at low levels (0.5 mM/hour). Since MCC should have conserved metabolites, this suggested that the pool of intermediates was degraded during the course of the reaction. To identify the distribution of metabolites and possible bottlenecks, high-performance ion chromatography (HPIC) with pulsed amperometric detection (PAD) was used to quantify the sugar phosphates (FIG. 15B). Within the first minute, the R5P quickly rearranges to other intermediates. Between the first and twentieth minutes, the overall pool decreases to a third of the initial point (through relative quantities remain about the same) indicating substrate degradation. G3P is known to be fairly unstable and was not detected in this system. The decrease in pool of intermediates explains why feeding low levels of R5P was required to maintaining continuous ethanol production from formaldehyde.

Production of Ethanol and n-Butanol from Methanol.

Finally, experiments were performed to demonstrate the conversion of methanol to ethanol and n-butanol. Since a NAD-dependent methanol dehydrogenase (EC 1.1.1.244) is only found from *B. methanolicus*, the initial target was to use this unique enzyme. However its low specific activity (<1 U/mg) and high Km (>100 mM) in the optimized buffer conditions, led to trace amounts of alcohols. Six methanol dehydrogenases were purified from *B. methanolicus* and constructed activator-insensitive mutants for each homolog. A single point mutation has been shown to make Mdh forty times more active in the absence of the Nudix activator. Additionally, bioprospecting was performed on a wide variety of predicted NAD dependent alcohol dehydrogenases from other organisms. Unfortunately, all purified enzymes demonstrated relatively poor activity towards methanol with higher specificity towards longer chain alcohols, consistent with previous results. The commercial alcohol dehydrogenase from *S. cerevisiae* was chosen, which is the same enzyme used for ethanol production. Although it does not have the highest activity towards methanol, its availability made it a more reasonable option than purifying large amounts other enzymes. The optimal production was identified by mapping a 2-dimensional parameter space (FIG. 20), varying F/Xpk and Adh (*S. cerevisiae*). This condition was used for a 24 hour time course (FIG. 15C). Several methanol concentrations were tested and 200 mM methanol was chosen since it produced the highest carbon yield. After five hours, the productivity decreases and this led to a final titer of 610 mg/L (13.3 mM) ethanol from 6200 mg/L (200 mM) methanol. The carbon yield was 80% (33.5 mM methanol consumed), exceeding the theoretical yield (66%) from the native pathway RuMP followed by EMP.

Figure 21:
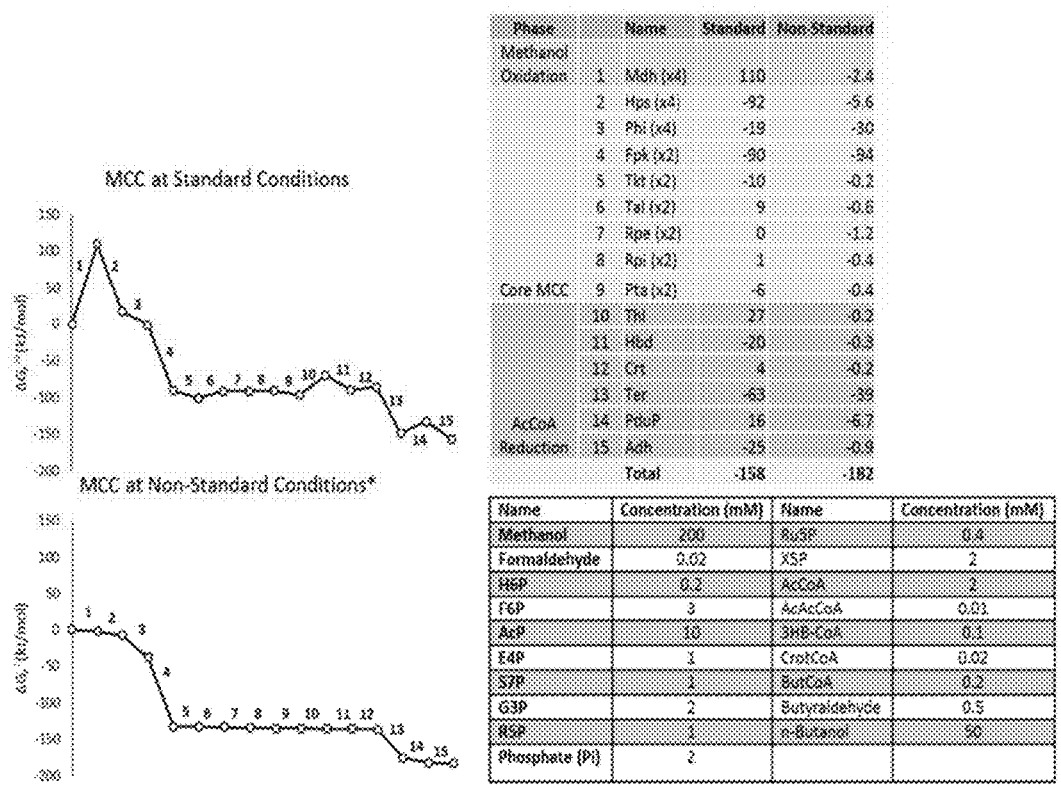
FIG. 21 shows thermodynamics of MCC in the conversion of methanol and n-butanol. Though the initial oxidation of methanol is thermodynamically difficult, Hps, F/Xpk, and Ter provide a significant driving force for irreversible formation of n-butanol. At non-standard conditions, it is possible to choose a set of concentrations so that every reaction has a negative ΔGr'. The reason for the discrepancy between the total ΔG (−158 for standard and −182 for non-standard) is due to a predicted error range from each reaction.

The pathway was then extended to n-butanol by including the enzymes from acetyl-CoA to n-butanol. These include thiolase (*Escherichia. coli*), 3-hydroxybutyryl-CoA dehydrogenase (*Clostridia acetobutylicium*), crotonase (*C. acetobutylicum*), trans-enoyl-CoA reductase (*Treponema denticola*), acylating aldehyde dehydrogenase (PduP from *Salmonella enterica*), and alcohol dehydrogenase (*S. cerevisiae*). Starting with 6200 mg/L (200 mM) of methanol, the final titer for n-butanol was 170 mg/L (2.3 mM). Since only 21.1 mM of methanol was consumed, this represents a 50% carbon yield (FIG. 15D). Remaining carbons were in ethanol (about 15%), acetate, and possibly some degradation products of sugar phosphates. Here the same alcohol dehydrogenase was used for methanol oxidation as well as ethanol and butanol production. Interestingly, even though this enzyme is reversible and has higher activity towards n-butanol and ethanol oxidation than methanol oxidation, the thermodynamic driving force (FIG. 21) effectively drives the reaction towards the longer chain alcohol.

TABLE B

Futile ATP Burning in RuMP-NOG versus the ATP-independent MCC

| Name | Reactant | Product | Direction | Enzyme |
|---|---|---|---|---|
| RUMP | 6 CH$_2$O + 6 Ru5P | 6 H6P | → | Hps |
| | 6 H6P | 6 F6P | ↔ | Phi |
| | F6P + ATP | FBP + ADP | → | Pfk |
| | FBP | G3P + DHAP | ↔ | Fba |
| | DHAP | G3P | ↔ | Tpi |
| | 2 G3P + 2 F6P | 2 X5P + 2 E4P | ↔ | Tkt |
| | 2 E4P + 2 F6P | 2 G3P + 2 S7P | ↔ | Tal |
| | 2 G3P + 2 S7P | 2 R5P + 2 X5P | ↔ | Tkt |
| | 4 X5P | 4 Ru5P | ↔ | Rpe |
| | 2 R5P | 2 Ru5P | ↔ | Rpi |
| NOGm3 | F6P | AcP + E4P | → | Fpk |
| | E4P + F6P | G3P + S7P | ↔ | Tal |
| | G3P + S7P | R5P + X5P | ↔ | Tkt |
| | R5P | Ru5P | ↔ | Rpi |
| | Ru5P | X5P | ↔ | Rpe |

TABLE B-continued

Futile ATP Burning in RuMP-NOG versus the ATP-independent MCC

| Name | Reactant | Product | Direction | Enzyme |
|---|---|---|---|---|
| | 2 X5P | 2 AcP + 2 G3P | → | Xpk |
| | G3P | DHAP | ↔ | Tpi |
| | G3P + DHAP | FBP | ↔ | Fba |
| | FBP | F6P | → | Fbp |
| MCC | 6 CH$_2$O + 6 Ru5P | 6 H6P | → | Hps |
| | 6 H6P | 6 F6P | ↔ | Phi |
| | 2 G3P + 2 F6P | 2 X5P + 2 E4P | ↔ | Tkt |
| | 2 E4P + 3 F6P | 2 G3P + 2 S7P | ↔ | Tal |
| | 3 G3P + 3 S7P | 3 R5P + 3 X5P | ↔ | Tkt |
| | 3 X5P | 3 Ru5P | ↔ | Rpe |
| | 3 R5P | 3 Ru5P | ↔ | Rpi |
| | F6P | AcP + E4P | → | Fpk |
| | 2 X5P | 2 AcP + 2 G3P | → | Xpk |

*In the RuMP-NOG combination, the reactions in orange can be eliminated. The reactions (Pfk and Fbp) in red constitute a futile ATP-burning cycle. By eliminating these unnecessary reactions, MCC reaches stoichiometric conversion of 6 CH$_2$O to 3 AcP (2 to 1 ratio) without ATP expenditure. NOGm3 denotes the third mode of NOG (1) that involves Fpk and two Xpk. A similar results could be obtained using either the first mode (Fpk only) or the second mode (Xpk only).

TABLE C

Kinetic Analysis of MCC

| | | Enzyme Specific Activity (μmol/min/mg protein) | | |
|---|---|---|---|---|
| Enzyme Reaction | Organism | WT Enzymes | Round 1 (1 Enzyme) | Round 2 (3 Enzymes) |
| Mdh | *B. methanolicus* | 0.25 | 7 | 15 |
| Hps | *M. capsulatus* | 69 | 69 | 69 |
| Phi | *M. flagellatus* | 147 | 147 | 147 |
| Fpk | *B. adolescentis* | 0.83 | 0.83 | 10 |
| Tal | *E. coli* | 60 | 60 | 60 |
| Tkt | *E. coli* | 100 | 100 | 100 |
| Rpe | *E. coli* | 257 | 257 | 257 |
| Rpi | *E. coli* | 937 | 937 | 937 |
| Pta | *B. subtilis* | 1150 | 1150 | 1150 |
| AtoB | *E. coli* | 1078 | 1078 | 1078 |
| Hbd | *C. acetobutylicum* | 147 | 147 | 147 |
| Crt | *C. acetobutylicum* | 6155 | 6155 | 6155 |
| Ter | *T. denticola* | 43 | 43 | 43 |
| PduP | *S. enterica* | 27 | 27 | 27 |
| Adh | *S. cerevisiae* | 18 | 18 | 18 |
| g BuOH/g protein/hr | | 0.044 | 2.61 | 4.94 |

*Calculations are based on specific activity and pathway stoichiometry. For example, Mdh must react four times to generate one n-butanol. Targeted enzyme improvement could drastically improve pathway productivity as shown.

Certain embodiments of the invention have been described. It will be understood that various modifications may be made without departing from the spirit and scope of the invention. Other embodiments are within the scope of the following claims.

What is claimed is:

1. A recombinant *E. coli* comprising a metabolic pathway for the synthesis of acetyl phosphate from formaldehyde using a pathway comprising:
    (i)(a) a hexulose-6-phosphate synthase having at least 95% sequence identity to SEQ ID NO:14 and catalyzes the formation of hexulose-6-phosphate from formaldehyde and ribulose-5-phosphate, or (b) dihydroxyacetone synthase having at least 95% sequence identity to SEQ ID NO:18 and catalyze the formation of dihydroxyacetone and glyceraldehyde-3-phosphate from xylulose-5-phosphate and formaldehyde; and
    (ii)(a) a hexulose-6-phosphate isomerase having at least 95% sequence identity to SEQ ID NO:16 and catalyzes the formation of fructose-6-phosphate from hexulose-6-phosphate, or (b) fructose-6-phosphate aldolase having at least 95% sequence identity to SEQ ID NO:20 and catalyzes the formation of fructose-6-phosphate from glyceraldehyde-3-phosphate and dihydroxyacetone; and
    (iii) a transaldolase having at least 95% sequence identity to SEQ ID NO:10 and catalyzes the formation of sedoheptulose-7-phosphate from fructose-6-phosphate and erythrose-4-phosphate;
    (iv) a transketolase having at least 95% sequence identity to SEQ ID NO:12 and catalyzes the formation of ribose-5-phosphate and xylulose-5-phosphate from sedoheptulose-7-phosphate and glyceraldehyde-3-phosphate and/or glyceraldehyde-3-phosphate and fructose-6-phosphate from xylulose-5-phosphate and erythrose-4-phosphate;
    (v) ribose-5-phosphate isomerase having at least 95% sequence identity to SEQ ID NO:8 and catalyzes the formation of ribulose-5-phosphate from ribose-5-phosphate; and
    (vi) a ribulose-5-phosphate epimerase having at least 95% sequence identity to SEQ ID NO:6 and catalyzes the formation of xylulose 5-phosphate from ribulose-5-phosphate; and
    (vii) an enzyme having phosphoketolase activity having at least 95% sequence identity to SEQ ID NO:2 and catalyzes the formation of acetyl-phosphate and glyceraldehyde 3-phosphate or erythrose-4-phosphate from xylulose 5-phosphate or fructose 6-phosphate,
    wherein the prokaryotic microorganism has an acetyl-phosphate yield better than a wild-type or parental prokaryotic organism, and wherein the conversion of formaldehyde to acetyl-phosphate using the pathway has minimal to no carbon loss.

2. The recombinant *E. coli* of claim 1, wherein the *E. coli* is engineered to express a phosphoketolase.

3. The recombinant *E. coli* of claim 2, wherein the phosphoketolase is Fpk, Xpk or a bifunctional F/Xpk enzyme.

4. The recombinant *E. coli* of claim 1, wherein the prokaryotic microorganism is engineered to heterologously expresses one or more of the following enzymes:
    (a) a phosphoketolase;
    (b) a transaldolase;
    (c) a transketolase;
    (d) a ribose-5-phosphate isomerase;

(e) a ribulose-5-phosphate epimerase;
(f) a hexulose-6-phosphate synthase;
(g) a hexulose-6-phosphate isomerase;
(h) a dihydroxyacetone synthase; and
(i) a fructose-6-phosphate aldolase.

5. The recombinant *E. coli* of claim 1, wherein the *E. coli* is engineered to express a phosphoketolase obtained from *Bifidobaceterium adolescentis*.

6. The recombinant *E. coli* of claim 5, wherein the phosphoketolase is a bifunctional F/Xpk.

7. The recombinant *E. coli* of claim 1, wherein the *E. coli* is engineered to express or over express a hexulose-6-phosphate synthase.

8. The recombinant *E. coli* of claim 7, wherein the hexulose-6-phosphate synthase is Hps.

9. The recombinant *E. coli* of claim 1, wherein the microorganism is engineered to express or over express a hexulose-6-phosphate isomerase.

10. The recombinant *E. coli* of claim 9, wherein the hexulose-6-phosphate isomerase is Phi.

11. The recombinant *E. coli* of claim 1, wherein the *E. coli* expresses, or is further recombinantly engineered to express or engineered to overexpress an alcohol oxidase.

12. The recombinant *E. coli* of claim 11, wherein the alcohol oxidase is Aox.

13. The recombinant *E. coli* of claim 11, wherein the alcohol oxidase has at least 95% sequence identity to SEQ ID NO:22 and has alcohol oxidase activity.

14. The recombinant *E. coli* of claim 1, wherein the microorganism is further engineered to have a reduction or knockout of expression of one or more of lactate dehydrogenase (ldhA), fumarate reductase iron-sulfur and anchor subunit (frdBC), aldehyde-alcohol dehydrogenase E (adhE), acetated kinase (ackA), pyruvate lyase (pflB), formaldehyde dehydrogenase (frmA), s-formylglutathione hydrolase (frmB/yeiG) and glyceraldehyde-3-phosphate dehydrogenase (gapA).

15. The recombinant *E. coli* of claim 1, wherein the microorganism is further engineered to produce isobutanol or n-butanol.

16. The recombinant *E. coli* of claim 1, wherein the microorganism further comprises a reduction or knockout of the expression of one or more enzymes selected from the group consisting of: a pyruvate decarboxylase and a glyceraldehyde-3-phosphate dehydrogenase.

17. The recombinant *E. coli* of claim 1, wherein the microorganism is further engineered to produce isobutanol or n-butanol.

18. The recombinant *E. coli* of claim 1,
wherein the hexulose-6-phosphate synthase is Hps from *Bacillus subtilis* or Hps from *Methylococcus Capsulatus*,
wherein the dihydroxyacetone synthase is Das from *Candida boindii*,
wherein the hexulose-6-phosphate isomerase is Phi from *Methylobacillus flagellatus* or Phi from *Methylococcus Capsulatus*,
wherein the fructose-6-phosphate aldolase Fsa is from *Salmonella enterica*,
wherein the transaldolase is Tal from *Escherichia* Coli,
wherein the transketolase is Tkt from *Escherichia Coli*,
wherein the ribose-5-phosphate isomerase is Rpi from *Escherichia* Coli,
wherein the ribulose-5-phosphate epimerase is Rpe from *Escherichia Coli*, and
wherein the enzyme having phosphoketolase activity is F/Xpk from *Bifidobacterium adolescentis*.

* * * * *

SEQUENCE LISTING

<160> NUMBER OF SEQ ID NOS: 39

<210> SEQ ID NO 1
<211> LENGTH: 2478
<212> TYPE: DNA
<213> ORGANISM: Bifidobacterium adolescentis
<220> FEATURE:
<221> NAME/KEY: CDS
<222> LOCATION: (1)..(2478)

<400> SEQUENCE: 1

-continued

| | |
|---|---|
| atg acg agt cct gtt att ggc acc cct tgg aag aag ctg aac gct ccg<br>Met Thr Ser Pro Val Ile Gly Thr Pro Trp Lys Lys Leu Asn Ala Pro<br>1               5                  10                  15 | 48 |
| gtt tcc gag gaa gct atc gaa ggc gtg gat aag tac tgg cgc gca gcc<br>Val Ser Glu Glu Ala Ile Glu Gly Val Asp Lys Tyr Trp Arg Ala Ala<br>        20                  25                  30 | 96 |
| aac tac ctc tcc atc ggc cag atc tat ctg cgt agc aac ccg ctg atg<br>Asn Tyr Leu Ser Ile Gly Gln Ile Tyr Leu Arg Ser Asn Pro Leu Met<br>            35                  40                  45 | 144 |
| aag gag cct ttc acc cgc gaa gac gtc aag cac cgt ctg gtc ggt cac<br>Lys Glu Pro Phe Thr Arg Glu Asp Val Lys His Arg Leu Val Gly His<br>50                  55                  60 | 192 |
| tgg ggc acc acc ccg ggc ctg aac ttc ctc atc ggc cac atc aac cgt<br>Trp Gly Thr Thr Pro Gly Leu Asn Phe Leu Ile Gly His Ile Asn Arg<br>65                  70                  75                  80 | 240 |
| ctc att gct gat cac cag cag aac act gtg atc atc atg ggc ccg ggc<br>Leu Ile Ala Asp His Gln Gln Asn Thr Val Ile Ile Met Gly Pro Gly<br>                85                  90                  95 | 288 |
| cac ggc ggc ccg gct ggt acc gct cag tcc tac ctg gac ggc acc tac<br>His Gly Gly Pro Ala Gly Thr Ala Gln Ser Tyr Leu Asp Gly Thr Tyr<br>            100                 105                 110 | 336 |
| acc gag tac ttc ccg aac atc acc aag gat gag gct ggc ctg cag aag<br>Thr Glu Tyr Phe Pro Asn Ile Thr Lys Asp Glu Ala Gly Leu Gln Lys<br>        115                 120                 125 | 384 |
| ttc ttc cgc cag ttc tcc tac ccg ggt ggc atc ccg tcc cac tac gct<br>Phe Phe Arg Gln Phe Ser Tyr Pro Gly Gly Ile Pro Ser His Tyr Ala<br>    130                 135                 140 | 432 |
| ccg gag acc ccg ggc tcc atc cac gaa ggc ggc gag ctg ggt tac gcc<br>Pro Glu Thr Pro Gly Ser Ile His Glu Gly Gly Glu Leu Gly Tyr Ala<br>145                 150                 155                 160 | 480 |
| ctg tcc cac gcc tac ggc gct gtg atg aac aac ccg agc ctg ttc gtc<br>Leu Ser His Ala Tyr Gly Ala Val Met Asn Asn Pro Ser Leu Phe Val<br>                165                 170                 175 | 528 |
| ccg gcc atc gtc ggc gac ggt gaa gct gag acc ggc ccg ctg gcc acc<br>Pro Ala Ile Val Gly Asp Gly Glu Ala Glu Thr Gly Pro Leu Ala Thr<br>            180                 185                 190 | 576 |
| ggc tgg cag tcc aac aag ctc atc aac ccg cgc acc gac ggt atc gtg<br>Gly Trp Gln Ser Asn Lys Leu Ile Asn Pro Arg Thr Asp Gly Ile Val<br>        195                 200                 205 | 624 |
| ctg ccg atc ctg cac ctc aac ggc tac aag atc gcc aac ccg acc atc<br>Leu Pro Ile Leu His Leu Asn Gly Tyr Lys Ile Ala Asn Pro Thr Ile<br>    210                 215                 220 | 672 |
| ctg tcc cgc atc tcc gac gaa gag ctc cac gag ttc ttc cac ggc atg<br>Leu Ser Arg Ile Ser Asp Glu Glu Leu His Glu Phe Phe His Gly Met<br>225                 230                 235                 240 | 720 |
| ggc tat gag ccg tac gag ttc gtc gct ggc ttc gac aac gag gat cac<br>Gly Tyr Glu Pro Tyr Glu Phe Val Ala Gly Phe Asp Asn Glu Asp His<br>                245                 250                 255 | 768 |
| ctg tcg atc cac cgt cgt ttc gcc gag ctg ttc gag acc gtc ttc gac<br>Leu Ser Ile His Arg Arg Phe Ala Glu Leu Phe Glu Thr Val Phe Asp<br>            260                 265                 270 | 816 |
| gag atc tgc gac atc aag gcc gcc gct cag acc gac gac atg act cgt<br>Glu Ile Cys Asp Ile Lys Ala Ala Ala Gln Thr Asp Asp Met Thr Arg<br>        275                 280                 285 | 864 |
| ccg ttc tac ccg atg atc atc ttc cgt acc ccg aag ggc tgg acc tgc<br>Pro Phe Tyr Pro Met Ile Ile Phe Arg Thr Pro Lys Gly Trp Thr Cys<br>    290                 295                 300 | 912 |
| ccg aag ttc atc gac ggc aag aag acc gag ggc tcc tgg cgt tcc cac<br>Pro Lys Phe Ile Asp Gly Lys Lys Thr Glu Gly Ser Trp Arg Ser His<br>305                 310                 315                 320 | 960 |

```
cag gtg ccg ctg gct tcc gcc cgc gat acc gag gcc cac ttc gag gtc    1008
Gln Val Pro Leu Ala Ser Ala Arg Asp Thr Glu Ala His Phe Glu Val
            325                 330                 335 ctc aag aac tgg ctc gag tcc tac aag ccg gaa gag ctg ttc gac gag    1056
Leu Lys Asn Trp Leu Glu Ser Tyr Lys Pro Glu Glu Leu Phe Asp Glu
        340                 345                 350 aac ggc gcc gtg aag ccg gaa gtc acc gcc ttc atg ccg acc ggc gaa    1104
Asn Gly Ala Val Lys Pro Glu Val Thr Ala Phe Met Pro Thr Gly Glu
    355                 360                 365 ctg cgc atc ggt gag aac ccg aac gcc aac ggt ggc cgc atc cgc gaa    1152
Leu Arg Ile Gly Glu Asn Pro Asn Ala Asn Gly Gly Arg Ile Arg Glu
370                 375                 380 gag ctg aag ctg ccg aag ctg gaa gac tac gag gtc aag gaa gtc gcc    1200
Glu Leu Lys Leu Pro Lys Leu Glu Asp Tyr Glu Val Lys Glu Val Ala
385                 390                 395                 400 gag tac ggc cac ggc tgg ggc cag ctc gag gcc acc cgt cgt ctg ggc    1248
Glu Tyr Gly His Gly Trp Gly Gln Leu Glu Ala Thr Arg Arg Leu Gly
                405                 410                 415 gtc tac acc cgc gac atc atc aag aac aac ccg gac tcc ttc cgt atc    1296
Val Tyr Thr Arg Asp Ile Ile Lys Asn Asn Pro Asp Ser Phe Arg Ile
            420                 425                 430 ttc gga ccg gat gag acc gct tcc aac cgt ctg cag gcc gct tac gac    1344
Phe Gly Pro Asp Glu Thr Ala Ser Asn Arg Leu Gln Ala Ala Tyr Asp
        435                 440                 445 gtc acc aac aag cag tgg gac gcc ggc tac ctg tcc gct cag gtc gac    1392
Val Thr Asn Lys Gln Trp Asp Ala Gly Tyr Leu Ser Ala Gln Val Asp
    450                 455                 460 gag cac atg gct gtc acc ggc cag gtc acc gag cag ctt tcc gag cac    1440
Glu His Met Ala Val Thr Gly Gln Val Thr Glu Gln Leu Ser Glu His
465                 470                 475                 480 cag atg gaa ggc ttc ctc gag ggc tac ctg ctg acc ggc cgt cac ggc    1488
Gln Met Glu Gly Phe Leu Glu Gly Tyr Leu Leu Thr Gly Arg His Gly
                485                 490                 495 atc tgg agc tcc tat gag tcc ttc gtg cac gtg atc gac tcc atg ctg    1536
Ile Trp Ser Ser Tyr Glu Ser Phe Val His Val Ile Asp Ser Met Leu
            500                 505                 510 aac cag cac gcc aag tgg ctc gag gct acc gtc cgc gag att ccg tgg    1584
Asn Gln His Ala Lys Trp Leu Glu Ala Thr Val Arg Glu Ile Pro Trp
        515                 520                 525 cgc aag ccg atc tcc tcc atg aac ctg ctc gtc tcc tcc cac gtg tgg    1632
Arg Lys Pro Ile Ser Ser Met Asn Leu Leu Val Ser Ser His Val Trp
    530                 535                 540 cgt cag gat cac aac ggc ttc tcc cac cag gat ccg ggt gtc acc tcc    1680
Arg Gln Asp His Asn Gly Phe Ser His Gln Asp Pro Gly Val Thr Ser
545                 550                 555                 560 gtc ctg ctg aac aag tgc ttc aac aac gat cac gtg atc ggc atc tac    1728
Val Leu Leu Asn Lys Cys Phe Asn Asn Asp His Val Ile Gly Ile Tyr
                565                 570                 575 ttc ccg gtg gat tcc aac atg ctg ctc gct gtg gct gag aag tgc tac    1776
Phe Pro Val Asp Ser Asn Met Leu Leu Ala Val Ala Glu Lys Cys Tyr
            580                 585                 590 aag tcc acc aac aag atc aac gcc atc atc gcc ggc aag cag ccg gcc    1824
Lys Ser Thr Asn Lys Ile Asn Ala Ile Ile Ala Gly Lys Gln Pro Ala
        595                 600                 605 gcc acc tgg ctg acc ctg gac gaa gct cgc gcc gag ctc gag aag ggt    1872
Ala Thr Trp Leu Thr Leu Asp Glu Ala Arg Ala Glu Leu Glu Lys Gly
    610                 615                 620 gct gcc gag tgg aag tgg gct tcc aac gtg aag tcc aac gat gag gct    1920
Ala Ala Glu Trp Lys Trp Ala Ser Asn Val Lys Ser Asn Asp Glu Ala
```

```
                625                 630                 635                 640
cag atc gtg ctc gcc gcc acc ggt gat gtt ccg act cag gaa atc atg          1968
Gln Ile Val Leu Ala Ala Thr Gly Asp Val Pro Thr Gln Glu Ile Met
                            645                 650                 655 gcc gct gcc gac aag ctg gac gcc atg ggc atc aag ttc aag gtc gtc          2016
Ala Ala Ala Asp Lys Leu Asp Ala Met Gly Ile Lys Phe Lys Val Val
                660                 665                 670 aac gtg gtt gac ctg gtc aag ctg cag tcc gcc aag gag aac aac gag          2064
Asn Val Val Asp Leu Val Lys Leu Gln Ser Ala Lys Glu Asn Asn Glu
            675                 680                 685 gcc ctc tcc gat gag gag ttc gct gag ctg ttc acc gag gac aag ccg          2112
Ala Leu Ser Asp Glu Glu Phe Ala Glu Leu Phe Thr Glu Asp Lys Pro
        690                 695                 700 gtc ctg ttc gct tac cac tcc tat gcc cgc gat gtg cgt ggt ctg atc          2160
Val Leu Phe Ala Tyr His Ser Tyr Ala Arg Asp Val Arg Gly Leu Ile
705                 710                 715                 720 tac gat cgc ccg aac cac gac aac ttc aac gtt cac ggc tac gag gag          2208
Tyr Asp Arg Pro Asn His Asp Asn Phe Asn Val His Gly Tyr Glu Glu
                    725                 730                 735 cag ggc tcc acc acc acc ccg tac gac atg gtt cgc gtg aac aac atc          2256
Gln Gly Ser Thr Thr Thr Pro Tyr Asp Met Val Arg Val Asn Asn Ile
                740                 745                 750 gat cgc tac gag ctc cag gct gaa gct ctg cgc atg att gac gct gac          2304
Asp Arg Tyr Glu Leu Gln Ala Glu Ala Leu Arg Met Ile Asp Ala Asp
            755                 760                 765 aag tac gcc gac aag atc aac gag ctc gag gcc ttc cgt cag gaa gcc          2352
Lys Tyr Ala Asp Lys Ile Asn Glu Leu Glu Ala Phe Arg Gln Glu Ala
        770                 775                 780 ttc cag ttc gct gtc gac aac ggc tac gat cac ccg gat tac acc gac          2400
Phe Gln Phe Ala Val Asp Asn Gly Tyr Asp His Pro Asp Tyr Thr Asp
785                 790                 795                 800 tgg gtc tac tcc ggt gtc aac acc aac aag cag ggt gct atc tcc gct          2448
Trp Val Tyr Ser Gly Val Asn Thr Asn Lys Gln Gly Ala Ile Ser Ala
                    805                 810                 815 acc gcc gca acc gct ggc gat aac gag tga                                  2478
Thr Ala Ala Thr Ala Gly Asp Asn Glu
                820                 825

<210> SEQ ID NO 2
<211> LENGTH: 825
<212> TYPE: PRT
<213> ORGANISM: Bifidobacterium adolescentis

<400> SEQUENCE: 2

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
                20                  25                  30

Asn Tyr Leu Ser Ile Gly Gln Ile Tyr Leu Arg Ser Asn Pro Leu Met
            35                  40                  45

Lys Glu Pro Phe Thr Arg Glu Asp Val Lys His Arg Leu Val Gly His
        50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
                100                 105                 110
```

```
Thr Glu Tyr Phe Pro Asn Ile Thr Lys Asp Glu Ala Gly Leu Gln Lys
            115                 120                 125

Phe Phe Arg Gln Phe Ser Tyr Pro Gly Gly Ile Pro Ser His Tyr Ala
        130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
                180                 185                 190

Gly Trp Gln Ser Asn Lys Leu Ile Asn Pro Arg Thr Asp Gly Ile Val
            195                 200                 205

Leu Pro Ile Leu His Leu Asn Gly Tyr Lys Ile Ala Asn Pro Thr Ile
        210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
                260                 265                 270

Glu Ile Cys Asp Ile Lys Ala Ala Ala Gln Thr Asp Asp Met Thr Arg
            275                 280                 285

Pro Phe Tyr Pro Met Ile Ile Phe Arg Thr Pro Lys Gly Trp Thr Cys
        290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Glu
                340                 345                 350

Asn Gly Ala Val Lys Pro Glu Val Thr Ala Phe Met Pro Thr Gly Glu
            355                 360                 365

Leu Arg Ile Gly Glu Asn Pro Asn Ala Asn Gly Gly Arg Ile Arg Glu
        370                 375                 380

Glu Leu Lys Leu Pro Lys Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
                420                 425                 430

Phe Gly Pro Asp Glu Thr Ala Ser Asn Arg Leu Gln Ala Ala Tyr Asp
            435                 440                 445

Val Thr Asn Lys Gln Trp Asp Ala Gly Tyr Leu Ser Ala Gln Val Asp
        450                 455                 460

Glu His Met Ala Val Thr Gly Gln Val Thr Glu Gln Leu Ser Glu His
465                 470                 475                 480

Gln Met Glu Gly Phe Leu Glu Gly Tyr Leu Leu Thr Gly Arg His Gly
                485                 490                 495

Ile Trp Ser Ser Tyr Glu Ser Phe Val His Val Ile Asp Ser Met Leu
                500                 505                 510

Asn Gln His Ala Lys Trp Leu Glu Ala Thr Val Arg Glu Ile Pro Trp
            515                 520                 525

Arg Lys Pro Ile Ser Ser Met Asn Leu Leu Val Ser Ser His Val Trp
```

```
                530             535             540
Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
            580                 585                 590

Lys Ser Thr Asn Lys Ile Asn Ala Ile Ile Ala Gly Lys Gln Pro Ala
                595                 600                 605

Ala Thr Trp Leu Thr Leu Asp Glu Ala Arg Ala Glu Leu Glu Lys Gly
            610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Ala Lys Glu Asn Asn Glu
                675                 680                 685

Ala Leu Ser Asp Glu Glu Phe Ala Glu Leu Phe Thr Glu Asp Lys Pro
            690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Pro Tyr Asp Met Val Arg Val Asn Asn Ile
            740                 745                 750

Asp Arg Tyr Glu Leu Gln Ala Glu Ala Leu Arg Met Ile Asp Ala Asp
                755                 760                 765

Lys Tyr Ala Asp Lys Ile Asn Glu Leu Glu Ala Phe Arg Gln Glu Ala
            770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
                805                 810                 815

Thr Ala Thr Ala Gly Asp Asn Glu
            820                 825

<210> SEQ ID NO 3
<211> LENGTH: 1152
<212> TYPE: DNA
<213> ORGANISM: Bacillus methanolicus
<220> FEATURE:
<221> NAME/KEY: CDS
<222> LOCATION: (1)..(1152)

<400> SEQUENCE: 3 atg acg caa aga aac ttt ttc att cca cca gct agc gta att gga cgc      48
Met Thr Gln Arg Asn Phe Phe Ile Pro Pro Ala Ser Val Ile Gly Arg
1               5                   10                  15 ggc gct gta aaa gaa gta gga aca aga ctt aag caa att gga gct aca      96
Gly Ala Val Lys Glu Val Gly Thr Arg Leu Lys Gln Ile Gly Ala Thr
            20                  25                  30 aaa gca ctt atc gtt aca gat gca ttt ctt cat ggc aca ggt ttg tca     144
Lys Ala Leu Ile Val Thr Asp Ala Phe Leu His Gly Thr Gly Leu Ser
        35                  40                  45
```

-continued

| | |
|---|---|
| gaa gaa gtt gct aaa aac att cgt gaa gct ggc ctt gat gct gta att<br>Glu Glu Val Ala Lys Asn Ile Arg Glu Ala Gly Leu Asp Ala Val Ile<br>50              55                  60 | 192 |
| ttc cca aaa gct caa cca gat cca gca gat aca caa gtt cat gaa ggc<br>Phe Pro Lys Ala Gln Pro Asp Pro Ala Asp Thr Gln Val His Glu Gly<br>65                  70                  75                  80 | 240 |
| gta gat ata ttc aaa caa gaa aaa tgt gat gca ctt gtt tct atc ggt<br>Val Asp Ile Phe Lys Gln Glu Lys Cys Asp Ala Leu Val Ser Ile Gly<br>85                  90                  95 | 288 |
| gga ggt agc tct cac gat aca gca aaa gca atc ggt tta gtt gca gca<br>Gly Gly Ser Ser His Asp Thr Ala Lys Ala Ile Gly Leu Val Ala Ala<br>100                 105                 110 | 336 |
| aac ggc gga aga atc aac gac tat caa ggt gta aac agt gta gaa aaa<br>Asn Gly Gly Arg Ile Asn Asp Tyr Gln Gly Val Asn Ser Val Glu Lys<br>115                 120                 125 | 384 |
| ccg gtt gtt cca gta gtt gca atc act aca aca gct ggt act ggt agt<br>Pro Val Val Pro Val Val Ala Ile Thr Thr Thr Ala Gly Thr Gly Ser<br>130                 135                 140 | 432 |
| gaa aca aca tct ctt gcg gtt att aca gat tct gca cgt aaa gta aaa<br>Glu Thr Thr Ser Leu Ala Val Ile Thr Asp Ser Ala Arg Lys Val Lys<br>145                 150                 155                 160 | 480 |
| atg cca gtt atc gat gag aaa att aca cca act gta gca att gtt gac<br>Met Pro Val Ile Asp Glu Lys Ile Thr Pro Thr Val Ala Ile Val Asp<br>165                 170                 175 | 528 |
| cca gaa tta atg gtg aaa aaa cca gct gga tta aca att gca act ggt<br>Pro Glu Leu Met Val Lys Lys Pro Ala Gly Leu Thr Ile Ala Thr Gly<br>180                 185                 190 | 576 |
| atg gat gca tta tcc cat gca att gaa gca tat gtt gca aaa cgt gct<br>Met Asp Ala Leu Ser His Ala Ile Glu Ala Tyr Val Ala Lys Arg Ala<br>195                 200                 205 | 624 |
| aca cca gtt act gat gcg ttt gca att caa gca atg aaa ctc att aat<br>Thr Pro Val Thr Asp Ala Phe Ala Ile Gln Ala Met Lys Leu Ile Asn<br>210                 215                 220 | 672 |
| gaa tac tta cca cgt gcg gtt gca aat gga gaa gac atc gaa gca cgt<br>Glu Tyr Leu Pro Arg Ala Val Ala Asn Gly Glu Asp Ile Glu Ala Arg<br>225                 230                 235                 240 | 720 |
| gaa gca atg gct tat gca caa tac atg gca gga gtg gca ttt aac aac<br>Glu Ala Met Ala Tyr Ala Gln Tyr Met Ala Gly Val Ala Phe Asn Asn<br>245                 250                 255 | 768 |
| gga ggt tta gga tta gta cac tct att tct cac caa gta ggt gga gtt<br>Gly Gly Leu Gly Leu Val His Ser Ile Ser His Gln Val Gly Gly Val<br>260                 265                 270 | 816 |
| tac aag tta caa cac gga atc tgt aac tca gtt aat atg cca cac gtt<br>Tyr Lys Leu Gln His Gly Ile Cys Asn Ser Val Asn Met Pro His Val<br>275                 280                 285 | 864 |
| tgc caa ttc aac tta att gct cgt act gaa cgc ttc gca cac att gct<br>Cys Gln Phe Asn Leu Ile Ala Arg Thr Glu Arg Phe Ala His Ile Ala<br>290                 295                 300 | 912 |
| gag ctt tta ggc gag aat gtt tct ggc tta agc act gca tct gct gct<br>Glu Leu Leu Gly Glu Asn Val Ser Gly Leu Ser Thr Ala Ser Ala Ala<br>305                 310                 315                 320 | 960 |
| gag aga gca att gta gcg ctt caa cgc tat aac aaa aac ttc ggt atc<br>Glu Arg Ala Ile Val Ala Leu Gln Arg Tyr Asn Lys Asn Phe Gly Ile<br>325                 330                 335 | 1008 |
| cca tct ggc tat gca gaa atg ggc gta aaa gaa gag gat atc gaa tta<br>Pro Ser Gly Tyr Ala Glu Met Gly Val Lys Glu Glu Asp Ile Glu Leu<br>340                 345                 350 | 1056 |
| tta gcg aac aac gcg tac caa gac gta tgt act cta gat aac cca cgt<br>Leu Ala Asn Asn Ala Tyr Gln Asp Val Cys Thr Leu Asp Asn Pro Arg<br>355                 360                 365 | 1104 |

```
gtt cct act gtt caa gac att gca caa atc atc aaa aac gct ctg taa    1152
Val Pro Thr Val Gln Asp Ile Ala Gln Ile Ile Lys Asn Ala Leu
    370             375             380
```

<210> SEQ ID NO 4
<211> LENGTH: 383
<212> TYPE: PRT
<213> ORGANISM: Bacillus methanolicus

<400> SEQUENCE: 4

```
Met Thr Gln Arg Asn Phe Phe Ile Pro Pro Ala Ser Val Ile Gly Arg
1               5                   10                  15

Gly Ala Val Lys Glu Val Gly Thr Arg Leu Lys Gln Ile Gly Ala Thr
            20                  25                  30

Lys Ala Leu Ile Val Thr Asp Ala Phe Leu His Gly Thr Gly Leu Ser
        35                  40                  45

Glu Glu Val Ala Lys Asn Ile Arg Glu Ala Gly Leu Asp Ala Val Ile
    50                  55                  60

Phe Pro Lys Ala Gln Pro Asp Pro Ala Asp Thr Gln Val His Glu Gly
65                  70                  75                  80

Val Asp Ile Phe Lys Gln Glu Lys Cys Asp Ala Leu Val Ser Ile Gly
                85                  90                  95

Gly Gly Ser Ser His Asp Thr Ala Lys Ala Ile Gly Leu Val Ala Ala
            100                 105                 110

Asn Gly Gly Arg Ile Asn Asp Tyr Gln Gly Val Asn Ser Val Glu Lys
        115                 120                 125

Pro Val Val Pro Val Val Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                165                 170                 175

Pro Glu Leu Met Val Lys Lys Pro Ala Gly Leu Thr Ile Ala Thr Gly
            180                 185                 190

Met Asp Ala Leu Ser His Ala Ile Glu Ala Tyr Val Ala Lys Arg Ala
        195                 200                 205

Thr Pro Val Thr Asp Ala Phe Ala Ile Gln Ala Met Lys Leu Ile Asn
    210                 215                 220

Glu Tyr Leu Pro Arg Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
                245                 250                 255

Gly Gly Leu Gly Leu Val His Ser Ile Ser His Gln Val Gly Gly Val
            260                 265                 270

Tyr Lys Leu Gln His Gly Ile Cys Asn Ser Val Asn Met Pro His Val
        275                 280                 285

Cys Gln Phe Asn Leu Ile Ala Arg Thr Glu Arg Phe Ala His Ile Ala
    290                 295                 300

Glu Leu Leu Gly Glu Asn Val Ser Gly Leu Ser Thr Ala Ser Ala Ala
305                 310                 315                 320

Glu Arg Ala Ile Val Ala Leu Gln Arg Tyr Asn Lys Asn Phe Gly Ile
                325                 330                 335

Pro Ser Gly Tyr Ala Glu Met Gly Val Lys Glu Glu Asp Ile Glu Leu
            340                 345                 350
```

```
Leu Ala Asn Asn Ala Tyr Gln Asp Val Cys Thr Leu Asp Asn Pro Arg
        355                 360                 365

Val Pro Thr Val Gln Asp Ile Ala Gln Ile Ile Lys Asn Ala Leu
    370                 375                 380

<210> SEQ ID NO 5
<211> LENGTH: 678
<212> TYPE: DNA
<213> ORGANISM: Escherichia coli
<220> FEATURE:
<221> NAME/KEY: CDS
<222> LOCATION: (1)..(678)

<400> SEQUENCE: 5 atg aaa cag tat ttg att gcc ccc tca att ctg tcg gct gat ttt gcc      48
Met Lys Gln Tyr Leu Ile Ala Pro Ser Ile Leu Ser Ala Asp Phe Ala
1               5                   10                  15 cgc ctg ggt gaa gat acc gca aaa gcc ctg gca gct ggc gct gat gtc      96
Arg Leu Gly Glu Asp Thr Ala Lys Ala Leu Ala Ala Gly Ala Asp Val
                20                  25                  30 gtg cat ttt gac gtc atg gat aac cac tat gtt ccc aat ctg acg att     144
Val His Phe Asp Val Met Asp Asn His Tyr Val Pro Asn Leu Thr Ile
            35                  40                  45 ggg cca atg gtg ctg aaa tcc ttg cgt aac tat ggc att acc gcc cct     192
Gly Pro Met Val Leu Lys Ser Leu Arg Asn Tyr Gly Ile Thr Ala Pro
        50                  55                  60 atc gac gta cac ctg atg gtg aaa ccc gtc gat cgc att gtg cct gat     240
Ile Asp Val His Leu Met Val Lys Pro Val Asp Arg Ile Val Pro Asp
65                  70                  75                  80 ttc gct gcc gct ggt gcc agc atc att acc ttt cat cca gaa gcc tcc     288
Phe Ala Ala Ala Gly Ala Ser Ile Ile Thr Phe His Pro Glu Ala Ser
                85                  90                  95 gag cat gtt gac cgc acg ctg caa ctg att aaa gaa aat ggc tgt aaa     336
Glu His Val Asp Arg Thr Leu Gln Leu Ile Lys Glu Asn Gly Cys Lys
                100                 105                 110 gcg ggt ctg gta ttt aac ccg gcg aca cct ctg agc tat ctg gat tac     384
Ala Gly Leu Val Phe Asn Pro Ala Thr Pro Leu Ser Tyr Leu Asp Tyr
            115                 120                 125 gtg atg gat aag ctg gat gtg atc ctg ctg atg tcc gtc aac cct ggt     432
Val Met Asp Lys Leu Asp Val Ile Leu Leu Met Ser Val Asn Pro Gly
        130                 135                 140 ttc ggc ggt cag tct ttc att cct caa aca ctg gat aaa ctg cgc gaa     480
Phe Gly Gly Gln Ser Phe Ile Pro Gln Thr Leu Asp Lys Leu Arg Glu
145                 150                 155                 160 gta cgt cgc cgt atc gac gag tct ggc ttt gac att cga cta gaa gtg     528
Val Arg Arg Arg Ile Asp Glu Ser Gly Phe Asp Ile Arg Leu Glu Val
                165                 170                 175 gac ggt ggc gtg aag gtg aac aac att ggc gaa atc gct gcg gcg ggc     576
Asp Gly Gly Val Lys Val Asn Asn Ile Gly Glu Ile Ala Ala Ala Gly
                180                 185                 190 gcg gat atg ttc gtc gcc ggt tcg gca atc ttc gac cag cca gac tac     624
Ala Asp Met Phe Val Ala Gly Ser Ala Ile Phe Asp Gln Pro Asp Tyr
            195                 200                 205 aaa aaa gtc att gat gaa atg cgc agt gaa ctg gca aag gta agt cat     672
Lys Lys Val Ile Asp Glu Met Arg Ser Glu Leu Ala Lys Val Ser His
        210                 215                 220 gaa taa                                                             678
Glu
225

<210> SEQ ID NO 6
```

```
<211> LENGTH: 225
<212> TYPE: PRT
<213> ORGANISM: Escherichia coli

<400> SEQUENCE: 6

Met Lys Gln Tyr Leu Ile Ala Pro Ser Ile Leu Ser Ala Asp Phe Ala
1               5                   10                  15

Arg Leu Gly Glu Asp Thr Ala Lys Ala Leu Ala Ala Gly Ala Asp Val
            20                  25                  30

Val His Phe Asp Val Met Asp Asn His Tyr Val Pro Asn Leu Thr Ile
        35                  40                  45

Gly Pro Met Val Leu Lys Ser Leu Arg Asn Tyr Gly Ile Thr Ala Pro
    50                  55                  60

Ile Asp Val His Leu Met Val Lys Pro Val Asp Arg Ile Val Pro Asp
65                  70                  75                  80

Phe Ala Ala Ala Gly Ala Ser Ile Ile Thr Phe His Pro Glu Ala Ser
                85                  90                  95

Glu His Val Asp Arg Thr Leu Gln Leu Ile Lys Glu Asn Gly Cys Lys
            100                 105                 110

Ala Gly Leu Val Phe Asn Pro Ala Thr Pro Leu Ser Tyr Leu Asp Tyr
        115                 120                 125

Val Met Asp Lys Leu Asp Val Ile Leu Leu Met Ser Val Asn Pro Gly
    130                 135                 140

Phe Gly Gly Gln Ser Phe Ile Pro Gln Thr Leu Asp Lys Leu Arg Glu
145                 150                 155                 160

Val Arg Arg Arg Ile Asp Glu Ser Gly Phe Asp Ile Arg Leu Glu Val
                165                 170                 175

Asp Gly Gly Val Lys Val Asn Asn Ile Gly Glu Ile Ala Ala Ala Gly
            180                 185                 190

Ala Asp Met Phe Val Ala Gly Ser Ala Ile Phe Asp Gln Pro Asp Tyr
        195                 200                 205

Lys Lys Val Ile Asp Glu Met Arg Ser Glu Leu Ala Lys Val Ser His
    210                 215                 220

Glu
225

<210> SEQ ID NO 7
<211> LENGTH: 660
<212> TYPE: DNA
<213> ORGANISM: Escherichia coli
<220> FEATURE:
<221> NAME/KEY: CDS
<222> LOCATION: (1)..(660)

<400> SEQUENCE: 7 atg acg cag gat gaa ttg aaa aaa gca gta gga tgg gcg gca ctt cag       48
Met Thr Gln Asp Glu Leu Lys Lys Ala Val Gly Trp Ala Ala Leu Gln
1               5                   10                  15 tat gtt cag ccc ggc acc att gtt ggt gta ggt aca ggt tcc acc gcc       96
Tyr Val Gln Pro Gly Thr Ile Val Gly Val Gly Thr Gly Ser Thr Ala
            20                  25                  30 gca cac ttt att gac gcg ctc ggt aca atg aaa ggc cag att gaa ggg      144
Ala His Phe Ile Asp Ala Leu Gly Thr Met Lys Gly Gln Ile Glu Gly
        35                  40                  45 gcc gtt tcc agt tca gat gct tcc act gaa aaa ctg aaa agc ctc ggc      192
Ala Val Ser Ser Ser Asp Ala Ser Thr Glu Lys Leu Lys Ser Leu Gly
    50                  55                  60 att cac gtt ttt gat ctc aac gaa gtc gac agc ctt ggc atc tac gtt      240
```

```
Ile His Val Phe Asp Leu Asn Glu Val Asp Ser Leu Gly Ile Tyr Val
 65                  70                  75                  80 gat ggc gca gat gaa atc aac ggc cac atg caa atg atc aaa ggc ggc      288
Asp Gly Ala Asp Glu Ile Asn Gly His Met Gln Met Ile Lys Gly Gly
                     85                  90                  95 ggc gcg gcg ctg acc cgt gaa aaa atc att gct tcg gtt gca gaa aaa      336
Gly Ala Ala Leu Thr Arg Glu Lys Ile Ile Ala Ser Val Ala Glu Lys
            100                 105                 110 ttt atc tgt att gca gac gct tcc aag cag gtt gat att ctg ggt aaa      384
Phe Ile Cys Ile Ala Asp Ala Ser Lys Gln Val Asp Ile Leu Gly Lys
        115                 120                 125 ttc ccg ctg cca gta gaa gtt atc ccg atg gca cgt agt gca gtg gcg      432
Phe Pro Leu Pro Val Glu Val Ile Pro Met Ala Arg Ser Ala Val Ala
    130                 135                 140 cgt cag ctg gtg aaa ctg ggc ggt cgt ccg gaa tac cgt cag ggc gtg      480
Arg Gln Leu Val Lys Leu Gly Gly Arg Pro Glu Tyr Arg Gln Gly Val
145                 150                 155                 160 gtg acc gat aat ggc aac gtg atc ctc gac gtc cac ggc atg gaa atc      528
Val Thr Asp Asn Gly Asn Val Ile Leu Asp Val His Gly Met Glu Ile
                165                 170                 175 ctt gac ccg ata gcg atg gaa aac gcc ata aat gcg att cct ggc gtg      576
Leu Asp Pro Ile Ala Met Glu Asn Ala Ile Asn Ala Ile Pro Gly Val
            180                 185                 190 gtg act gtt ggc ttg ttt gct aac cgt ggc gcg gac gtt gcg ctg att      624
Val Thr Val Gly Leu Phe Ala Asn Arg Gly Ala Asp Val Ala Leu Ile
        195                 200                 205 ggc aca cct gac ggt gtc aaa acc att gtg aaa tga                      660
Gly Thr Pro Asp Gly Val Lys Thr Ile Val Lys
    210                 215

<210> SEQ ID NO 8
<211> LENGTH: 219
<212> TYPE: PRT
<213> ORGANISM: Escherichia coli

<400> SEQUENCE: 8

Met Thr Gln Asp Glu Leu Lys Lys Ala Val Gly Trp Ala Ala Leu Gln
1               5                   10                  15

Tyr Val Gln Pro Gly Thr Ile Val Gly Val Gly Thr Gly Ser Thr Ala
                20                  25                  30

Ala His Phe Ile Asp Ala Leu Gly Thr Met Lys Gly Gln Ile Glu Gly
            35                  40                  45

Ala Val Ser Ser Ser Asp Ala Ser Thr Glu Lys Leu Lys Ser Leu Gly
        50                  55                  60

Ile His Val Phe Asp Leu Asn Glu Val Asp Ser Leu Gly Ile Tyr Val
65                  70                  75                  80

Asp Gly Ala Asp Glu Ile Asn Gly His Met Gln Met Ile Lys Gly Gly
                85                  90                  95

Gly Ala Ala Leu Thr Arg Glu Lys Ile Ile Ala Ser Val Ala Glu Lys
            100                 105                 110

Phe Ile Cys Ile Ala Asp Ala Ser Lys Gln Val Asp Ile Leu Gly Lys
        115                 120                 125

Phe Pro Leu Pro Val Glu Val Ile Pro Met Ala Arg Ser Ala Val Ala
    130                 135                 140

Arg Gln Leu Val Lys Leu Gly Gly Arg Pro Glu Tyr Arg Gln Gly Val
145                 150                 155                 160

Val Thr Asp Asn Gly Asn Val Ile Leu Asp Val His Gly Met Glu Ile
                165                 170                 175
```

```
Leu Asp Pro Ile Ala Met Glu Asn Ala Ile Asn Ala Ile Pro Gly Val
            180                 185                 190

Val Thr Val Gly Leu Phe Ala Asn Arg Gly Ala Asp Val Ala Leu Ile
        195                 200                 205

Gly Thr Pro Asp Gly Val Lys Thr Ile Val Lys
        210                 215
```

<210> SEQ ID NO 9
<211> LENGTH: 954
<212> TYPE: DNA
<213> ORGANISM: Escherichia coli
<220> FEATURE:
<221> NAME/KEY: CDS
<222> LOCATION: (1)..(954)

<400> SEQUENCE: 9

```
atg acg gac aaa ttg acc tcc ctt cgt cag tac acc acc gta gtg gcc     48
Met Thr Asp Lys Leu Thr Ser Leu Arg Gln Tyr Thr Thr Val Val Ala
1               5                   10                  15 gac act ggg gac atc gcg gca atg aag ctg tat caa ccg cag gat gcc     96
Asp Thr Gly Asp Ile Ala Ala Met Lys Leu Tyr Gln Pro Gln Asp Ala
                20                  25                  30 aca acc aac cct tct ctc att ctt aac gca gcg cag att ccg gaa tac    144
Thr Thr Asn Pro Ser Leu Ile Leu Asn Ala Ala Gln Ile Pro Glu Tyr
            35                  40                  45 cgt aag ttg att gat gat gct gtc gcc tgg gcg aaa cag cag agc aac    192
Arg Lys Leu Ile Asp Asp Ala Val Ala Trp Ala Lys Gln Gln Ser Asn
        50                  55                  60 gat cgc gcg cag cag atc gtg gac gcg acc gac aaa ctg gca gta aat    240
Asp Arg Ala Gln Gln Ile Val Asp Ala Thr Asp Lys Leu Ala Val Asn
65                  70                  75                  80 att ggt ctg gaa atc ctg aaa ctg gtt ccg ggc cgt atc tca act gaa    288
Ile Gly Leu Glu Ile Leu Lys Leu Val Pro Gly Arg Ile Ser Thr Glu
                85                  90                  95 gtt gat gcg cgt ctt tcc tat gac acc gaa gcg tca att gcg aaa gca    336
Val Asp Ala Arg Leu Ser Tyr Asp Thr Glu Ala Ser Ile Ala Lys Ala
            100                 105                 110 aaa cgc ctg atc aaa ctc tac aac gat gct ggt att agc aac gat cgt    384
Lys Arg Leu Ile Lys Leu Tyr Asn Asp Ala Gly Ile Ser Asn Asp Arg
        115                 120                 125 att ctg atc aaa ctg gct tct acc tgg cag ggt atc cgt gct gca gaa    432
Ile Leu Ile Lys Leu Ala Ser Thr Trp Gln Gly Ile Arg Ala Ala Glu
    130                 135                 140 cag ctg gaa aaa gaa ggc atc aac tgt aac ctg acc ctg ctg ttc tcc    480
Gln Leu Glu Lys Glu Gly Ile Asn Cys Asn Leu Thr Leu Leu Phe Ser
145                 150                 155                 160 ttc gct cag gct cgt gct tgt gcg gaa gcg ggc gtg ttc ctg atc tcg    528
Phe Ala Gln Ala Arg Ala Cys Ala Glu Ala Gly Val Phe Leu Ile Ser
                165                 170                 175 ccg ttt gtt ggc cgt att ctt gac tgg tac aaa gcg aat acc gat aag    576
Pro Phe Val Gly Arg Ile Leu Asp Trp Tyr Lys Ala Asn Thr Asp Lys
            180                 185                 190 aaa gag tac gct ccg gca gaa gat ccg ggc gtg gtt tct gta tct gaa    624
Lys Glu Tyr Ala Pro Ala Glu Asp Pro Gly Val Val Ser Val Ser Glu
        195                 200                 205 atc tac cag tac tac aaa gag cac ggt tat gaa acc gtg gtt atg ggc    672
Ile Tyr Gln Tyr Tyr Lys Glu His Gly Tyr Glu Thr Val Val Met Gly
    210                 215                 220 gca agc ttc cgt aac atc ggc gaa att ctg gaa ctg gca ggc tgc gac    720
Ala Ser Phe Arg Asn Ile Gly Glu Ile Leu Glu Leu Ala Gly Cys Asp
```

```
                 225                 230                 235                 240 cgt ctg acc atc gca ccg gca ctg ctg aaa gag ctg gcg gag agc gaa       768
Arg Leu Thr Ile Ala Pro Ala Leu Leu Lys Glu Leu Ala Glu Ser Glu
                    245                 250                 255 ggg gct atc gaa cgt aaa ctg tct tac acc ggc gaa gtg aaa gcg cgt       816
Gly Ala Ile Glu Arg Lys Leu Ser Tyr Thr Gly Glu Val Lys Ala Arg
        260                 265                 270 ccg gcg cgt atc act gag tcc gag ttc ctg tgg cag cac aac cag gat       864
Pro Ala Arg Ile Thr Glu Ser Glu Phe Leu Trp Gln His Asn Gln Asp
    275                 280                 285 cca atg gca gta gat aaa ctg gcg gaa ggt atc cgt aag ttt gct att       912
Pro Met Ala Val Asp Lys Leu Ala Glu Gly Ile Arg Lys Phe Ala Ile
290                 295                 300 gac cag gaa aaa ctg gaa aaa atg atc ggc gat ctg ctg taa               954
Asp Gln Glu Lys Leu Glu Lys Met Ile Gly Asp Leu Leu
305                 310                 315
```

<210> SEQ ID NO 10
<211> LENGTH: 317
<212> TYPE: PRT
<213> ORGANISM: Escherichia coli

<400> SEQUENCE: 10

```
Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
                20                  25                  30

Thr Thr Asn Pro Ser Leu Ile Leu Asn Ala Ala Gln Ile Pro Glu Tyr
            35                  40                  45

Arg Lys Leu Ile Asp Asp Ala Val Ala Trp Ala Lys Gln Gln Ser Asn
        50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
    130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
    210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
```

```
                260                 265                 270
Pro Ala Arg Ile Thr Glu Ser Glu Phe Leu Trp Gln His Asn Gln Asp
            275                 280                 285

Pro Met Ala Val Asp Lys Leu Ala Glu Gly Ile Arg Lys Phe Ala Ile
            290                 295                 300

Asp Gln Glu Lys Leu Glu Lys Met Ile Gly Asp Leu Leu
305                 310                 315

<210> SEQ ID NO 11
<211> LENGTH: 1992
<212> TYPE: DNA
<213> ORGANISM: Escherichia coli
<220> FEATURE:
<221> NAME/KEY: CDS
<222> LOCATION: (1)..(1992)

<400> SEQUENCE: 11 atg tcc tca cgt aaa gag ctt gcc aat gct att cgt gcg ctg agc atg      48
Met Ser Ser Arg Lys Glu Leu Ala Asn Ala Ile Arg Ala Leu Ser Met
1               5                   10                  15 gac gca gta cag aaa gcc aaa tcc ggt cac ccg ggt gcc cct atg ggt      96
Asp Ala Val Gln Lys Ala Lys Ser Gly His Pro Gly Ala Pro Met Gly
                20                  25                  30 atg gct gac att gcc gaa gtc ctg tgg cgt gat ttc ctg aaa cac aac     144
Met Ala Asp Ile Ala Glu Val Leu Trp Arg Asp Phe Leu Lys His Asn
            35                  40                  45 ccg cag aat ccg tcc tgg gct gac cgt gac cgc ttc gtg ctg tcc aac     192
Pro Gln Asn Pro Ser Trp Ala Asp Arg Asp Arg Phe Val Leu Ser Asn
        50                  55                  60 ggc cac ggc tcc atg ctg atc tac agc ctg ctg cac ctc acc ggt tac     240
Gly His Gly Ser Met Leu Ile Tyr Ser Leu Leu His Leu Thr Gly Tyr
65                  70                  75                  80 gat ctg ccg atg gaa gaa ctg aaa aac ttc cgt cag ctg cac tct aaa     288
Asp Leu Pro Met Glu Glu Leu Lys Asn Phe Arg Gln Leu His Ser Lys
                85                  90                  95 act ccg ggt cac ccg gaa gtg ggt tac acc gct ggt gtg gaa acc acc     336
Thr Pro Gly His Pro Glu Val Gly Tyr Thr Ala Gly Val Glu Thr Thr
                100                 105                 110 acc ggt ccg ctg ggt cag ggt att gcc aac gca gtc ggt atg gcg att     384
Thr Gly Pro Leu Gly Gln Gly Ile Ala Asn Ala Val Gly Met Ala Ile
            115                 120                 125 gca gaa aaa acg ctg gcg gcg cag ttt aac cgt ccg ggc cac gac att     432
Ala Glu Lys Thr Leu Ala Ala Gln Phe Asn Arg Pro Gly His Asp Ile
        130                 135                 140 gtc gac cac tac acc tac gcc ttc atg ggc gac ggc tgc atg atg gaa     480
Val Asp His Tyr Thr Tyr Ala Phe Met Gly Asp Gly Cys Met Met Glu
145                 150                 155                 160 ggc atc tcc cac gaa gtt tgc tct ctg gcg ggt acg ctg aag ctg ggt     528
Gly Ile Ser His Glu Val Cys Ser Leu Ala Gly Thr Leu Lys Leu Gly
                165                 170                 175 aaa ctg att gca ttc tac gat gac aac ggt att tct atc gat ggt cac     576
Lys Leu Ile Ala Phe Tyr Asp Asp Asn Gly Ile Ser Ile Asp Gly His
                180                 185                 190 gtt gaa ggc tgg ttc acc gac gac acc gca atg cgt ttc gaa gct tac     624
Val Glu Gly Trp Phe Thr Asp Asp Thr Ala Met Arg Phe Glu Ala Tyr
            195                 200                 205 ggc tgg cac gtt att cgc gac atc gac ggt cat gac gcg gca tct atc     672
Gly Trp His Val Ile Arg Asp Ile Asp Gly His Asp Ala Ala Ser Ile
        210                 215                 220 aaa cgc gca gta gaa gaa gcg cgc gca gtg act gac aaa cct tcc ctg     720
```

```
Lys Arg Ala Val Glu Glu Ala Arg Ala Val Thr Asp Lys Pro Ser Leu
225                 230                 235                 240 ctg atg tgc aaa acc atc atc ggt ttc ggt tcc ccg aac aaa gcc ggt       768
Leu Met Cys Lys Thr Ile Ile Gly Phe Gly Ser Pro Asn Lys Ala Gly
                245                 250                 255 acc cac gac tcc cac ggt gcg ccg ctg ggc gac gct gaa att gcc ctg       816
Thr His Asp Ser His Gly Ala Pro Leu Gly Asp Ala Glu Ile Ala Leu
            260                 265                 270 acc cgc gaa caa ctg ggc tgg aaa tat gcg ccg ttc gaa atc ccg tct       864
Thr Arg Glu Gln Leu Gly Trp Lys Tyr Ala Pro Phe Glu Ile Pro Ser
        275                 280                 285 gaa atc tat gct cag tgg gat gcg aaa gaa gca ggc cag gcg aaa gaa       912
Glu Ile Tyr Ala Gln Trp Asp Ala Lys Glu Ala Gly Gln Ala Lys Glu
    290                 295                 300 tcc gca tgg aac gag aaa ttc gct gct tac gcg aaa gct tat ccg cag       960
Ser Ala Trp Asn Glu Lys Phe Ala Ala Tyr Ala Lys Ala Tyr Pro Gln
305                 310                 315                 320 gaa gcc gct gaa ttt acc cgc cgt atg aaa ggc gaa atg ccg tct gac      1008
Glu Ala Ala Glu Phe Thr Arg Arg Met Lys Gly Glu Met Pro Ser Asp
                325                 330                 335 ttc gac gct aaa gcg aaa gag ttc atc gct aaa ctg cag gct aat ccg      1056
Phe Asp Ala Lys Ala Lys Glu Phe Ile Ala Lys Leu Gln Ala Asn Pro
            340                 345                 350 gcg aaa atc gcc agc cgt aaa gcg tct cag aat gct atc gaa gcg ttc      1104
Ala Lys Ile Ala Ser Arg Lys Ala Ser Gln Asn Ala Ile Glu Ala Phe
        355                 360                 365 ggt ccg ctg ttg ccg gaa ttc ctc ggc ggt tct gct gac ctg gcg ccg      1152
Gly Pro Leu Leu Pro Glu Phe Leu Gly Gly Ser Ala Asp Leu Ala Pro
    370                 375                 380 tct aac ctg acc ctg tgg tct ggt tct aaa gca atc aac gaa gat gct      1200
Ser Asn Leu Thr Leu Trp Ser Gly Ser Lys Ala Ile Asn Glu Asp Ala
385                 390                 395                 400 gcg ggt aac tac atc cac tac ggt gtt cgc gag ttc ggt atg acc gcg      1248
Ala Gly Asn Tyr Ile His Tyr Gly Val Arg Glu Phe Gly Met Thr Ala
                405                 410                 415 att gct aac ggt atc tcc ctg cac ggt ggc ttc ctg ccg tac acc tcc      1296
Ile Ala Asn Gly Ile Ser Leu His Gly Gly Phe Leu Pro Tyr Thr Ser
            420                 425                 430 acc ttc ctg atg ttc gtg gaa tac gca cgt aac gcc gta cgt atg gct      1344
Thr Phe Leu Met Phe Val Glu Tyr Ala Arg Asn Ala Val Arg Met Ala
        435                 440                 445 gcg ctg atg aaa cag cgt cag gtg atg gtt tac acc cac gac tcc atc      1392
Ala Leu Met Lys Gln Arg Gln Val Met Val Tyr Thr His Asp Ser Ile
    450                 455                 460 ggt ctg ggc gaa gac ggc ccg act cac cag ccg gtt gag cag gtc gct      1440
Gly Leu Gly Glu Asp Gly Pro Thr His Gln Pro Val Glu Gln Val Ala
465                 470                 475                 480 tct ctg cgc gta acc ccg aac atg tct aca tgg cgt ccg tgt gac cag      1488
Ser Leu Arg Val Thr Pro Asn Met Ser Thr Trp Arg Pro Cys Asp Gln
                485                 490                 495 gtt gaa tcc gcg gtc gcg tgg aaa tac ggt gtt gag cgt cag gac ggc      1536
Val Glu Ser Ala Val Ala Trp Lys Tyr Gly Val Glu Arg Gln Asp Gly
            500                 505                 510 ccg acc gca ctg atc ctc tcc cgt cag aac ctg gcg cag cag gaa cga      1584
Pro Thr Ala Leu Ile Leu Ser Arg Gln Asn Leu Ala Gln Gln Glu Arg
        515                 520                 525 act gaa gag caa ctg gca aac atc gcg cgc ggt ggt tat gtg ctg aaa      1632
Thr Glu Glu Gln Leu Ala Asn Ile Ala Arg Gly Gly Tyr Val Leu Lys
    530                 535                 540
```

```
gac tgc gcc ggt cag ccg gaa ctg att ttc atc gct acc ggt tca gaa      1680
Asp Cys Ala Gly Gln Pro Glu Leu Ile Phe Ile Ala Thr Gly Ser Glu
545                 550                 555                 560 gtt gaa ctg gct gtt gct gcc tac gaa aaa ctg act gcc gaa ggc gtg      1728
Val Glu Leu Ala Val Ala Ala Tyr Glu Lys Leu Thr Ala Glu Gly Val
                565                 570                 575 aaa gcg cgc gtg gtg tcc atg ccg tct acc gac gca ttt gac aag cag      1776
Lys Ala Arg Val Val Ser Met Pro Ser Thr Asp Ala Phe Asp Lys Gln
            580                 585                 590 gat gct gct tac cgt gaa tcc gta ctg ccg aaa gcg gtt act gca cgc      1824
Asp Ala Ala Tyr Arg Glu Ser Val Leu Pro Lys Ala Val Thr Ala Arg
        595                 600                 605 gtt gct gta gaa gcg ggt att gct gac tac tgg tac aag tat gtt ggc      1872
Val Ala Val Glu Ala Gly Ile Ala Asp Tyr Trp Tyr Lys Tyr Val Gly
    610                 615                 620 ctg aac ggt gct atc gtc ggt atg acc acc ttc ggt gaa tct gct ccg      1920
Leu Asn Gly Ala Ile Val Gly Met Thr Thr Phe Gly Glu Ser Ala Pro
625                 630                 635                 640 gca gag ctg ctg ttt gaa gag ttc ggc ttc act gtt gat aac gtt gtt      1968
Ala Glu Leu Leu Phe Glu Glu Phe Gly Phe Thr Val Asp Asn Val Val
                645                 650                 655 gcg aaa gca aaa gaa ctg ctg taa                                      1992
Ala Lys Ala Lys Glu Leu Leu
            660
```

<210> SEQ ID NO 12
<211> LENGTH: 663
<212> TYPE: PRT
<213> ORGANISM: Escherichia coli

<400> SEQUENCE: 12

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205
```

```
Gly Trp His Val Ile Arg Asp Ile Asp Gly His Asp Ala Ala Ser Ile
    210                 215                 220
Lys Arg Ala Val Glu Glu Ala Arg Ala Val Thr Asp Lys Pro Ser Leu
225                 230                 235                 240
Leu Met Cys Lys Thr Ile Ile Gly Phe Gly Ser Pro Asn Lys Ala Gly
                245                 250                 255
Thr His Asp Ser His Gly Ala Pro Leu Gly Asp Ala Glu Ile Ala Leu
            260                 265                 270
Thr Arg Glu Gln Leu Gly Trp Lys Tyr Ala Pro Phe Glu Ile Pro Ser
        275                 280                 285
Glu Ile Tyr Ala Gln Trp Asp Ala Lys Glu Ala Gly Gln Ala Lys Glu
    290                 295                 300
Ser Ala Trp Asn Glu Lys Phe Ala Ala Tyr Ala Lys Ala Tyr Pro Gln
305                 310                 315                 320
Glu Ala Ala Glu Phe Thr Arg Arg Met Lys Gly Met Pro Ser Asp
                325                 330                 335
Phe Asp Ala Lys Ala Lys Glu Phe Ile Ala Lys Leu Gln Ala Asn Pro
            340                 345                 350
Ala Lys Ile Ala Ser Arg Lys Ala Ser Gln Asn Ala Ile Glu Ala Phe
        355                 360                 365
Gly Pro Leu Leu Pro Glu Phe Leu Gly Gly Ser Ala Asp Leu Ala Pro
    370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ser Leu His Gly Gly Phe Leu Pro Tyr Thr Ser
            420                 425                 430
Thr Phe Leu Met Phe Val Glu Tyr Ala Arg Asn Ala Val Arg Met Ala
        435                 440                 445
Ala Leu Met Lys Gln Arg Gln Val Met Val Tyr Thr His Asp Ser Ile
    450                 455                 460
Gly Leu Gly Glu Asp Gly Pro Thr His Gln Pro Val Glu Gln Val Ala
465                 470                 475                 480
Ser Leu Arg Val Thr Pro Asn Met Ser Thr Trp Arg Pro Cys Asp Gln
                485                 490                 495
Val Glu Ser Ala Val Ala Trp Lys Tyr Gly Val Glu Arg Gln Asp Gly
            500                 505                 510
Pro Thr Ala Leu Ile Leu Ser Arg Gln Asn Leu Ala Gln Gln Glu Arg
        515                 520                 525
Thr Glu Glu Gln Leu Ala Asn Ile Ala Arg Gly Gly Tyr Val Leu Lys
    530                 535                 540
Asp Cys Ala Gly Gln Pro Glu Leu Ile Phe Ile Ala Thr Gly Ser Glu
545                 550                 555                 560
Val Glu Leu Ala Val Ala Ala Tyr Glu Lys Leu Thr Ala Glu Gly Val
                565                 570                 575
Lys Ala Arg Val Val Ser Met Pro Ser Thr Asp Ala Phe Asp Lys Gln
            580                 585                 590
Asp Ala Ala Tyr Arg Glu Ser Val Leu Pro Lys Ala Val Thr Ala Arg
        595                 600                 605
Val Ala Val Glu Ala Gly Ile Ala Asp Tyr Trp Tyr Lys Tyr Val Gly
    610                 615                 620
Leu Asn Gly Ala Ile Val Gly Met Thr Thr Phe Gly Glu Ser Ala Pro
```

```
                625                 630                 635                 640
Ala Glu Leu Leu Phe Glu Glu Phe Gly Phe Thr Val Asp Asn Val Val
                        645                 650                 655
Ala Lys Ala Lys Glu Leu Leu
                660

<210> SEQ ID NO 13
<211> LENGTH: 633
<212> TYPE: DNA
<213> ORGANISM: Bacillus subtilis
<220> FEATURE:
<221> NAME/KEY: CDS
<222> LOCATION: (1)..(633)

<400> SEQUENCE: 13 atg gaa tta cag ctt gca tta gac ctc gtc aac atc cca gaa gcc att          48
Met Glu Leu Gln Leu Ala Leu Asp Leu Val Asn Ile Pro Glu Ala Ile
1               5                   10                  15 gag ctc gtc aaa gag gta gaa caa tac atc gac gta gtt gaa atc gga          96
Glu Leu Val Lys Glu Val Glu Gln Tyr Ile Asp Val Val Glu Ile Gly
            20                  25                  30 aca ccg gtc gtc att aat gaa ggc cta aga gcc gtt aaa gaa tta aaa         144
Thr Pro Val Val Ile Asn Glu Gly Leu Arg Ala Val Lys Glu Leu Lys
        35                  40                  45 gaa gca ttt cct caa ttg aag gtt ctt gca gac ctg aaa atc atg gat         192
Glu Ala Phe Pro Gln Leu Lys Val Leu Ala Asp Leu Lys Ile Met Asp
    50                  55                  60 gcc gga ggc tac gaa att atg aaa gcg tcg gaa gca ggc gct gac atc         240
Ala Gly Gly Tyr Glu Ile Met Lys Ala Ser Glu Ala Gly Ala Asp Ile
65                  70                  75                  80 atc acc gtt tta ggg gct aca gac gac gca acg att aaa ggc gca gta         288
Ile Thr Val Leu Gly Ala Thr Asp Asp Ala Thr Ile Lys Gly Ala Val
                85                  90                  95 gaa gaa gcc aaa aaa caa aag aag aaa atc tta gtg gac atg att aac         336
Glu Glu Ala Lys Lys Gln Lys Lys Lys Ile Leu Val Asp Met Ile Asn
            100                 105                 110 gtg aaa gat atc gag tcc cgt gcg caa gaa att gac gca ctc ggt gtt         384
Val Lys Asp Ile Glu Ser Arg Ala Gln Glu Ile Asp Ala Leu Gly Val
        115                 120                 125 gac tac atc tgc gtc cac act ggc tat gat ctt caa gca gag ggc aag         432
Asp Tyr Ile Cys Val His Thr Gly Tyr Asp Leu Gln Ala Glu Gly Lys
    130                 135                 140 aac tct ttc gaa gaa tta acg aca atc aaa aac acc gta aaa aac gca         480
Asn Ser Phe Glu Glu Leu Thr Thr Ile Lys Asn Thr Val Lys Asn Ala
145                 150                 155                 160 aaa acc gca atc gcg ggc ggc atc aaa ctt gat aca ctg cca gaa gtg         528
Lys Thr Ala Ile Ala Gly Gly Ile Lys Leu Asp Thr Leu Pro Glu Val
                165                 170                 175 atc aag caa aac ccc gac ctt gtc att gtt ggg ggc gga att aca agc         576
Ile Lys Gln Asn Pro Asp Leu Val Ile Val Gly Gly Gly Ile Thr Ser
            180                 185                 190 gca gct gat aag gca gaa aca gct tca aaa atg aag cag ctg att gtc         624
Ala Ala Asp Lys Ala Glu Thr Ala Ser Lys Met Lys Gln Leu Ile Val
        195                 200                 205 caa gga taa                                                             633
Gln Gly
    210

<210> SEQ ID NO 14
<211> LENGTH: 210
<212> TYPE: PRT
```

<213> ORGANISM: Bacillus subtilis

<400> SEQUENCE: 14

```
Met Glu Leu Gln Leu Ala Leu Asp Leu Val Asn Ile Pro Glu Ala Ile
1               5                   10                  15

Glu Leu Val Lys Glu Val Glu Gln Tyr Ile Asp Val Val Glu Ile Gly
            20                  25                  30

Thr Pro Val Val Ile Asn Glu Gly Leu Arg Ala Val Lys Glu Leu Lys
        35                  40                  45

Glu Ala Phe Pro Gln Leu Lys Val Leu Ala Asp Leu Lys Ile Met Asp
    50                  55                  60

Ala Gly Gly Tyr Glu Ile Met Lys Ala Ser Glu Ala Gly Ala Asp Ile
65                  70                  75                  80

Ile Thr Val Leu Gly Ala Thr Asp Ala Thr Ile Lys Gly Ala Val
                85                  90                  95

Glu Glu Ala Lys Lys Gln Lys Lys Ile Leu Val Asp Met Ile Asn
            100                 105                 110

Val Lys Asp Ile Glu Ser Arg Ala Gln Glu Ile Asp Ala Leu Gly Val
        115                 120                 125

Asp Tyr Ile Cys Val His Thr Gly Tyr Asp Leu Gln Ala Glu Gly Lys
    130                 135                 140

Asn Ser Phe Glu Glu Leu Thr Thr Ile Lys Asn Thr Val Lys Asn Ala
145                 150                 155                 160

Lys Thr Ala Ile Ala Gly Gly Ile Lys Leu Asp Thr Leu Pro Glu Val
                165                 170                 175

Ile Lys Gln Asn Pro Asp Leu Val Ile Val Gly Gly Ile Thr Ser
            180                 185                 190

Ala Ala Asp Lys Ala Glu Thr Ala Ser Lys Met Lys Gln Leu Ile Val
        195                 200                 205

Gln Gly
    210
```

<210> SEQ ID NO 15
<211> LENGTH: 687
<212> TYPE: DNA
<213> ORGANISM: M. flagettus
<220> FEATURE:
<221> NAME/KEY: CDS
<222> LOCATION: (1)..(687)

<400> SEQUENCE: 15

```
gtg gca aaa cca tta gtt caa atg gca tta gat tca cta gat ttc gat      48
Val Ala Lys Pro Leu Val Gln Met Ala Leu Asp Ser Leu Asp Phe Asp
1               5                   10                  15 cag act gta gcg ctt gct acg act gtt gca cca cat gtt gat att ctt      96
Gln Thr Val Ala Leu Ala Thr Thr Val Ala Pro His Val Asp Ile Leu
            20                  25                  30 gaa atc ggt act cct tgt atc aag tac aac ggt atc aag ttg ctg gag     144
Glu Ile Gly Thr Pro Cys Ile Lys Tyr Asn Gly Ile Lys Leu Leu Glu
        35                  40                  45 act ctc cgc gca aag ttc cct aac aac aag atc ctg gtt gac ctg aag     192
Thr Leu Arg Ala Lys Phe Pro Asn Asn Lys Ile Leu Val Asp Leu Lys
    50                  55                  60 acc atg gat gct ggt ttt tac gaa gca gag cct ttc tac aag gca ggt     240
Thr Met Asp Ala Gly Phe Tyr Glu Ala Glu Pro Phe Tyr Lys Ala Gly
65                  70                  75                  80 gcc gac atc gtg acc gtg ctc ggc act gct gac att ggc acg atc aaa     288
Ala Asp Ile Val Thr Val Leu Gly Thr Ala Asp Ile Gly Thr Ile Lys
```

```
                          85                  90                  95
ggc gtc att gat gtt gcc aac aaa tac ggc aag aag gct caa gtc gac      336
Gly Val Ile Asp Val Ala Asn Lys Tyr Gly Lys Lys Ala Gln Val Asp
            100                 105                 110 ctg atc aac gtg act gac aag gct gca cgc acc aag gaa gtg gcc aag      384
Leu Ile Asn Val Thr Asp Lys Ala Ala Arg Thr Lys Glu Val Ala Lys
        115                 120                 125 ctc ggc gct cac atc att ggc gtt cac act ggt ttg gat caa cag gct      432
Leu Gly Ala His Ile Ile Gly Val His Thr Gly Leu Asp Gln Gln Ala
    130                 135                 140 gct ggt cag aca ccg ttt gcc gat ctc aac ctt gtt tcc agc ctg aac      480
Ala Gly Gln Thr Pro Phe Ala Asp Leu Asn Leu Val Ser Ser Leu Asn
145                 150                 155                 160 ctg ggt gtt gac att tcc gta gct ggt ggc gtg aag gcg act acc gcc      528
Leu Gly Val Asp Ile Ser Val Ala Gly Gly Val Lys Ala Thr Thr Ala
                165                 170                 175 aaa caa gtg gtt gat gca ggt gcc aca att gtt gtt gct ggt gcg gct      576
Lys Gln Val Val Asp Ala Gly Ala Thr Ile Val Val Ala Gly Ala Ala
            180                 185                 190 atc tat ggt gct gcc gat cct gct gct gct gct gct gaa atc agc gct      624
Ile Tyr Gly Ala Ala Asp Pro Ala Ala Ala Ala Ala Glu Ile Ser Ala
        195                 200                 205 gcg gcc aag ggt aca caa agc agt ggt ggc ctg ttt ggc tgg ctg aag      672
Ala Ala Lys Gly Thr Gln Ser Ser Gly Gly Leu Phe Gly Trp Leu Lys
    210                 215                 220 aaa ctg ttc agc taa                                                  687
Lys Leu Phe Ser
225
```

<210> SEQ ID NO 16
<211> LENGTH: 228
<212> TYPE: PRT
<213> ORGANISM: M. flagettus

<400> SEQUENCE: 16

```
Val Ala Lys Pro Leu Val Gln Met Ala Leu Asp Ser Leu Asp Phe Asp
1               5                   10                  15

Gln Thr Val Ala Leu Ala Thr Thr Val Ala Pro His Val Asp Ile Leu
            20                  25                  30

Glu Ile Gly Thr Pro Cys Ile Lys Tyr Asn Gly Ile Lys Leu Leu Glu
        35                  40                  45

Thr Leu Arg Ala Lys Phe Pro Asn Asn Lys Ile Leu Val Asp Leu Lys
    50                  55                  60

Thr Met Asp Ala Gly Phe Tyr Glu Ala Glu Pro Phe Tyr Lys Ala Gly
65                  70                  75                  80

Ala Asp Ile Val Thr Val Leu Gly Thr Ala Asp Ile Gly Thr Ile Lys
                85                  90                  95

Gly Val Ile Asp Val Ala Asn Lys Tyr Gly Lys Lys Ala Gln Val Asp
            100                 105                 110

Leu Ile Asn Val Thr Asp Lys Ala Ala Arg Thr Lys Glu Val Ala Lys
        115                 120                 125

Leu Gly Ala His Ile Ile Gly Val His Thr Gly Leu Asp Gln Gln Ala
    130                 135                 140

Ala Gly Gln Thr Pro Phe Ala Asp Leu Asn Leu Val Ser Ser Leu Asn
145                 150                 155                 160

Leu Gly Val Asp Ile Ser Val Ala Gly Gly Val Lys Ala Thr Thr Ala
                165                 170                 175
```

```
Lys Gln Val Val Asp Ala Gly Ala Thr Ile Val Val Ala Gly Ala Ala
            180                 185                 190

Ile Tyr Gly Ala Ala Asp Pro Ala Ala Ala Ala Glu Ile Ser Ala
        195                 200                 205

Ala Ala Lys Gly Thr Gln Ser Ser Gly Gly Leu Phe Gly Trp Leu Lys
        210                 215                 220

Lys Leu Phe Ser
225

<210> SEQ ID NO 17
<211> LENGTH: 2121
<212> TYPE: DNA
<213> ORGANISM: C. boindii
<220> FEATURE:
<221> NAME/KEY: CDS
<222> LOCATION: (1)..(2121)

<400> SEQUENCE: 17 atg gct ctc gca aaa gct gct tca att aac gat gat atc cat gat tta        48
Met Ala Leu Ala Lys Ala Ala Ser Ile Asn Asp Asp Ile His Asp Leu
1               5                   10                  15 aca atg aga gca ttc cgt tgt tat gtc ttg gat tta gtt gaa caa tat        96
Thr Met Arg Ala Phe Arg Cys Tyr Val Leu Asp Leu Val Glu Gln Tyr
            20                  25                  30 gaa ggt ggt cat cct ggt tct gct atg ggt atg gtt gcc atg ggt att       144
Glu Gly Gly His Pro Gly Ser Ala Met Gly Met Val Ala Met Gly Ile
        35                  40                  45 gca tta tgg aaa tat aca atg aaa tat tct aca aat gat cca aca tgg       192
Ala Leu Trp Lys Tyr Thr Met Lys Tyr Ser Thr Asn Asp Pro Thr Trp
    50                  55                  60 ttc aat cgt gat aga ttt gtt tta tca aat ggt cat gtt tgt tta ttt       240
Phe Asn Arg Asp Arg Phe Val Leu Ser Asn Gly His Val Cys Leu Phe
65                  70                  75                  80 caa tat tta ttt caa cat tta tca ggt ttg aaa tct atg act gaa aag       288
Gln Tyr Leu Phe Gln His Leu Ser Gly Leu Lys Ser Met Thr Glu Lys
                85                  90                  95 caa tta aaa tct tat cat tca tca gat tac cat tct aaa tgt cct gga       336
Gln Leu Lys Ser Tyr His Ser Ser Asp Tyr His Ser Lys Cys Pro Gly
            100                 105                 110 cat cca gaa att gaa aat gaa gct gtt gaa gtt act act ggt cca tta       384
His Pro Glu Ile Glu Asn Glu Ala Val Glu Val Thr Thr Gly Pro Leu
        115                 120                 125 ggt caa ggt att tct aat tct gtt ggt tta gct att gca tct aaa aat       432
Gly Gln Gly Ile Ser Asn Ser Val Gly Leu Ala Ile Ala Ser Lys Asn
    130                 135                 140 ttg ggt gca tta tat aac aag cca gga tat gaa gtt gtt aat aat act       480
Leu Gly Ala Leu Tyr Asn Lys Pro Gly Tyr Glu Val Val Asn Asn Thr
145                 150                 155                 160 aca tat tgt att gtt ggt gat gct tgt tta caa gaa ggt cca gca tta       528
Thr Tyr Cys Ile Val Gly Asp Ala Cys Leu Gln Glu Gly Pro Ala Leu
                165                 170                 175 gaa tct att tca ttt gca ggt cat tta gga tta gat aat tta gtt gtt       576
Glu Ser Ile Ser Phe Ala Gly His Leu Gly Leu Asp Asn Leu Val Val
            180                 185                 190 att tat gat aac aat caa gtt tgt tgt gat ggt tct gtt gat att gct       624
Ile Tyr Asp Asn Asn Gln Val Cys Cys Asp Gly Ser Val Asp Ile Ala
        195                 200                 205 aat act gaa gat att tca gct aag ttt aga gct tgt aat tgg aat gtt       672
Asn Thr Glu Asp Ile Ser Ala Lys Phe Arg Ala Cys Asn Trp Asn Val
    210                 215                 220
```

```
att gaa gtt gaa gat ggt gct aga gat gtt gct act att gtc aag gca      720
Ile Glu Val Glu Asp Gly Ala Arg Asp Val Ala Thr Ile Val Lys Ala
225                 230                 235                 240 ttg gaa cta gct ggt gct gaa aag aat aga cca aca tta att aat gtt      768
Leu Glu Leu Ala Gly Ala Glu Lys Asn Arg Pro Thr Leu Ile Asn Val
                245                 250                 255 cgt act att att ggt act gat tca gct ttc caa aat cat tgt gct gct      816
Arg Thr Ile Ile Gly Thr Asp Ser Ala Phe Gln Asn His Cys Ala Ala
            260                 265                 270 cat ggt agt gct tta ggt gaa gaa ggt att aga gaa ttg aaa atc aaa      864
His Gly Ser Ala Leu Gly Glu Glu Gly Ile Arg Glu Leu Lys Ile Lys
        275                 280                 285 tat ggt ttt aat cca tct caa aaa ttc cat ttt cca caa gaa gtt tat      912
Tyr Gly Phe Asn Pro Ser Gln Lys Phe His Phe Pro Gln Glu Val Tyr
    290                 295                 300 gat ttc ttt agt gat att cca gct aaa ggt gac gaa tat gtt tct aat      960
Asp Phe Phe Ser Asp Ile Pro Ala Lys Gly Asp Glu Tyr Val Ser Asn
305                 310                 315                 320 tgg aat aaa tta gtt agt agt tat gtt aaa gaa ttt cct gaa tta gga     1008
Trp Asn Lys Leu Val Ser Ser Tyr Val Lys Glu Phe Pro Glu Leu Gly
                325                 330                 335 gct gaa ttt caa tca aga gtt aaa ggt gaa tta cca aag aat tgg aaa     1056
Ala Glu Phe Gln Ser Arg Val Lys Gly Glu Leu Pro Lys Asn Trp Lys
            340                 345                 350 tca tta tta cca aat aat tta cca aat gaa gat aca gca aca aga aca     1104
Ser Leu Leu Pro Asn Asn Leu Pro Asn Glu Asp Thr Ala Thr Arg Thr
        355                 360                 365 tca gct aga gct atg gtt aga gca tta gct aaa gat gtt cca aat gtt     1152
Ser Ala Arg Ala Met Val Arg Ala Leu Ala Lys Asp Val Pro Asn Val
370                 375                 380 att gct ggt tca gca gat tta tca gtt tcg gtt aat tta cca tgg cct     1200
Ile Ala Gly Ser Ala Asp Leu Ser Val Ser Val Asn Leu Pro Trp Pro
385                 390                 395                 400 gga tct aaa tat ttt gaa aat cca caa tta gca aca caa tgt gga tta     1248
Gly Ser Lys Tyr Phe Glu Asn Pro Gln Leu Ala Thr Gln Cys Gly Leu
                405                 410                 415 gct ggt gat tat tct ggt aga tat gtt gaa ttt ggt att aga gaa cat     1296
Ala Gly Asp Tyr Ser Gly Arg Tyr Val Glu Phe Gly Ile Arg Glu His
            420                 425                 430 tgt atg tgt gct att gct aat ggt tta gct gct ttt aac aaa ggt aca     1344
Cys Met Cys Ala Ile Ala Asn Gly Leu Ala Ala Phe Asn Lys Gly Thr
        435                 440                 445 ttt tta cca att act tca tca ttt tat atg ttt tat ctc tat gca gcc     1392
Phe Leu Pro Ile Thr Ser Ser Phe Tyr Met Phe Tyr Leu Tyr Ala Ala
450                 455                 460 cca gca tta aga atg gct gca tta caa gaa tta aag gca att cat att     1440
Pro Ala Leu Arg Met Ala Ala Leu Gln Glu Leu Lys Ala Ile His Ile
465                 470                 475                 480 gct aca cat gat tct att ggt gct ggt gaa gat gga cca aca cat caa     1488
Ala Thr His Asp Ser Ile Gly Ala Gly Glu Asp Gly Pro Thr His Gln
                485                 490                 495 cct att gca caa tct gct tta tgg aga gca atg cct aat ttc tat tat     1536
Pro Ile Ala Gln Ser Ala Leu Trp Arg Ala Met Pro Asn Phe Tyr Tyr
            500                 505                 510 atg aga cca ggt gat gct agt gaa gta cgt gga tta ttt gaa aaa gct     1584
Met Arg Pro Gly Asp Ala Ser Glu Val Arg Gly Leu Phe Glu Lys Ala
        515                 520                 525 gtt gaa tta cca tta tct aca tta ttt tca tta tct aga cat gaa gtt     1632
Val Glu Leu Pro Leu Ser Thr Leu Phe Ser Leu Ser Arg His Glu Val
530                 535                 540
```

```
cca caa tat cca ggt aaa tca agt att gaa tta gct aaa aga ggt ggt    1680
Pro Gln Tyr Pro Gly Lys Ser Ser Ile Glu Leu Ala Lys Arg Gly Gly
545                 550                 555                 560 tat gta ttt gaa gat gct aaa gat gct gat att caa tta att ggt gct    1728
Tyr Val Phe Glu Asp Ala Lys Asp Ala Asp Ile Gln Leu Ile Gly Ala
                565                 570                 575 ggt tca gaa tta gaa caa gct gtt aaa act gct aga att tta aga tct    1776
Gly Ser Glu Leu Glu Gln Ala Val Lys Thr Ala Arg Ile Leu Arg Ser
            580                 585                 590 aga gga tta aaa gtt cgt att tta tct ttc cca tgt caa cgt tta ttt    1824
Arg Gly Leu Lys Val Arg Ile Leu Ser Phe Pro Cys Gln Arg Leu Phe
        595                 600                 605 gat gaa caa tct gtt gga tat aga aga tct gtt tta caa agg ggt aaa    1872
Asp Glu Gln Ser Val Gly Tyr Arg Arg Ser Val Leu Gln Arg Gly Lys
    610                 615                 620 gtt cca act gtt gtt att gaa gct tat gtt gct tat ggt tgg gaa aga    1920
Val Pro Thr Val Val Ile Glu Ala Tyr Val Ala Tyr Gly Trp Glu Arg
625                 630                 635                 640 tat gct aca gca ggt tat act atg aat aca ttt ggt aaa tca tta cct    1968
Tyr Ala Thr Ala Gly Tyr Thr Met Asn Thr Phe Gly Lys Ser Leu Pro
                645                 650                 655 gtt gaa gat gtt tat gaa tat ttt ggt ttt aac cca tct gaa att tct    2016
Val Glu Asp Val Tyr Glu Tyr Phe Gly Phe Asn Pro Ser Glu Ile Ser
            660                 665                 670 aaa aaa att gaa ggt tat gtt aga gca gtt aaa gct aat cct gat tta    2064
Lys Lys Ile Glu Gly Tyr Val Arg Ala Val Lys Ala Asn Pro Asp Leu
        675                 680                 685 tta tat gaa ttt att gat tta acc gaa aaa cca aaa cat gat caa aat    2112
Leu Tyr Glu Phe Ile Asp Leu Thr Glu Lys Pro Lys His Asp Gln Asn
    690                 695                 700 cat tta taa                                                         2121
His Leu
705

<210> SEQ ID NO 18
<211> LENGTH: 706
<212> TYPE: PRT
<213> ORGANISM: C. boindii

<400> SEQUENCE: 18

Met Ala Leu Ala Lys Ala Ala Ser Ile Asn Asp Asp Ile His Asp Leu
1               5                   10                  15

Thr Met Arg Ala Phe Arg Cys Tyr Val Leu Asp Leu Val Glu Gln Tyr
                20                  25                  30

Glu Gly Gly His Pro Gly Ser Ala Met Gly Met Val Ala Met Gly Ile
            35                  40                  45

Ala Leu Trp Lys Tyr Thr Met Lys Tyr Ser Thr Asn Asp Pro Thr Trp
        50                  55                  60

Phe Asn Arg Asp Arg Phe Val Leu Ser Asn Gly His Val Cys Leu Phe
65                  70                  75                  80

Gln Tyr Leu Phe Gln His Leu Ser Gly Leu Lys Ser Met Thr Glu Lys
                85                  90                  95

Gln Leu Lys Ser Tyr His Ser Ser Asp Tyr His Ser Lys Cys Pro Gly
            100                 105                 110

His Pro Glu Ile Glu Asn Glu Ala Val Glu Val Thr Thr Gly Pro Leu
        115                 120                 125

Gly Gln Gly Ile Ser Asn Ser Val Gly Leu Ala Ile Ala Ser Lys Asn
    130                 135                 140
```

```
Leu Gly Ala Leu Tyr Asn Lys Pro Gly Tyr Glu Val Val Asn Asn Thr
145                 150                 155                 160

Thr Tyr Cys Ile Val Gly Asp Ala Cys Leu Gln Glu Gly Pro Ala Leu
            165                 170                 175

Glu Ser Ile Ser Phe Ala Gly His Leu Gly Leu Asp Asn Leu Val Val
            180                 185                 190

Ile Tyr Asp Asn Gln Val Cys Cys Asp Gly Ser Val Asp Ile Ala
            195                 200                 205

Asn Thr Glu Asp Ile Ser Ala Lys Phe Arg Ala Cys Asn Trp Asn Val
            210                 215                 220

Ile Glu Val Glu Asp Gly Ala Arg Asp Val Ala Thr Ile Val Lys Ala
225                 230                 235                 240

Leu Glu Leu Ala Gly Ala Glu Lys Asn Arg Pro Thr Leu Ile Asn Val
            245                 250                 255

Arg Thr Ile Ile Gly Thr Asp Ser Ala Phe Gln Asn His Cys Ala Ala
            260                 265                 270

His Gly Ser Ala Leu Gly Glu Gly Ile Arg Glu Leu Lys Ile Lys
            275                 280                 285

Tyr Gly Phe Asn Pro Ser Gln Lys Phe His Pro Gln Glu Val Tyr
290                 295                 300

Asp Phe Phe Ser Asp Ile Pro Ala Lys Gly Asp Glu Tyr Val Ser Asn
305                 310                 315                 320

Trp Asn Lys Leu Val Ser Ser Tyr Val Lys Glu Phe Pro Glu Leu Gly
            325                 330                 335

Ala Glu Phe Gln Ser Arg Val Lys Gly Glu Leu Pro Lys Asn Trp Lys
            340                 345                 350

Ser Leu Leu Pro Asn Asn Leu Pro Asn Glu Asp Thr Ala Thr Arg Thr
            355                 360                 365

Ser Ala Arg Ala Met Val Arg Ala Leu Ala Lys Asp Val Pro Asn Val
370                 375                 380

Ile Ala Gly Ser Ala Asp Leu Ser Val Ser Val Asn Leu Pro Trp Pro
385                 390                 395                 400

Gly Ser Lys Tyr Phe Glu Asn Pro Gln Leu Ala Thr Gln Cys Gly Leu
            405                 410                 415

Ala Gly Asp Tyr Ser Gly Arg Tyr Val Glu Phe Gly Ile Arg Glu His
            420                 425                 430

Cys Met Cys Ala Ile Ala Asn Gly Leu Ala Ala Phe Asn Lys Gly Thr
            435                 440                 445

Phe Leu Pro Ile Thr Ser Ser Phe Tyr Met Phe Tyr Leu Tyr Ala Ala
            450                 455                 460

Pro Ala Leu Arg Met Ala Ala Leu Gln Glu Leu Lys Ala Ile His Ile
465                 470                 475                 480

Ala Thr His Asp Ser Ile Gly Ala Gly Glu Asp Gly Pro Thr His Gln
            485                 490                 495

Pro Ile Ala Gln Ser Ala Leu Trp Arg Ala Met Pro Asn Phe Tyr Tyr
            500                 505                 510

Met Arg Pro Gly Asp Ala Ser Glu Val Arg Gly Leu Phe Glu Lys Ala
            515                 520                 525

Val Glu Leu Pro Leu Ser Thr Leu Phe Ser Leu Ser Arg His Glu Val
            530                 535                 540

Pro Gln Tyr Pro Gly Lys Ser Ser Ile Glu Leu Ala Lys Arg Gly Gly
545                 550                 555                 560
```

```
Tyr Val Phe Glu Asp Ala Lys Asp Ala Asp Ile Gln Leu Ile Gly Ala
            565                 570                 575

Gly Ser Glu Leu Glu Gln Ala Val Lys Thr Ala Arg Ile Leu Arg Ser
        580                 585                 590

Arg Gly Leu Lys Val Arg Ile Leu Ser Phe Pro Cys Gln Arg Leu Phe
    595                 600                 605

Asp Glu Gln Ser Val Gly Tyr Arg Arg Ser Val Leu Gln Arg Gly Lys
610                 615                 620

Val Pro Thr Val Val Ile Glu Ala Tyr Val Tyr Gly Trp Glu Arg
625                 630                 635                 640

Tyr Ala Thr Ala Gly Tyr Thr Met Asn Thr Phe Gly Lys Ser Leu Pro
                645                 650                 655

Val Glu Asp Val Tyr Glu Tyr Phe Gly Phe Asn Pro Ser Glu Ile Ser
            660                 665                 670

Lys Lys Ile Glu Gly Tyr Val Arg Ala Val Lys Ala Asn Pro Asp Leu
        675                 680                 685

Leu Tyr Glu Phe Ile Asp Leu Thr Glu Lys Pro Lys His Asp Gln Asn
    690                 695                 700

His Leu
705

<210> SEQ ID NO 19
<211> LENGTH: 663
<212> TYPE: DNA
<213> ORGANISM: Salmonella enterica
<220> FEATURE:
<221> NAME/KEY: CDS
<222> LOCATION: (1)..(663)

<400> SEQUENCE: 19 atg gaa ctc tat ctg gat acc gct aac gtg gcg gaa gtt gaa cgt ctg      48
Met Glu Leu Tyr Leu Asp Thr Ala Asn Val Ala Glu Val Glu Arg Leu
1               5                   10                  15 gcg cgc att ttc ccg att gcc ggc gtc acc acc aat cca agc att gtg      96
Ala Arg Ile Phe Pro Ile Ala Gly Val Thr Thr Asn Pro Ser Ile Val
            20                  25                  30 gca gcc agc aaa gaa tct atc tgg gat gtg ctg ccc agg ctg caa aac     144
Ala Ala Ser Lys Glu Ser Ile Trp Asp Val Leu Pro Arg Leu Gln Asn
        35                  40                  45 gcc atc ggc gaa gaa ggc act tta ttt gcg cag acc atg agc cgc gac     192
Ala Ile Gly Glu Glu Gly Thr Leu Phe Ala Gln Thr Met Ser Arg Asp
    50                  55                  60 gcg aaa ggg atg gtg gaa gaa gcc aaa cga ctg aat aac gcc atc ccc     240
Ala Lys Gly Met Val Glu Glu Ala Lys Arg Leu Asn Asn Ala Ile Pro
65                  70                  75                  80 ggc att gtg gtt aaa att ccg gtg acc gcc gaa ggt ctt gca gcg att     288
Gly Ile Val Val Lys Ile Pro Val Thr Ala Glu Gly Leu Ala Ala Ile
                85                  90                  95 aaa ttg ctg aaa aaa gaa ggc atc gtg acg ctg ggc acc gcc gtc tac     336
Lys Leu Leu Lys Lys Glu Gly Ile Val Thr Leu Gly Thr Ala Val Tyr
            100                 105                 110 agc gca tcg cag ggc ctg ctg gcg gcg ctg gcg ggc gca aaa tat gtc     384
Ser Ala Ser Gln Gly Leu Leu Ala Ala Leu Ala Gly Ala Lys Tyr Val
        115                 120                 125 gct ccc tac gtc aac cgc gtt gat gcg cag ggc ggc gat ggc att cgt     432
Ala Pro Tyr Val Asn Arg Val Asp Ala Gln Gly Gly Asp Gly Ile Arg
    130                 135                 140 atg gtt cag gag ctg caa acg cta ctg gaa cat cac gcg ccc gac agc     480
Met Val Gln Glu Leu Gln Thr Leu Leu Glu His His Ala Pro Asp Ser
```

```
atg gta ctg gcg gcc agc ttt aaa acg ccg cgg cag gcg ctg gat tgc      528
Met Val Leu Ala Ala Ser Phe Lys Thr Pro Arg Gln Ala Leu Asp Cys
            165                 170                 175 tta ctg gca ggt tgc cag gcg att acc ctt cct tta gat gta gcg caa      576
Leu Leu Ala Gly Cys Gln Ala Ile Thr Leu Pro Leu Asp Val Ala Gln
        180                 185                 190 caa atg ctc aat acg cct gcg gta gag tcg gca ata gag aag ttt gag      624
Gln Met Leu Asn Thr Pro Ala Val Glu Ser Ala Ile Glu Lys Phe Glu
    195                 200                 205 caa gac tgg aaa aac gct ttt ggt aat ctg aac ctg tag                  663
Gln Asp Trp Lys Asn Ala Phe Gly Asn Leu Asn Leu
210                 215                 220
```

<210> SEQ ID NO 20
<211> LENGTH: 220
<212> TYPE: PRT
<213> ORGANISM: Salmonella enterica

<400> SEQUENCE: 20

```
Met Glu Leu Tyr Leu Asp Thr Ala Asn Val Ala Glu Val Glu Arg Leu
1               5                   10                  15

Ala Arg Ile Phe Pro Ile Ala Gly Val Thr Thr Asn Pro Ser Ile Val
            20                  25                  30

Ala Ala Ser Lys Glu Ser Ile Trp Asp Val Leu Pro Arg Leu Gln Asn
        35                  40                  45

Ala Ile Gly Glu Glu Gly Thr Leu Phe Ala Gln Thr Met Ser Arg Asp
    50                  55                  60

Ala Lys Gly Met Val Glu Glu Ala Lys Arg Leu Asn Asn Ala Ile Pro
65                  70                  75                  80

Gly Ile Val Val Lys Ile Pro Val Thr Ala Glu Gly Leu Ala Ala Ile
                85                  90                  95

Lys Leu Leu Lys Lys Glu Gly Ile Val Thr Leu Gly Thr Ala Val Tyr
            100                 105                 110

Ser Ala Ser Gln Gly Leu Leu Ala Ala Leu Ala Gly Ala Lys Tyr Val
        115                 120                 125

Ala Pro Tyr Val Asn Arg Val Asp Ala Gln Gly Gly Asp Gly Ile Arg
    130                 135                 140

Met Val Gln Glu Leu Gln Thr Leu Leu Glu His His Ala Pro Asp Ser
145                 150                 155                 160

Met Val Leu Ala Ala Ser Phe Lys Thr Pro Arg Gln Ala Leu Asp Cys
                165                 170                 175

Leu Leu Ala Gly Cys Gln Ala Ile Thr Leu Pro Leu Asp Val Ala Gln
            180                 185                 190

Gln Met Leu Asn Thr Pro Ala Val Glu Ser Ala Ile Glu Lys Phe Glu
        195                 200                 205

Gln Asp Trp Lys Asn Ala Phe Gly Asn Leu Asn Leu
    210                 215                 220
```

<210> SEQ ID NO 21
<211> LENGTH: 1992
<212> TYPE: DNA
<213> ORGANISM: Pichia pastoris
<220> FEATURE:
<221> NAME/KEY: CDS
<222> LOCATION: (1)..(1992)

<400> SEQUENCE: 21

-continued

| | |
|---|---|
| atg gct atc ccc gaa gag ttt gat atc cta gtt cta ggt ggt gga tcc<br>Met Ala Ile Pro Glu Glu Phe Asp Ile Leu Val Leu Gly Gly Gly Ser<br>1               5                   10                  15 | 48 |
| agt gga tcc tgt att gcc gga aga ttg gca aac ttg gac cac tcc ttg<br>Ser Gly Ser Cys Ile Ala Gly Arg Leu Ala Asn Leu Asp His Ser Leu<br>            20                  25                  30 | 96 |
| aaa gtt ggt ctt atc gaa gca ggt gag aac aac ctc aac aac cca tgg<br>Lys Val Gly Leu Ile Glu Ala Gly Glu Asn Asn Leu Asn Asn Pro Trp<br>        35                  40                  45 | 144 |
| gtc tac ctt cca ggt att tac cca aga aac atg aag ttg gac tcc aag<br>Val Tyr Leu Pro Gly Ile Tyr Pro Arg Asn Met Lys Leu Asp Ser Lys<br>    50                  55                  60 | 192 |
| act gct tcc ttc tac act tct aac cca tct cct cac ttg aat ggt aga<br>Thr Ala Ser Phe Tyr Thr Ser Asn Pro Ser Pro His Leu Asn Gly Arg<br>65                  70                  75                  80 | 240 |
| aga gcc att gtt cca tgt gct aac gtc ttg ggt ggt ggt tct tct atc<br>Arg Ala Ile Val Pro Cys Ala Asn Val Leu Gly Gly Gly Ser Ser Ile<br>                85                  90                  95 | 288 |
| aac ttc atg atg tac acc aga ggt tct gct tct gat tac gat gac ttc<br>Asn Phe Met Met Tyr Thr Arg Gly Ser Ala Ser Asp Tyr Asp Asp Phe<br>            100                 105                 110 | 336 |
| caa gcc gag ggc tgg aaa acc aag gac ttg ctt cca ttg atg aaa aag<br>Gln Ala Glu Gly Trp Lys Thr Lys Asp Leu Leu Pro Leu Met Lys Lys<br>        115                 120                 125 | 384 |
| act gag acc tac caa aga gct tgc aac aac cct gac att cac ggt ttc<br>Thr Glu Thr Tyr Gln Arg Ala Cys Asn Asn Pro Asp Ile His Gly Phe<br>    130                 135                 140 | 432 |
| gaa ggt cca atc aag gtt tct ttc ggt aac tac acc tac cca gtt tgc<br>Glu Gly Pro Ile Lys Val Ser Phe Gly Asn Tyr Thr Tyr Pro Val Cys<br>145                 150                 155                 160 | 480 |
| cag gac ttc ttg agg gct tct gag tcc caa ggt att cca tac gtt gac<br>Gln Asp Phe Leu Arg Ala Ser Glu Ser Gln Gly Ile Pro Tyr Val Asp<br>                165                 170                 175 | 528 |
| gac ttg gaa gac ttg gtt act gct cac ggt gct gaa cac tgg ttg aag<br>Asp Leu Glu Asp Leu Val Thr Ala His Gly Ala Glu His Trp Leu Lys<br>            180                 185                 190 | 576 |
| tgg atc aac aga gac act ggt cgt cgt tcc gac tct gct cat gca ttt<br>Trp Ile Asn Arg Asp Thr Gly Arg Arg Ser Asp Ser Ala His Ala Phe<br>        195                 200                 205 | 624 |
| gtc cac tct act atg aga aac cac gac aac ttg tac ttg atc tgt aac<br>Val His Ser Thr Met Arg Asn His Asp Asn Leu Tyr Leu Ile Cys Asn<br>    210                 215                 220 | 672 |
| acg aag gtc gac aaa att att gtc gaa gac gga aga gct gct gct gtt<br>Thr Lys Val Asp Lys Ile Ile Val Glu Asp Gly Arg Ala Ala Ala Val<br>225                 230                 235                 240 | 720 |
| aga acc gtt cca agc aag cct ttg aac cca aag aag cca agt cac aag<br>Arg Thr Val Pro Ser Lys Pro Leu Asn Pro Lys Lys Pro Ser His Lys<br>                245                 250                 255 | 768 |
| atc tac cgt gct aga aag caa atc gtt ttg tct tgt ggt acc atc tcc<br>Ile Tyr Arg Ala Arg Lys Gln Ile Val Leu Ser Cys Gly Thr Ile Ser<br>            260                 265                 270 | 816 |
| tct cca ttg gtt ttg caa aga tcc ggt ttt ggt gac cca atc aag ttg<br>Ser Pro Leu Val Leu Gln Arg Ser Gly Phe Gly Asp Pro Ile Lys Leu<br>        275                 280                 285 | 864 |
| aga gcc gct ggt gtt aag cct ttg gtc aac ttg cca ggt gtc gga aga<br>Arg Ala Ala Gly Val Lys Pro Leu Val Asn Leu Pro Gly Val Gly Arg<br>    290                 295                 300 | 912 |
| aac ttc caa gac cac tac tgt ttc ttc agt cct tac aga atc aag cct<br>Asn Phe Gln Asp His Tyr Cys Phe Phe Ser Pro Tyr Arg Ile Lys Pro<br>305                 310                 315                 320 | 960 |

```
cag tac gag tct ttc gat gac ttc gtc cgt ggt gat gct gag att caa    1008
Gln Tyr Glu Ser Phe Asp Asp Phe Val Arg Gly Asp Ala Glu Ile Gln
            325                 330                 335 aag aga gtc ttt gac caa tgg tac gcc aat ggt act ggt cct ctt gcc    1056
Lys Arg Val Phe Asp Gln Trp Tyr Ala Asn Gly Thr Gly Pro Leu Ala
            340                 345                 350 act aac ggt atc gaa gct ggt gtc aag atc aga cca aca cca gaa gaa    1104
Thr Asn Gly Ile Glu Ala Gly Val Lys Ile Arg Pro Thr Pro Glu Glu
            355                 360                 365 ctc tct caa atg gac gaa tcc ttc cag gag ggt tac aga gaa tac ttc    1152
Leu Ser Gln Met Asp Glu Ser Phe Gln Glu Gly Tyr Arg Glu Tyr Phe
    370                 375                 380 gaa gac aag cca gac aag cca gtt atg cac tac tcc atc att gct ggt    1200
Glu Asp Lys Pro Asp Lys Pro Val Met His Tyr Ser Ile Ile Ala Gly
385                 390                 395                 400 ttc ttc ggt gac cac acc aag att cct cct gga aag tac atg act atg    1248
Phe Phe Gly Asp His Thr Lys Ile Pro Pro Gly Lys Tyr Met Thr Met
                405                 410                 415 ttc cac ttc ttg gaa tac cca ttc tcc aga ggt tcc att cac att acc    1296
Phe His Phe Leu Glu Tyr Pro Phe Ser Arg Gly Ser Ile His Ile Thr
            420                 425                 430 tcc cca gac cca tac gca gct cca gac ttc gac cca ggt ttc atg aac    1344
Ser Pro Asp Pro Tyr Ala Ala Pro Asp Phe Asp Pro Gly Phe Met Asn
            435                 440                 445 gat gaa aga gac atg gct cct atg gtt tgg gct tac aag aag tct aga    1392
Asp Glu Arg Asp Met Ala Pro Met Val Trp Ala Tyr Lys Lys Ser Arg
    450                 455                 460 gaa acc gct aga aga atg gac cac ttt gcc ggt gag gtc act tct cac    1440
Glu Thr Ala Arg Arg Met Asp His Phe Ala Gly Glu Val Thr Ser His
465                 470                 475                 480 cac cct ctg ttc cca tac tca tcc gag gcc aga gcc ttg gaa atg gat    1488
His Pro Leu Phe Pro Tyr Ser Ser Glu Ala Arg Ala Leu Glu Met Asp
                485                 490                 495 ttg gag acc tct aat gcc tac ggt gga cct ttg aac ttg tct gct ggt    1536
Leu Glu Thr Ser Asn Ala Tyr Gly Gly Pro Leu Asn Leu Ser Ala Gly
            500                 505                 510 ctt gct cac ggt tct tgg act caa cct ttg aag aag cca act gca aag    1584
Leu Ala His Gly Ser Trp Thr Gln Pro Leu Lys Lys Pro Thr Ala Lys
            515                 520                 525 aac gaa ggc cac gtt act tcg aac cag gtc gag ctt cat cca gac atc    1632
Asn Glu Gly His Val Thr Ser Asn Gln Val Glu Leu His Pro Asp Ile
    530                 535                 540 gag tac gat gag gag gat gac aag gcc att gag aac tac att cgt gag    1680
Glu Tyr Asp Glu Glu Asp Asp Lys Ala Ile Glu Asn Tyr Ile Arg Glu
545                 550                 555                 560 cac act gag acc aca tgg cac tgt ctg gga acc tgt tcc atc ggt cca    1728
His Thr Glu Thr Thr Trp His Cys Leu Gly Thr Cys Ser Ile Gly Pro
                565                 570                 575 aga gaa ggt tcc aag atc gtc aaa tgg ggt ggt gtt ttg gac cac aga    1776
Arg Glu Gly Ser Lys Ile Val Lys Trp Gly Gly Val Leu Asp His Arg
            580                 585                 590 tcc aac gtt tac gga gtc aag ggc ttg aag gtt ggt gac ttg tcc gtg    1824
Ser Asn Val Tyr Gly Val Lys Gly Leu Lys Val Gly Asp Leu Ser Val
            595                 600                 605 tgc cca gac aat gtt ggt tgt aac acc tac acc acc gct ctt ttg atc    1872
Cys Pro Asp Asn Val Gly Cys Asn Thr Tyr Thr Thr Ala Leu Leu Ile
    610                 615                 620 ggt gaa aag act gcc act ttg gtt gga gaa gat tta gga tac tct ggt    1920
Gly Glu Lys Thr Ala Thr Leu Val Gly Glu Asp Leu Gly Tyr Ser Gly
```

```
                    625                 630                 635                 640
gag gcc tta gac atg act gtt cct cag ttc aag ttg ggc act tac gag    1968
Glu Ala Leu Asp Met Thr Val Pro Gln Phe Lys Leu Gly Thr Tyr Glu
                645                 650                 655 aag acc ggt ctt gct aga ttc taa                                    1992
Lys Thr Gly Leu Ala Arg Phe
                660
```

<210> SEQ ID NO 22
<211> LENGTH: 663
<212> TYPE: PRT
<213> ORGANISM: Pichia pastoris

<400> SEQUENCE: 22

```
Met Ala Ile Pro Glu Glu Phe Asp Ile Leu Val Leu Gly Gly Gly Ser
1               5                   10                  15

Ser Gly Ser Cys Ile Ala Gly Arg Leu Ala Asn Leu Asp His Ser Leu
            20                  25                  30

Lys Val Gly Leu Ile Glu Ala Gly Glu Asn Asn Leu Asn Asn Pro Trp
        35                  40                  45

Val Tyr Leu Pro Gly Ile Tyr Pro Arg Asn Met Lys Leu Asp Ser Lys
    50                  55                  60

Thr Ala Ser Phe Tyr Thr Ser Asn Pro Ser Pro His Leu Asn Gly Arg
65                  70                  75                  80

Arg Ala Ile Val Pro Cys Ala Asn Val Leu Gly Gly Ser Ser Ile
                85                  90                  95

Asn Phe Met Met Tyr Thr Arg Gly Ser Ala Ser Asp Tyr Asp Asp Phe
            100                 105                 110

Gln Ala Glu Gly Trp Lys Thr Lys Asp Leu Leu Pro Leu Met Lys Lys
        115                 120                 125

Thr Glu Thr Tyr Gln Arg Ala Cys Asn Asn Pro Asp Ile His Gly Phe
    130                 135                 140

Glu Gly Pro Ile Lys Val Ser Phe Gly Asn Tyr Thr Tyr Pro Val Cys
145                 150                 155                 160

Gln Asp Phe Leu Arg Ala Ser Glu Ser Gln Gly Ile Pro Tyr Val Asp
                165                 170                 175

Asp Leu Glu Asp Leu Val Thr Ala His Gly Ala Glu His Trp Leu Lys
            180                 185                 190

Trp Ile Asn Arg Asp Thr Gly Arg Arg Ser Asp Ser Ala His Ala Phe
        195                 200                 205

Val His Ser Thr Met Arg Asn His Asp Asn Leu Tyr Leu Ile Cys Asn
    210                 215                 220

Thr Lys Val Asp Lys Ile Ile Val Glu Asp Gly Arg Ala Ala Ala Val
225                 230                 235                 240

Arg Thr Val Pro Ser Lys Pro Leu Asn Pro Lys Lys Pro Ser His Lys
                245                 250                 255

Ile Tyr Arg Ala Arg Lys Gln Ile Val Leu Ser Cys Gly Thr Ile Ser
            260                 265                 270

Ser Pro Leu Val Leu Gln Arg Ser Gly Phe Gly Asp Pro Ile Lys Leu
        275                 280                 285

Arg Ala Ala Gly Val Lys Pro Leu Val Asn Leu Pro Gly Val Gly Arg
    290                 295                 300

Asn Phe Gln Asp His Tyr Cys Phe Phe Ser Pro Tyr Arg Ile Lys Pro
305                 310                 315                 320

Gln Tyr Glu Ser Phe Asp Asp Phe Val Arg Gly Asp Ala Glu Ile Gln
```

```
                    325                 330                 335
Lys Arg Val Phe Asp Gln Trp Tyr Ala Asn Gly Thr Gly Pro Leu Ala
            340                 345                 350
Thr Asn Gly Ile Glu Ala Gly Val Lys Ile Arg Pro Thr Pro Glu Glu
        355                 360                 365
Leu Ser Gln Met Asp Glu Ser Phe Gln Glu Gly Tyr Arg Glu Tyr Phe
    370                 375                 380
Glu Asp Lys Pro Asp Lys Pro Val Met His Tyr Ser Ile Ile Ala Gly
385                 390                 395                 400
Phe Phe Gly Asp His Thr Lys Ile Pro Pro Gly Lys Tyr Met Thr Met
                405                 410                 415
Phe His Phe Leu Glu Tyr Pro Phe Ser Arg Gly Ser Ile His Ile Thr
            420                 425                 430
Ser Pro Asp Pro Tyr Ala Ala Pro Asp Phe Asp Pro Gly Phe Met Asn
        435                 440                 445
Asp Glu Arg Asp Met Ala Pro Met Val Trp Ala Tyr Lys Lys Ser Arg
    450                 455                 460
Glu Thr Ala Arg Arg Met Asp His Phe Ala Gly Glu Val Thr Ser His
465                 470                 475                 480
His Pro Leu Phe Pro Tyr Ser Ser Glu Ala Arg Ala Leu Glu Met Asp
                485                 490                 495
Leu Glu Thr Ser Asn Ala Tyr Gly Gly Pro Leu Asn Leu Ser Ala Gly
            500                 505                 510
Leu Ala His Gly Ser Trp Thr Gln Pro Leu Lys Lys Pro Thr Ala Lys
        515                 520                 525
Asn Glu Gly His Val Thr Ser Asn Gln Val Glu Leu His Pro Asp Ile
    530                 535                 540
Glu Tyr Asp Glu Glu Asp Asp Lys Ala Ile Glu Asn Tyr Ile Arg Glu
545                 550                 555                 560
His Thr Glu Thr Thr Trp His Cys Leu Gly Thr Cys Ser Ile Gly Pro
                565                 570                 575
Arg Glu Gly Ser Lys Ile Val Lys Trp Gly Gly Val Leu Asp His Arg
            580                 585                 590
Ser Asn Val Tyr Gly Val Lys Gly Leu Lys Val Gly Asp Leu Ser Val
        595                 600                 605
Cys Pro Asp Asn Val Gly Cys Asn Thr Tyr Thr Thr Ala Leu Leu Ile
    610                 615                 620
Gly Glu Lys Thr Ala Thr Leu Val Gly Glu Asp Leu Gly Tyr Ser Gly
625                 630                 635                 640
Glu Ala Leu Asp Met Thr Val Pro Gln Phe Lys Leu Gly Thr Tyr Glu
                645                 650                 655
Lys Thr Gly Leu Ala Arg Phe
            660

<210> SEQ ID NO 23
<211> LENGTH: 1185
<212> TYPE: DNA
<213> ORGANISM: Escherichia coli
<220> FEATURE:
<221> NAME/KEY: CDS
<222> LOCATION: (1)..(1185)

<400> SEQUENCE: 23 atg aaa aat tgt gtc atc gtc agt gcg gta cgt act gct atc ggt agt    48
Met Lys Asn Cys Val Ile Val Ser Ala Val Arg Thr Ala Ile Gly Ser
1               5                   10                  15
```

| | | | | | | | | | | | | | | | | |
|---|---|---|---|---|---|---|---|---|---|---|---|---|---|---|---|---|
| ttt | aac | ggt | tca | ctc | gct | tcc | acc | agc | gcc | atc | gac | ctg | ggg | gcg | aca | 96 |
| Phe | Asn | Gly | Ser | Leu | Ala | Ser | Thr | Ser | Ala | Ile | Asp | Leu | Gly | Ala | Thr | |
| | | | 20 | | | | 25 | | | | | 30 | | | | |
| gta | att | aaa | gcc | gcc | att | gaa | cgt | gca | aaa | atc | gat | tca | caa | cac | gtt | 144 |
| Val | Ile | Lys | Ala | Ala | Ile | Glu | Arg | Ala | Lys | Ile | Asp | Ser | Gln | His | Val | |
| | | 35 | | | | 40 | | | | | 45 | | | | | |
| gat | gaa | gtg | att | atg | ggt | aac | gtg | tta | caa | gcc | ggg | ctg | ggg | caa | aat | 192 |
| Asp | Glu | Val | Ile | Met | Gly | Asn | Val | Leu | Gln | Ala | Gly | Leu | Gly | Gln | Asn | |
| | 50 | | | | | 55 | | | | | 60 | | | | | |
| ccg | gcg | cgt | cag | gca | ctg | tta | aaa | agc | ggg | ctg | gca | gaa | acg | gtg | tgc | 240 |
| Pro | Ala | Arg | Gln | Ala | Leu | Leu | Lys | Ser | Gly | Leu | Ala | Glu | Thr | Val | Cys | |
| 65 | | | | | 70 | | | | | 75 | | | | | 80 | |
| gga | ttc | acg | gtc | aat | aaa | gta | tgt | ggt | tcg | ggt | ctt | aaa | agt | gtg | gcg | 288 |
| Gly | Phe | Thr | Val | Asn | Lys | Val | Cys | Gly | Ser | Gly | Leu | Lys | Ser | Val | Ala | |
| | | | | 85 | | | | | 90 | | | | | 95 | | |
| ctt | gcc | gcc | cag | gcc | att | cag | gca | ggt | cag | gcg | cag | agc | att | gtg | gcg | 336 |
| Leu | Ala | Ala | Gln | Ala | Ile | Gln | Ala | Gly | Gln | Ala | Gln | Ser | Ile | Val | Ala | |
| | | | | 100 | | | | | 105 | | | | | 110 | | |
| ggg | ggt | atg | gaa | aat | atg | agt | tta | gcc | ccc | tac | tta | ctc | gat | gca | aaa | 384 |
| Gly | Gly | Met | Glu | Asn | Met | Ser | Leu | Ala | Pro | Tyr | Leu | Leu | Asp | Ala | Lys | |
| | | | 115 | | | | | 120 | | | | | 125 | | | |
| gca | cgc | tct | ggt | tat | cgt | ctt | gga | gac | gga | cag | gtt | tat | gac | gta | atc | 432 |
| Ala | Arg | Ser | Gly | Tyr | Arg | Leu | Gly | Asp | Gly | Gln | Val | Tyr | Asp | Val | Ile | |
| | 130 | | | | | 135 | | | | | 140 | | | | | |
| ctg | cgc | gat | ggc | ctg | atg | tgc | gcc | acc | cat | ggt | tat | cat | atg | ggg | att | 480 |
| Leu | Arg | Asp | Gly | Leu | Met | Cys | Ala | Thr | His | Gly | Tyr | His | Met | Gly | Ile | |
| 145 | | | | | 150 | | | | | 155 | | | | | 160 | |
| acc | gcc | gaa | aac | gtg | gct | aaa | gag | tac | gga | att | acc | cgt | gaa | atg | cag | 528 |
| Thr | Ala | Glu | Asn | Val | Ala | Lys | Glu | Tyr | Gly | Ile | Thr | Arg | Glu | Met | Gln | |
| | | | | 165 | | | | | 170 | | | | | 175 | | |
| gat | gaa | ctg | gcg | cta | cat | tca | cag | cgt | aaa | gcg | gca | gcc | gca | att | gag | 576 |
| Asp | Glu | Leu | Ala | Leu | His | Ser | Gln | Arg | Lys | Ala | Ala | Ala | Ala | Ile | Glu | |
| | | | 180 | | | | | 185 | | | | | 190 | | | |
| tcc | ggt | gct | ttt | aca | gcc | gaa | atc | gtc | ccg | gta | aat | gtt | gtc | act | cga | 624 |
| Ser | Gly | Ala | Phe | Thr | Ala | Glu | Ile | Val | Pro | Val | Asn | Val | Val | Thr | Arg | |
| | | 195 | | | | | 200 | | | | | 205 | | | | |
| aag | aaa | acc | ttc | gtc | ttc | agt | caa | gac | gaa | ttc | ccg | aaa | gcg | aat | tca | 672 |
| Lys | Lys | Thr | Phe | Val | Phe | Ser | Gln | Asp | Glu | Phe | Pro | Lys | Ala | Asn | Ser | |
| 210 | | | | | 215 | | | | | 220 | | | | | | |
| acg | gct | gaa | gcg | tta | ggt | gca | ttg | cgc | ccg | gcc | ttc | gat | aaa | gca | gga | 720 |
| Thr | Ala | Glu | Ala | Leu | Gly | Ala | Leu | Arg | Pro | Ala | Phe | Asp | Lys | Ala | Gly | |
| 225 | | | | | 230 | | | | | 235 | | | | | 240 | |
| aca | gtc | acc | gct | ggg | aac | gcg | tct | ggt | att | aac | gac | ggt | gct | gcc | gct | 768 |
| Thr | Val | Thr | Ala | Gly | Asn | Ala | Ser | Gly | Ile | Asn | Asp | Gly | Ala | Ala | Ala | |
| | | | | 245 | | | | | 250 | | | | | 255 | | |
| ctg | gtg | att | atg | gaa | gaa | tct | gcg | gcg | ctg | gca | gca | ggc | ctt | acc | ccc | 816 |
| Leu | Val | Ile | Met | Glu | Glu | Ser | Ala | Ala | Leu | Ala | Ala | Gly | Leu | Thr | Pro | |
| | | | 260 | | | | | 265 | | | | | 270 | | | |
| ctg | gct | cgc | att | aaa | agt | tat | gcc | agc | ggt | ggc | gtg | ccc | ccc | gca | ttg | 864 |
| Leu | Ala | Arg | Ile | Lys | Ser | Tyr | Ala | Ser | Gly | Gly | Val | Pro | Pro | Ala | Leu | |
| | | 275 | | | | | 280 | | | | | 285 | | | | |
| atg | ggt | atg | ggg | cca | gta | cct | gcc | acg | caa | aaa | gcg | tta | caa | ctg | gcg | 912 |
| Met | Gly | Met | Gly | Pro | Val | Pro | Ala | Thr | Gln | Lys | Ala | Leu | Gln | Leu | Ala | |
| | | | 290 | | | | | 295 | | | | | 300 | | | |
| ggg | ctg | caa | ctg | gcg | gat | att | gat | ctc | att | gag | gct | aat | gaa | gca | ttt | 960 |
| Gly | Leu | Gln | Leu | Ala | Asp | Ile | Asp | Leu | Ile | Glu | Ala | Asn | Glu | Ala | Phe | |
| 305 | | | | | 310 | | | | | 315 | | | | | 320 | |
| gct | gca | cag | ttc | ctt | gcc | gtt | ggg | aaa | aac | ctg | ggc | ttt | gat | tct | gag | 1008 |
| Ala | Ala | Gln | Phe | Leu | Ala | Val | Gly | Lys | Asn | Leu | Gly | Phe | Asp | Ser | Glu | |

```
                        325                     330                     335
aaa gtg aat gtc aac ggc ggg gcc atc gcg ctc ggg cat cct atc ggt     1056
Lys Val Asn Val Asn Gly Gly Ala Ile Ala Leu Gly His Pro Ile Gly
            340                     345                     350 gcc agt ggt gct cgt att ctg gtc aca cta tta cat gcc atg cag gca     1104
Ala Ser Gly Ala Arg Ile Leu Val Thr Leu Leu His Ala Met Gln Ala
        355                     360                     365 cgc gat aaa acg ctg ggg ctg gca aca ctg tgc att ggc ggc ggt cag     1152
Arg Asp Lys Thr Leu Gly Leu Ala Thr Leu Cys Ile Gly Gly Gly Gln
    370                     375                     380 gga att gcg atg gtg att gaa cgg ttg aat taa                         1185
Gly Ile Ala Met Val Ile Glu Arg Leu Asn
385                     390

<210> SEQ ID NO 24
<211> LENGTH: 394
<212> TYPE: PRT
<213> ORGANISM: Escherichia coli

<400> SEQUENCE: 24

Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285
```

```
Met Gly Met Gly Pro Val Pro Ala Thr Gln Lys Ala Leu Gln Leu Ala
        290                 295                 300
Gly Leu Gln Leu Ala Asp Ile Asp Leu Ile Glu Ala Asn Glu Ala Phe
305                 310                 315                 320
Ala Ala Gln Phe Leu Ala Val Gly Lys Asn Leu Gly Phe Asp Ser Glu
                325                 330                 335
Lys Val Asn Val Asn Gly Gly Ala Ile Ala Leu Gly His Pro Ile Gly
            340                 345                 350
Ala Ser Gly Ala Arg Ile Leu Val Thr Leu Leu His Ala Met Gln Ala
        355                 360                 365
Arg Asp Lys Thr Leu Gly Leu Ala Thr Leu Cys Ile Gly Gly Gly Gln
    370                 375                 380
Gly Ile Ala Met Val Ile Glu Arg Leu Asn
385                 390

<210> SEQ ID NO 25
<211> LENGTH: 1179
<212> TYPE: DNA
<213> ORGANISM: Clostridium acetobutylicum
<220> FEATURE:
<221> NAME/KEY: CDS
<222> LOCATION: (1)..(1179)

<400> SEQUENCE: 25 atg aaa gaa gtt gta ata gct agt gca gta aga aca gcg att gga tct     48
Met Lys Glu Val Val Ile Ala Ser Ala Val Arg Thr Ala Ile Gly Ser
1               5                   10                  15 tat gga aag tct ctt aag gat gta cca gca gta gat tta gga gct aca     96
Tyr Gly Lys Ser Leu Lys Asp Val Pro Ala Val Asp Leu Gly Ala Thr
                20                  25                  30 gct ata aag gaa gca gtt aaa aaa gca gga ata aaa cca gag gat gtt    144
Ala Ile Lys Glu Ala Val Lys Lys Ala Gly Ile Lys Pro Glu Asp Val
            35                  40                  45 aat gaa gtc att tta gga aat gtt ctt caa gca ggt tta gga cag aat    192
Asn Glu Val Ile Leu Gly Asn Val Leu Gln Ala Gly Leu Gly Gln Asn
        50                  55                  60 cca gca aga cag gca tct ttt aaa gca gga tta cca gtt gaa att cca    240
Pro Ala Arg Gln Ala Ser Phe Lys Ala Gly Leu Pro Val Glu Ile Pro
65                  70                  75                  80 gct atg act att aat aag gtt tgt ggt tca gga ctt aga aca gtt agc    288
Ala Met Thr Ile Asn Lys Val Cys Gly Ser Gly Leu Arg Thr Val Ser
                85                  90                  95 tta gca gca caa att ata aaa gca gga gat gct gac gta ata ata gca    336
Leu Ala Ala Gln Ile Ile Lys Ala Gly Asp Ala Asp Val Ile Ile Ala
                100                 105                 110 ggt ggt atg gaa aat atg tct aga gct cct tac tta gcg aat aac gct    384
Gly Gly Met Glu Asn Met Ser Arg Ala Pro Tyr Leu Ala Asn Asn Ala
            115                 120                 125 aga tgg gga tat aga atg gga aac gct aaa ttt gtt gat gaa atg atc    432
Arg Trp Gly Tyr Arg Met Gly Asn Ala Lys Phe Val Asp Glu Met Ile
        130                 135                 140 act gac gga ttg tgg gat gca ttt aat gat tac cac atg gga ata aca    480
Thr Asp Gly Leu Trp Asp Ala Phe Asn Asp Tyr His Met Gly Ile Thr
145                 150                 155                 160 gca gaa aac ata gct gag aga tgg aac att tca aga gaa gaa caa gat    528
Ala Glu Asn Ile Ala Glu Arg Trp Asn Ile Ser Arg Glu Glu Gln Asp
                165                 170                 175 gag ttt gct ctt gca tca caa aaa aaa gct gaa gaa gct ata aaa tca    576
Glu Phe Ala Leu Ala Ser Gln Lys Lys Ala Glu Glu Ala Ile Lys Ser
```

```
                       180                185                190
ggt caa ttt aaa gat gaa ata gtt cct gta gta att aaa ggc aga aag      624
Gly Gln Phe Lys Asp Glu Ile Val Pro Val Val Ile Lys Gly Arg Lys
            195                 200                 205 gga gaa act gta gtt gat aca gat gag cac cct aga ttt gga tca act      672
Gly Glu Thr Val Val Asp Thr Asp Glu His Pro Arg Phe Gly Ser Thr
210                 215                 220 ata gaa gga ctt gca aaa tta aaa cct gcc ttc aaa aaa gat gga aca      720
Ile Glu Gly Leu Ala Lys Leu Lys Pro Ala Phe Lys Lys Asp Gly Thr
225                 230                 235                 240 gtt aca gct ggt aat gca tca gga tta aat gac tgt gca gca gta ctt      768
Val Thr Ala Gly Asn Ala Ser Gly Leu Asn Asp Cys Ala Ala Val Leu
            245                 250                 255 gta atc atg agt gca gaa aaa gct aaa gag ctt gga gta aaa cca ctt      816
Val Ile Met Ser Ala Glu Lys Ala Lys Glu Leu Gly Val Lys Pro Leu
        260                 265                 270 gct aag ata gtt tct tat ggt tca gca gga gtt gac cca gca ata atg      864
Ala Lys Ile Val Ser Tyr Gly Ser Ala Gly Val Asp Pro Ala Ile Met
    275                 280                 285 gga tat gga cct ttc tat gca aca aaa gca gct att gaa aaa gca ggt      912
Gly Tyr Gly Pro Phe Tyr Ala Thr Lys Ala Ala Ile Glu Lys Ala Gly
290                 295                 300 tgg aca gtt gat gaa tta gat tta ata gaa tca aat gaa gct ttt gca      960
Trp Thr Val Asp Glu Leu Asp Leu Ile Glu Ser Asn Glu Ala Phe Ala
305                 310                 315                 320 gct caa agt tta gca gta gca aaa gat tta aaa ttt gat atg aat aaa     1008
Ala Gln Ser Leu Ala Val Ala Lys Asp Leu Lys Phe Asp Met Asn Lys
            325                 330                 335 gta aat gta aat gga gga gct att gcc ctt ggt cat cca att gga gca     1056
Val Asn Val Asn Gly Gly Ala Ile Ala Leu Gly His Pro Ile Gly Ala
        340                 345                 350 tca ggt gca aga ata ctc gtt act ctt gta cac gca atg caa aaa aga     1104
Ser Gly Ala Arg Ile Leu Val Thr Leu Val His Ala Met Gln Lys Arg
    355                 360                 365 gat gca aaa aaa ggc tta gca act tta tgt ata ggt ggc gga caa gga     1152
Asp Ala Lys Lys Gly Leu Ala Thr Leu Cys Ile Gly Gly Gly Gln Gly
370                 375                 380 aca gca ata ttg cta gaa aag tgc tag                                 1179
Thr Ala Ile Leu Leu Glu Lys Cys
385                 390

<210> SEQ ID NO 26
<211> LENGTH: 392
<212> TYPE: PRT
<213> ORGANISM: Clostridium acetobutylicum

<400> SEQUENCE: 26

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95
```

Leu Ala Ala Gln Ile Ile Lys Ala Gly Asp Ala Asp Val Ile Ile Ala
                100                 105                 110

Gly Gly Met Glu Asn Met Ser Arg Ala Pro Tyr Leu Ala Asn Asn Ala
            115                 120                 125

Arg Trp Gly Tyr Arg Met Gly Asn Ala Lys Phe Val Asp Glu Met Ile
        130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
        210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 27
<211> LENGTH: 849
<212> TYPE: DNA
<213> ORGANISM: Clostridium acetobutylicum
<220> FEATURE:
<221> NAME/KEY: CDS
<222> LOCATION: (1)..(849)

<400> SEQUENCE: 27 atg aaa aag gta tgt gtt ata ggt gca ggt act atg ggt tca gga att      48
Met Lys Lys Val Cys Val Ile Gly Ala Gly Thr Met Gly Ser Gly Ile
1               5                   10                  15 gct cag gca ttt gca gct aaa gga ttt gaa gta gta tta aga gat att      96
Ala Gln Ala Phe Ala Ala Lys Gly Phe Glu Val Val Leu Arg Asp Ile
                20                  25                  30 aaa gat gaa ttt gtt gat aga gga tta gat ttt atc aat aaa aat ctt     144
Lys Asp Glu Phe Val Asp Arg Gly Leu Asp Phe Ile Asn Lys Asn Leu

```
                 35                   40                   45
tct aaa tta gtt aaa aaa gga aag ata gaa gaa gct act aaa gtt gaa       192
Ser Lys Leu Val Lys Lys Gly Lys Ile Glu Glu Ala Thr Lys Val Glu
 50                   55                   60 atc tta act aga att tcc gga aca gtt gac ctt aat atg gca gct gat       240
Ile Leu Thr Arg Ile Ser Gly Thr Val Asp Leu Asn Met Ala Ala Asp
 65                   70                   75                   80 tgc gat tta gtt ata gaa gca gct gtt gaa aga atg gat att aaa aag       288
Cys Asp Leu Val Ile Glu Ala Ala Val Glu Arg Met Asp Ile Lys Lys
                      85                   90                   95 cag att ttt gct gac tta gac aat ata tgc aag cca gaa aca att ctt       336
Gln Ile Phe Ala Asp Leu Asp Asn Ile Cys Lys Pro Glu Thr Ile Leu
                100                  105                  110 gca tca aat aca tca tca ctt tca ata aca gaa gtg gca tca gca act       384
Ala Ser Asn Thr Ser Ser Leu Ser Ile Thr Glu Val Ala Ser Ala Thr
            115                  120                  125 aaa aga cct gat aag gtt ata ggt atg cat ttc ttt aat cca gct cct       432
Lys Arg Pro Asp Lys Val Ile Gly Met His Phe Phe Asn Pro Ala Pro
130                  135                  140 gtt atg aag ctt gta gag gta ata aga gga ata gct aca tca caa gaa       480
Val Met Lys Leu Val Glu Val Ile Arg Gly Ile Ala Thr Ser Gln Glu
145                  150                  155                  160 act ttt gat gca gtt aaa gag aca tct ata gca ata gga aaa gat cct       528
Thr Phe Asp Ala Val Lys Glu Thr Ser Ile Ala Ile Gly Lys Asp Pro
                165                  170                  175 gta gaa gta gca gaa gca cca gga ttt gtt gta aat aga ata tta ata       576
Val Glu Val Ala Glu Ala Pro Gly Phe Val Val Asn Arg Ile Leu Ile
                180                  185                  190 cca atg att aat gaa gca gtt ggt ata tta gca gaa gga ata gct tca       624
Pro Met Ile Asn Glu Ala Val Gly Ile Leu Ala Glu Gly Ile Ala Ser
            195                  200                  205 gta gaa gac ata gat aaa gct atg aaa ctt gga gct aat cac cca atg       672
Val Glu Asp Ile Asp Lys Ala Met Lys Leu Gly Ala Asn His Pro Met
210                  215                  220 gga cca tta gaa tta ggt gat ttt ata ggt ctt gat ata tgt ctt gct       720
Gly Pro Leu Glu Leu Gly Asp Phe Ile Gly Leu Asp Ile Cys Leu Ala
225                  230                  235                  240 ata atg gat gtt tta tac tca gaa act gga gat tct aag tat aga cca       768
Ile Met Asp Val Leu Tyr Ser Glu Thr Gly Asp Ser Lys Tyr Arg Pro
                245                  250                  255 cat aca tta ctt aag aag tat gta aga gca gga tgg ctt gga aga aaa       816
His Thr Leu Leu Lys Lys Tyr Val Arg Ala Gly Trp Leu Gly Arg Lys
                260                  265                  270 tca gga aaa ggt ttc tac gat tat tca aaa taa                          849
Ser Gly Lys Gly Phe Tyr Asp Tyr Ser Lys
            275                  280
```

<210> SEQ ID NO 28
<211> LENGTH: 282
<212> TYPE: PRT
<213> ORGANISM: Clostridium acetobutylicum

<400> SEQUENCE: 28

```
Met Lys Lys Val Cys Val Ile Gly Ala Gly Thr Met Gly Ser Gly Ile
 1               5                  10                  15

Ala Gln Ala Phe Ala Ala Lys Gly Phe Glu Val Val Leu Arg Asp Ile
                20                  25                  30

Lys Asp Glu Phe Val Asp Arg Gly Leu Asp Phe Ile Asn Lys Asn Leu
            35                  40                  45
```

```
Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
 65                  70                  75                  80

Cys Asp Leu Val Ile Glu Ala Ala Val Glu Arg Met Asp Ile Lys Lys
                 85                  90                  95

Gln Ile Phe Ala Asp Leu Asp Asn Ile Cys Lys Pro Glu Thr Ile Leu
                100                 105                 110

Ala Ser Asn Thr Ser Ser Leu Ser Ile Thr Glu Val Ala Ser Ala Thr
            115                 120                 125

Lys Arg Pro Asp Lys Val Ile Gly Met His Phe Phe Asn Pro Ala Pro
        130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
                180                 185                 190

Pro Met Ile Asn Glu Ala Val Gly Ile Leu Ala Glu Gly Ile Ala Ser
            195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280

<210> SEQ ID NO 29
<211> LENGTH: 786
<212> TYPE: DNA
<213> ORGANISM: Clostridium acetobutylicum
<220> FEATURE:
<221> NAME/KEY: CDS
<222> LOCATION: (1)..(786)

<400> SEQUENCE: 29 atg gaa cta aac aat gtc atc ctt gaa aag gaa ggt aaa gtt gct gta    48
Met Glu Leu Asn Asn Val Ile Leu Glu Lys Glu Gly Lys Val Ala Val
 1               5                  10                  15 gtt acc att aac aga cct aaa gca tta aat gcg tta aat agt gat aca    96
Val Thr Ile Asn Arg Pro Lys Ala Leu Asn Ala Leu Asn Ser Asp Thr
                20                  25                  30 cta aaa gaa atg gat tat gtt ata ggt gaa att gaa aat gat agc gaa   144
Leu Lys Glu Met Asp Tyr Val Ile Gly Glu Ile Glu Asn Asp Ser Glu
            35                  40                  45 gta ctt gca gta att tta act gga gca gga gaa aaa tca ttt gta gca   192
Val Leu Ala Val Ile Leu Thr Gly Ala Gly Glu Lys Ser Phe Val Ala
 50                  55                  60 gga gca gat att tct gag atg aag gaa atg aat acc att gaa ggt aga   240
Gly Ala Asp Ile Ser Glu Met Lys Glu Met Asn Thr Ile Glu Gly Arg
 65                  70                  75                  80 aaa ttc ggg ata ctt gga aat aaa gtg ttt aga aga tta gaa ctt ctt   288
Lys Phe Gly Ile Leu Gly Asn Lys Val Phe Arg Arg Leu Glu Leu Leu
                 85                  90                  95
```

```
gaa aag cct gta ata gca gct gtt aat ggt ttt gct tta gga ggc

```
Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260
```

<210> SEQ ID NO 31
<211> LENGTH: 1344
<212> TYPE: DNA
<213> ORGANISM: Streptomyces coelicolor
<220> FEATURE:
<221> NAME/KEY: CDS
<222> LOCATION: (1)..(1344)

<400> SEQUENCE: 31

```
gtg acc gtg aag gac atc ctg gac gcg atc cag tcg ccc gac tcc acg      48
Val Thr Val Lys Asp Ile Leu Asp Ala Ile Gln Ser Pro Asp Ser Thr
1               5                   10                  15 ccg gcc gac atc gcc gca ctg ccg ctc ccc gag tcg tac cgc gcg atc      96
Pro Ala Asp Ile Ala Ala Leu Pro Leu Pro Glu Ser Tyr Arg Ala Ile
                20                  25                  30 acc gtg cac aag gac gag acc gag atg ttc gcg ggc ctc gag acc cgc     144
Thr Val His Lys Asp Glu Thr Glu Met Phe Ala Gly Leu Glu Thr Arg
            35                  40                  45 gac aag gac ccc cgc aag tcg atc cac ctg gac gac gtg ccg gtg ccc     192
Asp Lys Asp Pro Arg Lys Ser Ile His Leu Asp Asp Val Pro Val Pro
50                  55                  60 gag ctg ggc ccc ggc gag gcc ctg gtg gcc gtc atg gcc tcc tcg gtc     240
Glu Leu Gly Pro Gly Glu Ala Leu Val Ala Val Met Ala Ser Ser Val
65                  70                  75                  80 aac tac aac tcg gtg tgg acc tcg atc ttc gag ccg ctg tcc acc ttc     288
Asn Tyr Asn Ser Val Trp Thr Ser Ile Phe Glu Pro Leu Ser Thr Phe
                85                  90                  95 ggg ttc ctg gag cgc tac ggc cgg gtc agc gac ctc gcc aag cgg cac     336
Gly Phe Leu Glu Arg Tyr Gly Arg Val Ser Asp Leu Ala Lys Arg His
                100                 105                 110 gac ctg ccg tac cac gtc atc ggc tcc gac ctc gcc ggt gtc gtc ctg     384
Asp Leu Pro Tyr His Val Ile Gly Ser Asp Leu Ala Gly Val Val Leu
            115                 120                 125 cgc acc ggt ccg ggc gtc aac gcc tgg cag gcg ggc gac gag gtc gtc     432
Arg Thr Gly Pro Gly Val Asn Ala Trp Gln Ala Gly Asp Glu Val Val
        130                 135                 140 gcg cac tgc ctc tcc gtc gag ctg gag tcc tcc gac ggc cac aac gac     480
Ala His Cys Leu Ser Val Glu Leu Glu Ser Ser Asp Gly His Asn Asp
145                 150                 155                 160 acg atg ctc gac ccc gag cag cgc atc tgg ggc ttc gag acc aac ttc     528
Thr Met Leu Asp Pro Glu Gln Arg Ile Trp Gly Phe Glu Thr Asn Phe
                165                 170                 175
```

```
ggc ggc ctc gcg gag atc gcg ctg gtc aag tcc aac cag ctg atg ccg      576
Gly Gly Leu Ala Glu Ile Ala Leu Val Lys Ser Asn Gln Leu Met Pro
            180                 185                 190 aag ccg gac cac ctg agc tgg gag gag gcc gcc gct ccc ggc ctg gtc      624
Lys Pro Asp His Leu Ser Trp Glu Glu Ala Ala Ala Pro Gly Leu Val
        195                 200                 205 aac tcc acc gcg tac cgc cag ctc gtc tcc cgc aac ggc gcc ggc atg      672
Asn Ser Thr Ala Tyr Arg Gln Leu Val Ser Arg Asn Gly Ala Gly Met
    210                 215                 220 aag cag ggc gac aac gtg ctc atc tgg ggc gcg agc ggc gga ctc ggc      720
Lys Gln Gly Asp Asn Val Leu Ile Trp Gly Ala Ser Gly Gly Leu Gly
225                 230                 235                 240 tcg tac gcc acc cag ttc gcc ctc gcc ggc ggc gcc aac ccg atc tgc      768
Ser Tyr Ala Thr Gln Phe Ala Leu Ala Gly Gly Ala Asn Pro Ile Cys
                245                 250                 255 gtc gtc tcc tcg ccg cag aag gcg gag atc tgc cgc gcg atg ggc gcc      816
Val Val Ser Ser Pro Gln Lys Ala Glu Ile Cys Arg Ala Met Gly Ala
            260                 265                 270 gag gcg atc atc gac cgc aac gcc gag ggc tac cgg ttc tgg aag gac      864
Glu Ala Ile Ile Asp Arg Asn Ala Glu Gly Tyr Arg Phe Trp Lys Asp
        275                 280                 285 gag aac acc cag gac ccg aag gag tgg aag cgc ttc ggc aag cgc atc      912
Glu Asn Thr Gln Asp Pro Lys Glu Trp Lys Arg Phe Gly Lys Arg Ile
    290                 295                 300 cgc gaa ctg acc ggc ggc gag gac atc gac atc gtc ttc gag cac ccc      960
Arg Glu Leu Thr Gly Gly Glu Asp Ile Asp Ile Val Phe Glu His Pro
305                 310                 315                 320 ggc cgc gag acc ttc ggc gcc tcc gtc ttc gtc acc cgc aag ggc ggc     1008
Gly Arg Glu Thr Phe Gly Ala Ser Val Phe Val Thr Arg Lys Gly Gly
                325                 330                 335 acc atc acc acc tgc gcc tcg acc tcg ggc tac atg cac gag tac gac     1056
Thr Ile Thr Thr Cys Ala Ser Thr Ser Gly Tyr Met His Glu Tyr Asp
            340                 345                 350 aac cgc tac ctg tgg atg tcc ctg aag cgc atc atc ggc tcg cac ttc     1104
Asn Arg Tyr Leu Trp Met Ser Leu Lys Arg Ile Ile Gly Ser His Phe
        355                 360                 365 gcc aac tac cgc gag gcc tgg gag gcc aac cgc ctc atc gcc aag ggc     1152
Ala Asn Tyr Arg Glu Ala Trp Glu Ala Asn Arg Leu Ile Ala Lys Gly
    370                 375                 380 agg atc cac ccc acg ctc tcc aag gtg tac tcc ctc gag gac acc ggc     1200
Arg Ile His Pro Thr Leu Ser Lys Val Tyr Ser Leu Glu Asp Thr Gly
385                 390                 395                 400 cag gcc gcc tac gac gtc cac cgc aac ctc cac cag ggc aag gtc ggc     1248
Gln Ala Ala Tyr Asp Val His Arg Asn Leu His Gln Gly Lys Val Gly
                405                 410                 415 gtg ctg tgc ctg gcg ccc gag gag ggc ctg ggc gtg cgc gac cgg gag     1296
Val Leu Cys Leu Ala Pro Glu Glu Gly Leu Gly Val Arg Asp Arg Glu
            420                 425                 430 aag cgc gcg cag cac ctc gac gcc atc aac cgc ttc cgg aac atc tga     1344
Lys Arg Ala Gln His Leu Asp Ala Ile Asn Arg Phe Arg Asn Ile
        435                 440                 445

<210> SEQ ID NO 32
<211> LENGTH: 447
<212> TYPE: PRT
<213> ORGANISM: Streptomyces coelicolor

<400> SEQUENCE: 32

Val Thr Val Lys Asp Ile Leu Asp Ala Ile Gln Ser Pro Asp Ser Thr
1               5                   10                  15
```

```
Pro Ala Asp Ile Ala Ala Leu Pro Leu Pro Glu Ser Tyr Arg Ala Ile
            20                  25                  30

Thr Val His Lys Asp Glu Thr Glu Met Phe Ala Gly Leu Glu Thr Arg
            35                  40                  45

Asp Lys Asp Pro Arg Lys Ser Ile His Leu Asp Asp Val Pro Val Pro
 50                  55                  60

Glu Leu Gly Pro Gly Glu Ala Leu Val Ala Val Met Ala Ser Ser Val
 65                  70                  75                  80

Asn Tyr Asn Ser Val Trp Thr Ser Ile Phe Glu Pro Leu Ser Thr Phe
                85                  90                  95

Gly Phe Leu Glu Arg Tyr Gly Arg Val Ser Asp Leu Ala Lys Arg His
            100                 105                 110

Asp Leu Pro Tyr His Val Ile Gly Ser Asp Leu Ala Gly Val Val Leu
            115                 120                 125

Arg Thr Gly Pro Gly Val Asn Ala Trp Gln Ala Gly Asp Glu Val Val
130                 135                 140

Ala His Cys Leu Ser Val Glu Leu Glu Ser Ser Asp Gly His Asn Asp
145                 150                 155                 160

Thr Met Leu Asp Pro Glu Gln Arg Ile Trp Gly Phe Glu Thr Asn Phe
                165                 170                 175

Gly Gly Leu Ala Glu Ile Ala Leu Val Lys Ser Asn Gln Leu Met Pro
            180                 185                 190

Lys Pro Asp His Leu Ser Trp Glu Glu Ala Ala Pro Gly Leu Val
            195                 200                 205

Asn Ser Thr Ala Tyr Arg Gln Leu Val Ser Arg Asn Gly Ala Gly Met
            210                 215                 220

Lys Gln Gly Asp Asn Val Leu Ile Trp Gly Ala Ser Gly Gly Leu Gly
225                 230                 235                 240

Ser Tyr Ala Thr Gln Phe Ala Leu Ala Gly Gly Ala Asn Pro Ile Cys
                245                 250                 255

Val Val Ser Ser Pro Gln Lys Ala Glu Ile Cys Arg Ala Met Gly Ala
            260                 265                 270

Glu Ala Ile Ile Asp Arg Asn Ala Glu Gly Tyr Arg Phe Trp Lys Asp
            275                 280                 285

Glu Asn Thr Gln Asp Pro Lys Glu Trp Lys Arg Phe Gly Lys Arg Ile
            290                 295                 300

Arg Glu Leu Thr Gly Gly Glu Asp Ile Asp Ile Val Phe Glu His Pro
305                 310                 315                 320

Gly Arg Glu Thr Phe Gly Ala Ser Val Phe Val Thr Arg Lys Gly Gly
                325                 330                 335

Thr Ile Thr Thr Cys Ala Ser Thr Ser Gly Tyr Met His Glu Tyr Asp
            340                 345                 350

Asn Arg Tyr Leu Trp Met Ser Leu Lys Arg Ile Ile Gly Ser His Phe
            355                 360                 365

Ala Asn Tyr Arg Glu Ala Trp Glu Ala Asn Arg Leu Ile Ala Lys Gly
            370                 375                 380

Arg Ile His Pro Thr Leu Ser Lys Val Tyr Ser Leu Glu Asp Thr Gly
385                 390                 395                 400

Gln Ala Ala Tyr Asp Val His Arg Asn Leu His Gln Gly Lys Val Gly
                405                 410                 415

Val Leu Cys Leu Ala Pro Glu Glu Gly Leu Gly Val Arg Asp Arg Glu
            420                 425                 430
```

Lys Arg Ala Gln His Leu Asp Ala Ile Asn Arg Phe Arg Asn Ile
            435                 440                 445

<210> SEQ ID NO 33
<211> LENGTH: 398
<212> TYPE: PRT
<213> ORGANISM: Treponema dentricola
<220> FEATURE:
<221> NAME/KEY: misc_feature
<222> LOCATION: (398)..(398)
<223> OTHER INFORMATION: Xaa can be any naturally occurring amino acid

<400> SEQUENCE: 33

Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
    50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
            180                 185                 190

Glu Ala Ala Ala Thr Val Lys Val Met Gly Gly Glu Asp Trp Glu Arg
        195                 200                 205

Trp Ile Lys Gln Leu Ser Lys Glu Gly Leu Leu Glu Glu Gly Cys Ile
    210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
    290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Glu Asn Arg Ile Arg Ile
                325                 330                 335

Asp Asp Trp Glu Leu Glu Glu Asp Val Gln Lys Ala Val Ser Ala Leu

```
                    340                 345                 350
Met Glu Lys Val Thr Gly Glu Asn Ala Glu Ser Leu Thr Asp Leu Ala
            355                 360                 365

Gly Tyr Arg His Asp Phe Leu Ala Ser Asn Gly Phe Asp Val Glu Gly
    370                 375                 380

Ile Asn Tyr Glu Ala Glu Val Glu Arg Phe Asp Arg Ile Xaa
385                 390                 395

<210> SEQ ID NO 34
<211> LENGTH: 1407
<212> TYPE: DNA
<213> ORGANISM: Clostridium saccharoperbutylacetonicum
<220> FEATURE:
<221> NAME/KEY: CDS
<222> LOCATION: (1)..(1407)

<400> SEQUENCE: 34 atg att aaa gac acg cta gtt tct ata aca aaa gat tta aaa tta aaa      48
Met Ile Lys Asp Thr Leu Val Ser Ile Thr Lys Asp Leu Lys Leu Lys
1               5                   10                  15 aca aat gtt gaa aat gcc aat cta aag aac tac aag gat gat tct tca      96
Thr Asn Val Glu Asn Ala Asn Leu Lys Asn Tyr Lys Asp Asp Ser Ser
                20                  25                  30 tgt ttc gga gtt ttc gaa aat gtt gaa aat gct ata agc aat gcc gta     144
Cys Phe Gly Val Phe Glu Asn Val Glu Asn Ala Ile Ser Asn Ala Val
            35                  40                  45 cac gca caa aag ata tta tcc ctt cat tat aca aaa gaa caa aga gaa     192
His Ala Gln Lys Ile Leu Ser Leu His Tyr Thr Lys Glu Gln Arg Glu
        50                  55                  60 aaa atc ata act gag ata aga aag gcc gca tta gaa aat aaa gag att     240
Lys Ile Ile Thr Glu Ile Arg Lys Ala Ala Leu Glu Asn Lys Glu Ile
65                  70                  75                  80 cta gct aca atg att ctt gaa gaa aca cat atg gga aga tat gaa gat     288
Leu Ala Thr Met Ile Leu Glu Glu Thr His Met Gly Arg Tyr Glu Asp
                85                  90                  95 aaa ata tta aag cat gaa tta gta gct aaa tac act cct ggg aca gaa     336
Lys Ile Leu Lys His Glu Leu Val Ala Lys Tyr Thr Pro Gly Thr Glu
            100                 105                 110 gat tta act act act gct tgg tca gga gat aac ggg ctt aca gtt gta     384
Asp Leu Thr Thr Thr Ala Trp Ser Gly Asp Asn Gly Leu Thr Val Val
        115                 120                 125 gaa atg tct cca tat ggc gtt ata ggt gca ata act cct tct acg aat     432
Glu Met Ser Pro Tyr Gly Val Ile Gly Ala Ile Thr Pro Ser Thr Asn
    130                 135                 140 cca act gaa act gta ata tgt aat agt ata ggc atg ata gct gct gga     480
Pro Thr Glu Thr Val Ile Cys Asn Ser Ile Gly Met Ile Ala Ala Gly
145                 150                 155                 160 aat act gtg gta ttt aac gga cat cca ggc gct aaa aaa tgt gtt gct     528
Asn Thr Val Val Phe Asn Gly His Pro Gly Ala Lys Lys Cys Val Ala
                165                 170                 175 ttt gct gtc gaa atg ata aat aaa gct att att tca tgt ggt ggt cct     576
Phe Ala Val Glu Met Ile Asn Lys Ala Ile Ile Ser Cys Gly Gly Pro
            180                 185                 190 gag aat tta gta aca act ata aaa aat cca act atg gac tct cta gat     624
Glu Asn Leu Val Thr Thr Ile Lys Asn Pro Thr Met Asp Ser Leu Asp
        195                 200                 205 gca att att aag cac cct tca ata aaa cta ctt tgc gga act gga ggg     672
Ala Ile Ile Lys His Pro Ser Ile Lys Leu Leu Cys Gly Thr Gly Gly
    210                 215                 220 cca gga atg gta aaa acc ctc tta aat tct ggt aag aaa gct ata ggt     720
```

```
Pro Gly Met Val Lys Thr Leu Leu Asn Ser Gly Lys Lys Ala Ile Gly
225                 230                 235                 240 gct ggt gct gga aat cca cca gtt att gta gat gat act gct gat ata      768
Ala Gly Ala Gly Asn Pro Pro Val Ile Val Asp Asp Thr Ala Asp Ile
                        245                 250                 255 gaa aag gct ggt aag agt atc att gaa ggc tgt tct ttt gat aat aat      816
Glu Lys Ala Gly Lys Ser Ile Ile Glu Gly Cys Ser Phe Asp Asn Asn
                260                 265                 270 tta cct tgt att gca gaa aaa gaa gta ttt gtt ttt gag aac gtt gca      864
Leu Pro Cys Ile Ala Glu Lys Glu Val Phe Val Phe Glu Asn Val Ala
            275                 280                 285 gat gat tta ata tct aac atg cta aaa aat aat gct gta att ata aat      912
Asp Asp Leu Ile Ser Asn Met Leu Lys Asn Asn Ala Val Ile Ile Asn
        290                 295                 300 gaa gat caa gta tca aag tta ata gat tta gta tta caa aaa aat aat      960
Glu Asp Gln Val Ser Lys Leu Ile Asp Leu Val Leu Gln Lys Asn Asn
305                 310                 315                 320 gaa act caa gaa tac tct ata aat aag aaa tgg gtc gga aaa gat gca     1008
Glu Thr Gln Glu Tyr Ser Ile Asn Lys Lys Trp Val Gly Lys Asp Ala
                    325                 330                 335 aaa tta ttc tta gat gaa ata gat gtt gag tct cct tca agt gtt aaa     1056
Lys Leu Phe Leu Asp Glu Ile Asp Val Glu Ser Pro Ser Ser Val Lys
                340                 345                 350 tgc ata atc tgc gaa gta agt gca agg cat cca ttt gtt atg aca gaa     1104
Cys Ile Ile Cys Glu Val Ser Ala Arg His Pro Phe Val Met Thr Glu
            355                 360                 365 ctc atg atg cca ata tta cca att gta aga gtt aaa gat ata gat gaa     1152
Leu Met Met Pro Ile Leu Pro Ile Val Arg Val Lys Asp Ile Asp Glu
        370                 375                 380 gct att gaa tat gca aaa ata gca gaa caa aat aga aaa cat agt gcc     1200
Ala Ile Glu Tyr Ala Lys Ile Ala Glu Gln Asn Arg Lys His Ser Ala
385                 390                 395                 400 tat att tat tca aaa aat ata gac aac cta aat agg ttt gaa aga gaa     1248
Tyr Ile Tyr Ser Lys Asn Ile Asp Asn Leu Asn Arg Phe Glu Arg Glu
                    405                 410                 415 atc gat act act atc ttt gta aag aat gct aaa tct ttt gcc ggt gtt     1296
Ile Asp Thr Thr Ile Phe Val Lys Asn Ala Lys Ser Phe Ala Gly Val
                420                 425                 430 ggt tat gaa gca gaa ggc ttt aca act ttc act att gct gga tcc act     1344
Gly Tyr Glu Ala Glu Gly Phe Thr Thr Phe Thr Ile Ala Gly Ser Thr
            435                 440                 445 ggt gaa gga ata act tct gca aga aat ttt aca aga caa aga aga tgt     1392
Gly Glu Gly Ile Thr Ser Ala Arg Asn Phe Thr Arg Gln Arg Arg Cys
        450                 455                 460 gta ctc gcc ggt taa                                                 1407
Val Leu Ala Gly
465

<210> SEQ ID NO 35
<211> LENGTH: 468
<212> TYPE: PRT
<213> ORGANISM: Clostridium saccharoperbutylacetonicum

<400> SEQUENCE: 35

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45
```

-continued

```
His Ala Gln Lys Ile Leu Ser Leu His Tyr Thr Lys Glu Gln Arg Glu
         50                  55                  60

Lys Ile Ile Thr Glu Ile Arg Lys Ala Ala Leu Glu Asn Lys Glu Ile
 65                  70                  75                  80

Leu Ala Thr Met Ile Leu Glu Glu Thr His Met Gly Arg Tyr Glu Asp
                     85                  90                  95

Lys Ile Leu Lys His Glu Leu Val Ala Lys Tyr Thr Pro Gly Thr Glu
                 100                 105                 110

Asp Leu Thr Thr Thr Ala Trp Ser Gly Asp Asn Gly Leu Thr Val Val
             115                 120                 125

Glu Met Ser Pro Tyr Gly Val Ile Gly Ala Ile Thr Pro Ser Thr Asn
         130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                 165                 170                 175

Phe Ala Val Glu Met Ile Asn Lys Ala Ile Ile Ser Cys Gly Gly Pro
                 180                 185                 190

Glu Asn Leu Val Thr Thr Ile Lys Asn Pro Thr Met Asp Ser Leu Asp
             195                 200                 205

Ala Ile Ile Lys His Pro Ser Ile Lys Leu Leu Cys Gly Thr Gly Gly
         210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                 245                 250                 255

Glu Lys Ala Gly Lys Ser Ile Ile Glu Gly Cys Ser Phe Asp Asn Asn
                 260                 265                 270

Leu Pro Cys Ile Ala Glu Lys Glu Val Phe Val Phe Glu Asn Val Ala
             275                 280                 285

Asp Asp Leu Ile Ser Asn Met Leu Lys Asn Asn Ala Val Ile Ile Asn
         290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                 325                 330                 335

Lys Leu Phe Leu Asp Glu Ile Asp Val Glu Ser Pro Ser Ser Val Lys
             340                 345                 350

Cys Ile Ile Cys Glu Val Ser Ala Arg His Pro Phe Val Met Thr Glu
         355                 360                 365

Leu Met Met Pro Ile Leu Pro Ile Val Arg Val Lys Asp Ile Asp Glu
370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                 405                 410                 415

Ile Asp Thr Thr Ile Phe Val Lys Asn Ala Lys Ser Phe Ala Gly Val
             420                 425                 430

Gly Tyr Glu Ala Glu Gly Phe Thr Thr Phe Thr Ile Ala Gly Ser Thr
         435                 440                 445

Gly Glu Gly Ile Thr Ser Ala Arg Asn Phe Thr Arg Gln Arg Arg Cys
450                 455                 460
```

-continued

Val Leu Ala Gly
465

<210> SEQ ID NO 36
<211> LENGTH: 1164
<212> TYPE: DNA
<213> ORGANISM: Escherichia coli
<220> FEATURE:
<221> NAME/KEY: CDS
<222> LOCATION: (1)..(1164)

<400> SEQUENCE: 36

| | | | | | | | | | | | | | | | | |
|---|---|---|---|---|---|---|---|---|---|---|---|---|---|---|---|---|
| atg | aac | aac | ttt | aat | ctg | cac | acc | cca | acc | cgc | att | ctg | ttt | ggt | aaa | 48 |
| Met | Asn | Asn | Phe | Asn | Leu | His | Thr | Pro | Thr | Arg | Ile | Leu | Phe | Gly | Lys | |
| 1 | | | | 5 | | | | | 10 | | | | | 15 | | |
| ggc | gca | atc | gct | ggt | tta | cgc | gaa | caa | att | cct | cac | gat | gct | cgc | gta | 96 |
| Gly | Ala | Ile | Ala | Gly | Leu | Arg | Glu | Gln | Ile | Pro | His | Asp | Ala | Arg | Val | |
| | | | 20 | | | | | 25 | | | | | 30 | | | |
| ttg | att | acc | tac | ggc | ggc | ggc | agc | gtg | aaa | aaa | acc | ggc | gtt | ctc | gat | 144 |
| Leu | Ile | Thr | Tyr | Gly | Gly | Gly | Ser | Val | Lys | Lys | Thr | Gly | Val | Leu | Asp | |
| | | 35 | | | | | 40 | | | | | 45 | | | | |
| caa | gtt | ctg | gat | gcc | ctg | aaa | ggc | atg | gac | gtg | ctg | gaa | ttt | ggc | ggt | 192 |
| Gln | Val | Leu | Asp | Ala | Leu | Lys | Gly | Met | Asp | Val | Leu | Glu | Phe | Gly | Gly | |
| | 50 | | | | | 55 | | | | | 60 | | | | | |
| att | gag | cca | aac | ccg | gct | tat | gaa | acg | ctg | atg | aac | gcc | gtg | aaa | ctg | 240 |
| Ile | Glu | Pro | Asn | Pro | Ala | Tyr | Glu | Thr | Leu | Met | Asn | Ala | Val | Lys | Leu | |
| 65 | | | | | 70 | | | | | 75 | | | | | 80 | |
| gtt | cgc | gaa | cag | aaa | gtg | act | ttc | ctg | ctg | gcg | gtt | ggc | ggc | ggt | tct | 288 |
| Val | Arg | Glu | Gln | Lys | Val | Thr | Phe | Leu | Leu | Ala | Val | Gly | Gly | Gly | Ser | |
| | | | | 85 | | | | | 90 | | | | | 95 | | |
| gta | ctg | gac | ggc | acc | aaa | ttt | atc | gcc | gca | gcg | gct | aac | tat | ccg | gaa | 336 |
| Val | Leu | Asp | Gly | Thr | Lys | Phe | Ile | Ala | Ala | Ala | Ala | Asn | Tyr | Pro | Glu | |
| | | | 100 | | | | | 105 | | | | | 110 | | | |
| aat | atc | gat | ccg | tgg | cac | att | ctg | caa | acg | ggc | ggt | aaa | gag | att | aaa | 384 |
| Asn | Ile | Asp | Pro | Trp | His | Ile | Leu | Gln | Thr | Gly | Gly | Lys | Glu | Ile | Lys | |
| | | 115 | | | | | 120 | | | | | 125 | | | | |
| agc | gcc | atc | ccg | atg | ggc | tgt | gtg | ctg | acg | ctg | cca | gca | acc | ggt | tca | 432 |
| Ser | Ala | Ile | Pro | Met | Gly | Cys | Val | Leu | Thr | Leu | Pro | Ala | Thr | Gly | Ser | |
| | 130 | | | | | 135 | | | | | 140 | | | | | |
| gaa | tcc | aac | gca | ggc | gcg | gtg | atc | tcc | cgt | aaa | acc | aca | ggc | gac | aag | 480 |
| Glu | Ser | Asn | Ala | Gly | Ala | Val | Ile | Ser | Arg | Lys | Thr | Thr | Gly | Asp | Lys | |
| 145 | | | | | 150 | | | | | 155 | | | | | 160 | |
| cag | gcg | ttc | cat | tct | gcc | cat | gtt | cag | ccg | gta | ttt | gcc | gtg | ctc | gat | 528 |
| Gln | Ala | Phe | His | Ser | Ala | His | Val | Gln | Pro | Val | Phe | Ala | Val | Leu | Asp | |
| | | | | 165 | | | | | 170 | | | | | 175 | | |
| ccg | gtt | tat | acc | tac | acc | ctg | ccg | ccg | cgt | cag | gtg | gct | aac | ggc | gta | 576 |
| Pro | Val | Tyr | Thr | Tyr | Thr | Leu | Pro | Pro | Arg | Gln | Val | Ala | Asn | Gly | Val | |
| | | | 180 | | | | | 185 | | | | | 190 | | | |
| gtg | gac | gcc | ttt | gta | cac | acc | gtg | gaa | cag | tat | gtt | acc | aaa | ccg | gtt | 624 |
| Val | Asp | Ala | Phe | Val | His | Thr | Val | Glu | Gln | Tyr | Val | Thr | Lys | Pro | Val | |
| | | 195 | | | | | 200 | | | | | 205 | | | | |
| gat | gcc | aaa | att | cag | gac | cgt | ttc | gca | gaa | ggc | att | ttg | ctg | acg | cta | 672 |
| Asp | Ala | Lys | Ile | Gln | Asp | Arg | Phe | Ala | Glu | Gly | Ile | Leu | Leu | Thr | Leu | |
| | 210 | | | | | 215 | | | | | 220 | | | | | |
| atc | gaa | gat | ggt | ccg | aaa | gcc | ctg | aaa | gag | cca | gaa | aac | tac | gat | gtg | 720 |
| Ile | Glu | Asp | Gly | Pro | Lys | Ala | Leu | Lys | Glu | Pro | Glu | Asn | Tyr | Asp | Val | |
| 225 | | | | | 230 | | | | | 235 | | | | | 240 | |
| cgc | gcc | aac | gtc | atg | tgg | gcg | gcg | act | cag | gcg | ctg | aac | ggt | ttg | att | 768 |
| Arg | Ala | Asn | Val | Met | Trp | Ala | Ala | Thr | Gln | Ala | Leu | Asn | Gly | Leu | Ile | |
| | | | | 245 | | | | | 250 | | | | | 255 | | |
| ggc | gct | ggc | gta | ccg | cag | gac | tgg | gca | acg | cat | atg | ctg | ggc | cac | gaa | 816 |

```
Gly Ala Gly Val Pro Gln Asp Trp Ala Thr His Met Leu Gly His Glu
            260                 265                 270 ctg act gcg atg cac ggt ctg gat cac gcg caa aca ctg gct atc gtc      864
Leu Thr Ala Met His Gly Leu Asp His Ala Gln Thr Leu Ala Ile Val
        275                 280                 285 ctg cct gca ctg tgg aat gaa aaa cgc gat acc aag cgc gct aag ctg      912
Leu Pro Ala Leu Trp Asn Glu Lys Arg Asp Thr Lys Arg Ala Lys Leu
290                 295                 300 ctg caa tat gct gaa cgc gtc tgg aac atc act gaa ggt tcc gat gat      960
Leu Gln Tyr Ala Glu Arg Val Trp Asn Ile Thr Glu Gly Ser Asp Asp
305                 310                 315                 320 gag cgt att gac gcc gcg att gcc gca acc cgc aat ttc ttt gag caa     1008
Glu Arg Ile Asp Ala Ala Ile Ala Ala Thr Arg Asn Phe Phe Glu Gln
                325                 330                 335 tta ggc gtg ccg acc cac ctc tcc gac tac ggt ctg gac ggc agc tcc     1056
Leu Gly Val Pro Thr His Leu Ser Asp Tyr Gly Leu Asp Gly Ser Ser
            340                 345                 350 atc ccg gct ttg ctg aaa aaa ctg gaa gag cac ggc atg acc caa ctg     1104
Ile Pro Ala Leu Leu Lys Lys Leu Glu Glu His Gly Met Thr Gln Leu
        355                 360                 365 ggc gaa aat cat gac att acg ttg gat gtc agc cgc cgt ata tac gaa     1152
Gly Glu Asn His Asp Ile Thr Leu Asp Val Ser Arg Arg Ile Tyr Glu
370                 375                 380 gcc gcc cgc taa                                                     1164
Ala Ala Arg
385

<210> SEQ ID NO 37
<211> LENGTH: 387
<212> TYPE: PRT
<213> ORGANISM: Escherichia coli

<400> SEQUENCE: 37

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190
```

```
Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
        210                 215                 220

Ile Glu Asp Gly Pro Lys Ala Leu Lys Glu Pro Glu Asn Tyr Asp Val
225                 230                 235                 240

Arg Ala Asn Val Met Trp Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 38
<211> LENGTH: 2577
<212> TYPE: DNA
<213> ORGANISM: Clostridium acetobutylicum
<220> FEATURE:
<221> NAME/KEY: CDS
<222> LOCATION: (1)..(2577)

<400> SEQUENCE: 38 atg aaa gtt aca aat caa aaa gaa cta aaa caa aag cta aat gaa ttg      48
Met Lys Val Thr Asn Gln Lys Glu Leu Lys Gln Lys Leu Asn Glu Leu
1               5                   10                  15 aga gaa gcg caa aag aag ttt gca acc tat act caa gag caa gtt gat      96
Arg Glu Ala Gln Lys Lys Phe Ala Thr Tyr Thr Gln Glu Gln Val Asp
            20                  25                  30 aaa att ttt aaa caa tgt gcc ata gcc gca gct aaa gaa aga ata aac     144
Lys Ile Phe Lys Gln Cys Ala Ile Ala Ala Ala Lys Glu Arg Ile Asn
        35                  40                  45 tta gct aaa tta gca gta gaa gaa aca gga ata ggt ctt gta gaa gat     192
Leu Ala Lys Leu Ala Val Glu Glu Thr Gly Ile Gly Leu Val Glu Asp
    50                  55                  60 aaa att ata aaa aat cat ttt gca gca gaa tat ata tac aat aaa tat     240
Lys Ile Ile Lys Asn His Phe Ala Ala Glu Tyr Ile Tyr Asn Lys Tyr
65                  70                  75                  80 aaa aat gaa aaa act tgt ggc ata ata gac cat gac gat tct tta ggc     288
Lys Asn Glu Lys Thr Cys Gly Ile Ile Asp His Asp Asp Ser Leu Gly
                85                  90                  95 ata aca aag gtt gct gaa cca att gga att gtt gca gcc ata gtt cct     336
Ile Thr Lys Val Ala Glu Pro Ile Gly Ile Val Ala Ala Ile Val Pro
            100                 105                 110 act act aat cca act tcc aca gca att ttc aaa tca tta att tct tta     384
```

```
             Thr Thr Asn Pro Thr Ser Thr Ala Ile Phe Lys Ser Leu Ile Ser Leu
                     115                 120                 125 aaa aca aga aac gca ata ttc ttt tca cca cat cca cgt gca aaa aaa      432
Lys Thr Arg Asn Ala Ile Phe Phe Ser Pro His Pro Arg Ala Lys Lys
        130                 135                 140 tct aca att gct gca gca aaa tta att tta gat gca gct gtt aaa gca      480
Ser Thr Ile Ala Ala Ala Lys Leu Ile Leu Asp Ala Ala Val Lys Ala
145                 150                 155                 160 gga gca cct aaa aat ata ata ggc tgg ata gat gag cca tca ata gaa      528
Gly Ala Pro Lys Asn Ile Ile Gly Trp Ile Asp Glu Pro Ser Ile Glu
                165                 170                 175 ctt tct caa gat ttg atg agt gaa gct gat ata ata tta gca aca gga      576
Leu Ser Gln Asp Leu Met Ser Glu Ala Asp Ile Ile Leu Ala Thr Gly
            180                 185                 190 ggt cct tca atg gtt aaa gcg gcc tat tca tct gga aaa cct gca att      624
Gly Pro Ser Met Val Lys Ala Ala Tyr Ser Ser Gly Lys Pro Ala Ile
        195                 200                 205 ggt gtt gga gca gga aat aca cca gca ata ata gat gag agt gca gat      672
Gly Val Gly Ala Gly Asn Thr Pro Ala Ile Ile Asp Glu Ser Ala Asp
210                 215                 220 ata gat atg gca gta agc tcc ata att tta tca aag act tat gac aat      720
Ile Asp Met Ala Val Ser Ser Ile Ile Leu Ser Lys Thr Tyr Asp Asn
225                 230                 235                 240 gga gta ata tgc gct tct gaa caa tca ata tta gtt atg aat tca ata      768
Gly Val Ile Cys Ala Ser Glu Gln Ser Ile Leu Val Met Asn Ser Ile
                245                 250                 255 tac gaa aaa gtt aaa gag gaa ttt gta aaa cga gga tca tat ata ctc      816
Tyr Glu Lys Val Lys Glu Glu Phe Val Lys Arg Gly Ser Tyr Ile Leu
            260                 265                 270 aat caa aat gaa ata gct aaa ata aaa gaa act atg ttt aaa aat gga      864
Asn Gln Asn Glu Ile Ala Lys Ile Lys Glu Thr Met Phe Lys Asn Gly
        275                 280                 285 gct att aat gct gac ata gtt gga aaa tct gct tat ata att gct aaa      912
Ala Ile Asn Ala Asp Ile Val Gly Lys Ser Ala Tyr Ile Ile Ala Lys
        290                 295                 300 atg gca gga att gaa gtt cct caa act aca aag ata ctt ata ggc gaa      960
Met Ala Gly Ile Glu Val Pro Gln Thr Thr Lys Ile Leu Ile Gly Glu
305                 310                 315                 320 gta caa tct gtt gaa aaa agc gag ctg ttc tca cat gaa aaa cta tca     1008
Val Gln Ser Val Glu Lys Ser Glu Leu Phe Ser His Glu Lys Leu Ser
                325                 330                 335 cca gta ctt gca atg tat aaa gtt aag gat ttt gat gaa gct cta aaa     1056
Pro Val Leu Ala Met Tyr Lys Val Lys Asp Phe Asp Glu Ala Leu Lys
            340                 345                 350 aag gca caa agg cta ata gaa tta ggt gga agt gga cac acg tca tct     1104
Lys Ala Gln Arg Leu Ile Glu Leu Gly Gly Ser Gly His Thr Ser Ser
        355                 360                 365 tta tat ata gat tca caa aac aat aag gat aaa gtt aaa gaa ttt gga     1152
Leu Tyr Ile Asp Ser Gln Asn Asn Lys Asp Lys Val Lys Glu Phe Gly
        370                 375                 380 tta gca atg aaa act tca agg aca ttt att aac atg cct tct tca cag     1200
Leu Ala Met Lys Thr Ser Arg Thr Phe Ile Asn Met Pro Ser Ser Gln
385                 390                 395                 400 gga gca agc gga gat tta tac aat ttt gcg ata gca cca tca ttt act     1248
Gly Ala Ser Gly Asp Leu Tyr Asn Phe Ala Ile Ala Pro Ser Phe Thr
                405                 410                 415 ctt gga tgc ggc act tgg gga gga aac tct gta tcg caa aat gta gag     1296
Leu Gly Cys Gly Thr Trp Gly Gly Asn Ser Val Ser Gln Asn Val Glu
            420                 425                 430
```

```
cct aaa cat tta tta aat att aaa agt gtt gct gaa aga agg gaa aat    1344
Pro Lys His Leu Leu Asn Ile Lys Ser Val Ala Glu Arg Arg Glu Asn
        435                 440                 445 atg ctt tgg ttt aaa gtg cca caa aaa ata tat ttt aaa tat gga tgt    1392
Met Leu Trp Phe Lys Val Pro Gln Lys Ile Tyr Phe Lys Tyr Gly Cys
    450                 455                 460 ctt aga ttt gca tta aaa gaa tta aaa gat atg aat aag aaa aga gcc    1440
Leu Arg Phe Ala Leu Lys Glu Leu Lys Asp Met Asn Lys Lys Arg Ala
465                 470                 475                 480 ttt ata gta aca gat aaa gat ctt ttt aaa ctt gga tat gtt aat aaa    1488
Phe Ile Val Thr Asp Lys Asp Leu Phe Lys Leu Gly Tyr Val Asn Lys
                    485                 490                 495 ata aca aag gta cta gat gag ata gat att aaa tac agt ata ttt aca    1536
Ile Thr Lys Val Leu Asp Glu Ile Asp Ile Lys Tyr Ser Ile Phe Thr
                500                 505                 510 gat att aaa tct gat cca act att gat tca gta aaa aaa ggt gct aaa    1584
Asp Ile Lys Ser Asp Pro Thr Ile Asp Ser Val Lys Lys Gly Ala Lys
            515                 520                 525 gaa atg ctt aac ttt gaa cct gat act ata atc tct att ggt ggt gga    1632
Glu Met Leu Asn Phe Glu Pro Asp Thr Ile Ile Ser Ile Gly Gly Gly
530                 535                 540 tcg cca atg gat gca gca aag gtt atg cac ttg tta tat gaa tat cca    1680
Ser Pro Met Asp Ala Ala Lys Val Met His Leu Leu Tyr Glu Tyr Pro
545                 550                 555                 560 gaa gca gaa att gaa aat cta gct ata aac ttt atg gat ata aga aag    1728
Glu Ala Glu Ile Glu Asn Leu Ala Ile Asn Phe Met Asp Ile Arg Lys
                    565                 570                 575 aga ata tgc aat ttc cct aaa tta ggt aca aag gcg att tca gta gct    1776
Arg Ile Cys Asn Phe Pro Lys Leu Gly Thr Lys Ala Ile Ser Val Ala
                580                 585                 590 att cct aca act gct ggt acc ggt tca gag gca aca cct ttt gca gtt    1824
Ile Pro Thr Thr Ala Gly Thr Gly Ser Glu Ala Thr Pro Phe Ala Val
            595                 600                 605 ata act aat gat gaa aca gga atg aaa tac cct tta act tct tat gaa    1872
Ile Thr Asn Asp Glu Thr Gly Met Lys Tyr Pro Leu Thr Ser Tyr Glu
        610                 615                 620 ttg acc cca aac atg gca ata ata gat act gaa tta atg tta aat atg    1920
Leu Thr Pro Asn Met Ala Ile Ile Asp Thr Glu Leu Met Leu Asn Met
625                 630                 635                 640 cct aga aaa tta aca gca gca act gga ata gat gca tta gtt cat gct    1968
Pro Arg Lys Leu Thr Ala Ala Thr Gly Ile Asp Ala Leu Val His Ala
                645                 650                 655 ata gaa gca tat gtt tcg gtt atg gct acg gat tat act gat gaa tta    2016
Ile Glu Ala Tyr Val Ser Val Met Ala Thr Asp Tyr Thr Asp Glu Leu
                660                 665                 670 gcc tta aga gca ata aaa atg ata ttt aaa tat ttg cct aga gcc tat    2064
Ala Leu Arg Ala Ile Lys Met Ile Phe Lys Tyr Leu Pro Arg Ala Tyr
            675                 680                 685 aaa aat ggg act aac gac att gaa gca aga gaa aaa atg gca cat gcc    2112
Lys Asn Gly Thr Asn Asp Ile Glu Ala Arg Glu Lys Met Ala His Ala
        690                 695                 700 tct aat att gcg ggg atg gca ttt gca aat gct ttc tta ggt gta tgc    2160
Ser Asn Ile Ala Gly Met Ala Phe Ala Asn Ala Phe Leu Gly Val Cys
705                 710                 715                 720 cat tca atg gct cat aaa ctt ggg gca atg cat cac gtt cca cat gga    2208
His Ser Met Ala His Lys Leu Gly Ala Met His His Val Pro His Gly
                725                 730                 735 att gct tgt gct gta tta ata gaa gaa gtt att aaa tat aac gct aca    2256
Ile Ala Cys Ala Val Leu Ile Glu Glu Val Ile Lys Tyr Asn Ala Thr
                740                 745                 750
```

```
gac tgt cca aca aag caa aca gca ttc cct caa tat aaa tct cct aat    2304
Asp Cys Pro Thr Lys Gln Thr Ala Phe Pro Gln Tyr Lys Ser Pro Asn
        755                 760                 765 gct aag aga aaa tat gct gaa att gca gag tat ttg aat tta aag ggt    2352
Ala Lys Arg Lys Tyr Ala Glu Ile Ala Glu Tyr Leu Asn Leu Lys Gly
        770                 775                 780 act agc gat acc gaa aag gta aca gcc tta ata gaa gct att tca aag    2400
Thr Ser Asp Thr Glu Lys Val Thr Ala Leu Ile Glu Ala Ile Ser Lys
785                 790                 795                 800 tta aag ata gat ttg agt att cca caa aat ata agt gcc gct gga ata    2448
Leu Lys Ile Asp Leu Ser Ile Pro Gln Asn Ile Ser Ala Ala Gly Ile
                805                 810                 815 aat aaa aaa gat ttt tat aat acg cta gat aaa atg tca gag ctt gct    2496
Asn Lys Lys Asp Phe Tyr Asn Thr Leu Asp Lys Met Ser Glu Leu Ala
            820                 825                 830 ttt gat gac caa tgt aca aca gct aat cct agg tat cca ctt ata agt    2544
Phe Asp Asp Gln Cys Thr Thr Ala Asn Pro Arg Tyr Pro Leu Ile Ser
        835                 840                 845 gaa ctt aag gat atc tat ata aaa tca ttt taa                        2577
Glu Leu Lys Asp Ile Tyr Ile Lys Ser Phe
850                 855
```

<210> SEQ ID NO 39
<211> LENGTH: 858
<212> TYPE: PRT
<213> ORGANISM: Clostridium acetobutylicum

<400> SEQUENCE: 39

```
Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220
```

```
Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
            245                 250                 255

Tyr Glu Lys Val Lys Glu Phe Val Lys Arg Gly Ser Tyr Ile Leu
        260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
        290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
                340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
            405                 410                 415

Leu Gly Cys Gly Thr Trp Gly Gly Asn Ser Val Ser Gln Asn Val Glu
        420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
    530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
        610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
```

-continued

```
                        645                 650                 655
Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
            675                 680                 685

Lys Asn Gly Thr Asn Asp Ile Glu Ala Arg Glu Lys Met Ala His Ala
            690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
                740                 745                 750

Asp Cys Pro Thr Lys Gln Thr Ala Phe Pro Gln Tyr Lys Ser Pro Asn
            755                 760                 765

Ala Lys Arg Lys Tyr Ala Glu Ile Ala Glu Tyr Leu Asn Leu Lys Gly
            770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
            835                 840                 845

Glu Leu Lys Asp Ile Tyr Ile Lys Ser Phe
850                 855
```